(12) United States Patent
Vontz et al.

US008193233B2

(10) Patent No.: US 8,193,233 B2
(45) Date of Patent: *Jun. 5, 2012

(54) ANTI-FUNGAL FORMULATION

(75) Inventors: Charles G. Vontz, Menlo Park, CA (US); Norifumi Nakamura, Sunnyvale, CA (US); Catherine de Porceri-Morton, San Jose, CA (US); Jeff Hughes, San Antonio, TX (US); Bhavesh Shah, San Antonio, TX (US); Peter Gertas, San Antonio, TX (US); Vitthal Kulkarni, San Antonio, TX (US)

(73) Assignee: Topica Pharmaceuticals, Inc., Palo Alto, CA (US)

( * ) Notice: Subject to any disclaimer, the term of this patent is extended or adjusted under 35 U.S.C. 154(b) by 53 days.

This patent is subject to a terminal disclaimer.

(21) Appl. No.: 12/750,563

(22) Filed: Mar. 30, 2010

(65) Prior Publication Data

US 2010/0210703 A1 Aug. 19, 2010

Related U.S. Application Data

(63) Continuation of application No. 12/705,555, filed on Feb. 12, 2010.

(60) Provisional application No. 61/152,658, filed on Feb. 13, 2009, provisional application No. 61/162,661, filed on Mar. 23, 2009.

(51) Int. Cl.
*A01N 43/52* (2006.01)
*A01N 25/34* (2006.01)
*A61K 31/415* (2006.01)

(52) U.S. Cl. ........................ 514/397; 424/404

(58) Field of Classification Search .................... 514/397
See application file for complete search history.

(56) References Cited

U.S. PATENT DOCUMENTS

| | | | |
|---|---|---|---|
| 4,636,519 A | 1/1987 | Seo et al. | |
| 4,738,976 A | 4/1988 | Seo et al. | |
| 5,391,558 A | 2/1995 | Seo et al. | |
| 5,900,488 A | 5/1999 | Kodama et al. | |
| 5,993,787 A | 11/1999 | Sun et al. | |
| 6,017,920 A | 1/2000 | Kamishita et al. | |
| 6,083,518 A | 7/2000 | Lindahl | |
| 6,224,887 B1 | 5/2001 | Samour et al. | |
| 6,391,879 B1 | 5/2002 | Reeves | |
| 6,585,963 B1 | 7/2003 | Quan et al. | |
| 6,750,291 B2 | 6/2004 | Kim et al. | |
| 7,074,392 B1 | 7/2006 | Friedman et al. | |
| 7,588,753 B2 * | 9/2009 | Ferrandis et al. | 424/61 |
| 8,058,303 B2 | 11/2011 | Miki et al. | |
| 2004/0213744 A1 | 10/2004 | Lulla et al. | |
| 2005/0013836 A1 | 1/2005 | Raad | |
| 2005/0232879 A1 | 10/2005 | Sasagawa et al. | |
| 2005/0232981 A1 | 10/2005 | Ben-Sasson | |
| 2005/0276842 A1 | 12/2005 | Zhang et al. | |
| 2006/0292223 A1 | 12/2006 | Woolfson et al. | |
| 2007/0036731 A1 | 2/2007 | Hirsh et al. | |
| 2007/0071711 A1 | 3/2007 | Vromen | |
| 2007/0190124 A1 | 8/2007 | Zhang et al. | |
| 2007/0196325 A1 | 8/2007 | Zhang et al. | |
| 2007/0280972 A1 | 12/2007 | Zhang et al. | |
| 2007/0292355 A1 | 12/2007 | Tamarkin et al. | |
| 2008/0159984 A1 | 7/2008 | Ben-Sasson | |
| 2008/0193508 A1 | 8/2008 | Cohen et al. | |
| 2008/0220103 A1 * | 9/2008 | Birnbaum et al. | 424/735 |
| 2009/0030059 A1 | 1/2009 | Miki et al. | |
| 2009/0053290 A1 | 2/2009 | Sand et al. | |
| 2009/0076109 A1 | 3/2009 | Miki et al. | |
| 2009/0088434 A1 | 4/2009 | Mayer | |
| 2009/0137651 A1 | 5/2009 | Kobayashi et al. | |
| 2009/0162443 A1 * | 6/2009 | Anthony et al. | 424/489 |
| 2009/0175810 A1 | 7/2009 | Winckle et al. | |
| 2009/0202602 A1 | 8/2009 | Ishima et al. | |
| 2009/0247529 A1 | 10/2009 | Lindahl et al. | |
| 2009/0258070 A1 | 10/2009 | Burnier et al. | |
| 2010/0168200 A1 | 7/2010 | Masuda et al. | |
| 2010/0173965 A1 | 7/2010 | Masuda et al. | |
| 2010/0204293 A1 | 8/2010 | Masuda et al. | |
| 2010/0249202 A1 | 9/2010 | Koga et al. | |
| 2012/0014893 A1 | 1/2012 | Kobayashi et al. | |
| 2012/0022120 A1 | 1/2012 | Kobayashi et al. | |

FOREIGN PATENT DOCUMENTS

| | | |
|---|---|---|
| EP | 2005958 A1 | 12/2008 |
| EP | 2005958 A4 | 12/2008 |
| JP | 02-275877 A2 | 9/1990 |
| JP | 7277975 A2 | 10/1995 |
| JP | 2951725 B * | 9/1999 |
| JP | 2001-064206 A2 | 3/2001 |
| JP | 2002-114680 A2 | 4/2002 |
| WO | WO-88/06884 A1 | 9/1988 |
| WO | WO-96/11710 A1 | 4/1996 |
| WO | WO-2005/099764 A1 | 10/2005 |
| WO | WO-2006/038317 A1 | 4/2006 |

(Continued)

OTHER PUBLICATIONS

Brown, M.B. et al. (2009, e-published Nov. 24, 2008). "Overcoming the Nail Barrier: A Systematic Investigation of Ungual Chemical Penetration Enhancement," *Int'l J. Pharmaceutics*, 370, 61-67.

Dahdah, M.J. et al. (2006). "Onychomycosis-An Overview," *U.S. Dermatology Review* 1-4.

Deberker, D. (May 14, 2009). "Fungal Nail Disease," *N. Engl. J. Med*. 360(20):2108-16.

Drake, L.A. et al. (Jan. 1996). "Guidelines of Care for Superficial Mycotic Infections of the Skin: Onychomycosis," *Journal of the American Academy of Dermatology* 34(1)116-121.

(Continued)

*Primary Examiner* — Sreeni Padmanabhan
*Assistant Examiner* — Layla Sorush
(74) *Attorney, Agent, or Firm* — Morrison & Foerster LLP

(57) ABSTRACT

Provided herein are compositions and formulations comprising an antifungal agent. Pharmaceutical compositions comprising luliconazole in an amount effective for the treatment of onychomycosis are provided. Also provided are methods for treating dermatomycoses and onychomycosis using the compositions and formulations.

22 Claims, 7 Drawing Sheets

FOREIGN PATENT DOCUMENTS

| | | | |
|---|---|---|---|
| WO | WO-2007/054818 | A2 | 5/2007 |
| WO | WO-2007/054818 | A3 | 5/2007 |
| WO | WO-2007/070643 | A2 | 6/2007 |
| WO | WO-2007/070643 | A3 | 6/2007 |
| WO | WO-2007/070694 | A2 | 6/2007 |
| WO | WO-2007/070694 | A3 | 6/2007 |
| WO | WO-2007/077806 | A1 | 7/2007 |
| WO | WO-2007/098591 | A2 | 9/2007 |
| WO | WO-2007/098591 | A3 | 9/2007 |
| WO | WO-2009/028495 | A1 | 3/2009 |
| WO | WO-2009/053741 | A2 | 4/2009 |
| WO | WO-2011/073392 | A1 | 6/2011 |

OTHER PUBLICATIONS

Elewski, B.E., (Jul. 1998). "Onychomycosis: Pathogenesis, Diagnosis, and Management," *Clinical Microbiology Reviews* 11(3):415-429.

Gupchup, G. (Nov./Dec. 1999). "Structural Characteristics and Permeability Properties of the Human Nail: A Review," *J Cosmet. Sci.* 50:363-385).

Gupta, A.K. et al. (Sep. 2010). "Onychomycosis Therapy: Past, Present, Future," *J. Drugs in Dermatology* 9(9): 1109-1113.

International Preliminary Report on Patentability mailed on Aug. 16, 2011, for PCT Application No. PCT/US2010/024193, filed on Feb. 12, 2010, 6 pages.

International Search Report mailed on Apr. 6, 2010, for PCT Application No. PCT/US2010/024193, filed on Feb. 12, 2010, 3 pages.

Khengar, R.H. et al. (Dec. 2007). "Nail Swelling as a Pre-Formulation Screen for the Selection and Optimisation of Ungual Penetration Enhancers," *Pharmaceutical Research* 24(12):2207-2212.

Koga, H. et al. (Jun. 2006). "Luliconazole, a Novel Topical Imidazole: Results of the Preclinical Studies," *ISHAM*, P-0090.

Koga, H. et al. (May 2009). "The Durable Effect of Luliconazole in a Guinea Pig Tinea Pedis Model," *ISHAM*, Abstract PP-03-51, p. 362.

Koga, H. et al. (Sep. 2009). "In Vitro Antifungal Activities of Luliconazole, a New Topical Imdazole," *Med. Mycology* 47:640-647.

Novartis Pharmaceuticals Corporation (Nov. 2005). "Lamisil," 8 pages.

Medical News Today (Mar. 21, 2008) "Interim Anaylsis of Phase 2 Clinical Trial in Onychomycosis (Topical Lotion for Nail Fungus)," located at <http://www.medicalnewstoday.com/printerfriendlynews.php?newsid=101286>, last visited on Mar. 5, 2012, 3 pages.

Niwano, Y. et al. (Apr. 1998). "In Vitro and In Vivo Antidermatophyte Activities of NND-502, a Novel Optically Active Imidazole Antimycotic Agent," Antimicrob. Agents Chemother. 42(4):967-970.

Osborne, C., (Apr. 2004). "Antifungal Drug Response in an In Vitro Model of Dermatophyte Nail Infection," *Medical Mycology* 42(2):159-163.

Dermik Laboratories (Jan. 2005). "Penlac Nail Lacquer," 2 pages.

Janssen Pharmaceutica N.V. (2001). "Sporanox (Itraconazole) Capsules," located at <http://www.orthobiotech.com/orthobiotech/assets/Sporanox_Oral.pdf>, last visited on Mar. 5, 2012, 28 pages.

Topica Pharmaceuticals (Jan. 11, 2011). "Topica Announces Enrollment of First Patient in Phase 1/2a Trail of Luliconazole for Treating Onychomycosis," located at <http://clinicaltrials.gov/ct2/show/NCT01044381?term=topica+pharmaceuticals&rank=1>, last visited on Mar. 5, 2012, 2 pages.

Topica Pharmaceuticals (Jun. 20, 2011). "Topica Announces Positive Results from Phase 1/2a Trail of Luliconazole for Treatment of Onychomycosis," located at <http://www.topicapharma.com>, last visited on Mar. 5, 2012, 2 pages.

Written Opinion mailed on Apr. 6, 2010, for PCT Application No. PCT/US2010/024193, filed on Feb. 12, 2010, 5 pages.

\* cited by examiner

Figure 1

A. Summary of Dermal Irritation Scores: Erythema and Eschar – MALE

| Endpoint | Study Interval (Day) | 0 mg/site/day Abraded | | | 0 mg/site/day Intact | | | 12.5 mg/site/day Abraded | | | 12.5 mg/site/day Intact | | |
|---|---|---|---|---|---|---|---|---|---|---|---|---|---|
| | | Mean | SD | N | Mean | SD | N | Mean | SD | N | Mean | SD | N |
| Dermal Irritation Scores | 1 | 0.0 | 0.00 | 7 | 0.0 | 0.00 | 7 | 0.3 | 0.49 | 7 | 0.1 | 0.38 | 7 |
| | 2 | 0.7 | 0.49 | 7 | 0.6 | 0.53 | 7 | 0.6 | 0.53 | 7 | 0.6 | 0.53 | 7 |
| | 3 | 0.9 | 0.38 | 7 | 0.9 | 0.38 | 7 | 0.9 | 0.38 | 7 | 0.9 | 0.38 | 7 |
| | 4 | 1.0 | 0.00 | 7 | 1.0 | 0.00 | 7 | 1.0 | 0.00 | 7 | 1.0 | 0.00 | 7 |
| | 5 | 1.3 | 0.49 | 7 | 1.1 | 0.38 | 7 | 1.1 | 0.38 | 7 | 1.1 | 0.38 | 7 |
| | 6 | 1.1 | 0.38 | 7 | 1.1 | 0.38 | 7 | 1.3 | 0.49 | 7 | 1.0 | 0.00 | 7 |
| | 7 | 1.1 | 0.38 | 7 | 1.1 | 0.38 | 7 | 1.6 | 0.53 | 7 | 1.0 | 0.00 | 7 |
| | 14 | 1.1 | 0.38 | 7 | 1.0 | 0.00 | 7 | 1.1 | 0.38 | 7 | 1.0 | 0.00 | 7 |
| | 21 | 1.0 | 0.00 | 7 | 1.0 | 0.00 | 7 | 1.0 | 0.00 | 7 | 1.0 | 0.00 | 7 |
| | 28 | 0.6 | 0.53 | 7 | 0.6 | 0.53 | 7 | 1.0 | 0.00 | 7 | 1.0 | 0.00 | 7 |

B. Summary of Dermal Irritation Scores: Erythema and Eschar MALE

| Endpoint | Study Interval (Day) | Untreated Abraded | | | Untreated Intact | | |
|---|---|---|---|---|---|---|---|
| | | Mean | SD | N | Mean | SD | N |
| Dermal Irritation Scores | 1 | 0.0 | 0.00 | 7 | 0.0 | 0.00 | 7 |
| | 2 | 0.0 | 0.00 | 7 | 0.0 | 0.00 | 7 |
| | 3 | 0.0 | 0.00 | 7 | 0.0 | 0.00 | 7 |
| | 4 | 0.0 | 0.00 | 7 | 0.0 | 0.00 | 7 |
| | 5 | 0.0 | 0.00 | 7 | 0.0 | 0.00 | 7 |
| | 6 | 0.0 | 0.00 | 7 | 0.0 | 0.00 | 7 |
| | 7 | 0.0 | 0.00 | 7 | 0.0 | 0.00 | 7 |
| | 14 | 0.0 | 0.00 | 7 | 0.0 | 0.00 | 7 |
| | 21 | 0.0 | 0.00 | 7 | 0.0 | 0.00 | 7 |
| | 28 | 0.0 | 0.00 | 7 | 0.0 | 0.00 | 7 |

Figure 2

A. Summary of Dermal Irritation Scores: Edema – MALE

| Endpoint | Study Interval (Day) | 0 mg/site/day Abraded | | | 0 mg/site/day Intact | | | 12.5 mg/site/day Abraded | | | 12.5 mg/site/day Intact | | |
|---|---|---|---|---|---|---|---|---|---|---|---|---|---|
| | | Mean | SD | N | Mean | SD | N | Mean | SD | N | Mean | SD | N |
| Dermal Irritation Scores | 1 | 0.0 | 0.00 | 7 | 0.0 | 0.00 | 7 | 0.0 | 0.00 | 7 | 0.0 | 0.00 | 7 |
| | 2 | 0.0 | 0.00 | 7 | 0.0 | 0.00 | 7 | 0.0 | 0.00 | 7 | 0.0 | 0.00 | 7 |
| | 3 | 0.0 | 0.00 | 7 | 0.0 | 0.00 | 7 | 0.0 | 0.00 | 7 | 0.0 | 0.00 | 7 |
| | 4 | 0.0 | 0.00 | 7 | 0.0 | 0.00 | 7 | 0.0 | 0.00 | 7 | 0.0 | 0.00 | 7 |
| | 5 | 0.1 | 0.38 | 7 | 0.0 | 0.00 | 7 | 0.1 | 0.38 | 7 | 0.0 | 0.00 | 7 |
| | 6 | 0.1 | 0.38 | 7 | 0.0 | 0.00 | 7 | 0.0 | 0.00 | 7 | 0.0 | 0.00 | 7 |
| | 7 | 0.0 | 0.00 | 7 | 0.0 | 0.00 | 7 | 0.0 | 0.00 | 7 | 0.0 | 0.00 | 7 |
| | 14 | 0.0 | 0.00 | 7 | 0.0 | 0.00 | 7 | 0.0 | 0.00 | 7 | 0.0 | 0.00 | 7 |
| | 21 | 0.0 | 0.00 | 7 | 0.0 | 0.00 | 7 | 0.0 | 0.00 | 7 | 0.0 | 0.00 | 7 |
| | 28 | 0.0 | 0.00 | 7 | 0.0 | 0.00 | 7 | 0.0 | 0.00 | 7 | 0.0 | 0.00 | 7 |

B. Summary of Dermal Irritation Scores: Edema – MALE

| Endpoint | Study Interval (Day) | Untreated Abraded | | | Untreated Intact | | |
|---|---|---|---|---|---|---|---|
| | | Mean | SD | N | Mean | SD | N |
| Dermal Irritation Scores | 1 | 0.0 | 0.00 | 7 | 0.0 | 0.00 | 7 |
| | 2 | 0.0 | 0.00 | 7 | 0.0 | 0.00 | 7 |
| | 3 | 0.0 | 0.00 | 7 | 0.0 | 0.00 | 7 |
| | 4 | 0.0 | 0.00 | 7 | 0.0 | 0.00 | 7 |
| | 5 | 0.0 | 0.00 | 7 | 0.0 | 0.00 | 7 |
| | 6 | 0.0 | 0.00 | 7 | 0.0 | 0.00 | 7 |
| | 7 | 0.0 | 0.00 | 7 | 0.0 | 0.00 | 7 |
| | 14 | 0.0 | 0.00 | 7 | 0.0 | 0.00 | 7 |
| | 21 | 0.0 | 0.00 | 7 | 0.0 | 0.00 | 7 |
| | 28 | 0.0 | 0.00 | 7 | 0.0 | 0.00 | 7 |

Figure 3

A. Summary of Dermal Irritation Scores: Erythema and Eschar – MALE

| Endpoint | Study Interval (Day) | 0 mg/site/day Abraded | | | 0 mg/site/day Intact | | | 12.5 mg/site/day Abraded | | | 12.5 mg/site/day Intact | | |
|---|---|---|---|---|---|---|---|---|---|---|---|---|---|
| | | Mean | SD | N | Mean | SD | N | Mean | SD | N | Mean | SD | N |
| Dermal Irritation Scores | 35 | 0.0 | 0.00 | 3 | 0.0 | 0.00 | 3 | 0.3 | 0.58 | 3 | 0.3 | 0.58 | 3 |
| | 42 | 0.0 | 0.00 | 3 | 0.0 | 0.00 | 3 | 0.0 | 0.00 | 3 | 0.0 | 0.00 | 3 |

B. Summary of Dermal Irritation Scores: Erythema and Eschar – MALE

| Endpoint | Study Interval (Day) | Untreated Abraded | | | Untreated Intact | | |
|---|---|---|---|---|---|---|---|
| | | Mean | SD | N | Mean | SD | N |
| Dermal Irritation Scores | 35 | 0.0 | 0.00 | 3 | 0.0 | 0.00 | 3 |
| | 42 | 0.0 | 0.00 | 3 | 0.0 | 0.00 | 3 |

C. Summary of Dermal Irritation Scores: Edema – MALE

| Endpoint | Study Interval (Day) | 0 mg/site/day Abraded | | | 0 mg/site/day Intact | | | 12.5 mg/site/day Abraded | | | 12.5 mg/site/day Intact | | |
|---|---|---|---|---|---|---|---|---|---|---|---|---|---|
| | | Mean | SD | N | Mean | SD | N | Mean | SD | N | Mean | SD | N |
| Dermal Irritation Scores | 35 | 0.0 | 0.00 | 3 | 0.0 | 0.00 | 3 | 0.0 | 0.00 | 3 | 0.0 | 0.00 | 3 |
| | 42 | 0.0 | 0.00 | 3 | 0.0 | 0.00 | 3 | 0.0 | 0.00 | 3 | 0.0 | 0.00 | 3 |

D. Summary of Dermal Irritation Scores: Edema – MALE

| Endpoint | Study Interval (Day) | Untreated Abraded | | | Untreated Intact | | |
|---|---|---|---|---|---|---|---|
| | | Mean | SD | N | Mean | SD | N |
| Dermal Irritation Scores | 35 | 0.0 | 0.00 | 3 | 0.0 | 0.00 | 3 |
| | 42 | 0.0 | 0.00 | 3 | 0.0 | 0.00 | 3 |

ANTI-FUNGAL FORMULATION

CROSS-REFERENCE TO RELATED APPLICATIONS

This application is a continuation of U.S. application Ser. No. 12/705,555, filed on Feb. 12, 2010, which claims the benefit of U.S. Provisional Patent Application Nos. 61/152,658, filed Feb. 13, 2009 and 61/162,661, filed Mar. 23, 2009, the disclosures of which are incorporated herein by reference in their entireties.

FIELD OF THE INVENTION

The present application relates to pharmaceutical compositions and formulations that may be used for anti-fungal treatments including, but not limited to, dermatomycoses and onychomycosis.

BACKGROUND OF THE INVENTION

A number of imidazole antimycotic agents are under investigation or are used for the treatment of dermatomycoses (an infection of the skin caused by dermatophytes or other fungi) or onychomycosis (a fungal infection of the nail plate and/or nail bed). One such antimycotic agent approved and launched in Japan for cutaneous mycosis such as Tinea pedis, tinea corporis and tinea cruris as well as Candidiasis and Tinea versicolor infection is luliconazole (Lulicon® Cream and Solution 1%).

The compound luliconazole is represented by the formula (I):

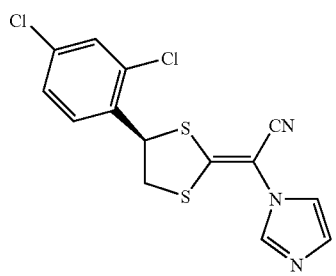

Luliconazole is a compound screened from analogues of its predecessor lanoconazole, which has been clinically used for the treatment of dermatomycoses. It is believed that luliconazole produces its antifungal effect by inhibiting the synthesis of ergosterol, which is a constituent of the cell membrane of fungi. The antifungal activity of luliconazole was recently tested against clinically important dermatomycotic fungi and compared to other representative antifungal reference drugs. Luliconazole demonstrated greater potency against *Trichophyton rubrum, Trichophyton mentagrophytes* and *Trichophyton tonsurans* than the reference drugs, such as allylamine (terbinafine), thiocarbamate (liranaftate), benzylamine (butenafine), morpholine (amorolfine), and azoles (ketoconazole, clotrimazole, neticonazole, miconazole and bifonazole). Koga et al., Med. Mycol. (2008) 1-8.

The concentration of luliconazole in a stable cream is found in the commercial product Lulicon® at 1% by weight. Creams and other liquid formulations containing luliconazole have been described as having about 0.5% to about 5% by weight luliconazole. See, e.g., U.S. Patent Publication Nos. US2009/0137651, published May 28, 2009; US2009/0076109, published Mar. 19, 2009; and US2009/0030059, published Jan. 29, 2009. Creams and other liquid formations containing greater than 5% luliconazole are known to be unstable and difficult to solubilize, resulting in crystallization or precipitation of the compound out of solution. Nonetheless, there remains a need for such formulations, e.g., for use in the treatment of dermatomycoses and onychomycosis.

Tinea pedis, also known as athlete's foot, is the most common of the dermatomycoses, affecting up to 10 percent of the general population. However, onychomycosis, which accounts for up to 50% of all nail diseases and affects approximately 35 million people in the U.S. alone, is much more difficult to treat than Tinea pedis, for several reasons, such as the site of infection, time required to regenerate healthy nail, and the composition of a nail as compared to the skin. Dandah, M. J. et al., (2006) U.S. Dermatology Review 1-4. As a result, formulations that are sufficient in the treatment of Tinea pedis are not generally sufficient for the treatment of onychomycosis.

The site of fungal infection in onychomychosis makes its treatment particularly challenging. Distal subungual onychomycosis (DSO), which is the most common form of onychomycosis, is characterized by fungal invasion of the nail bed and underside of the nail plate beginning at the hyponychium. Clinical findings associated with DSO include nail discoloration (yellowing or other discoloration such as the presence of black or brown color), thickening, subungual debris and loss of attachment of the nail plate to the nail bed. The nail may also become friable and crumble away. DSO can cause extreme nail disfigurement and often results in pain. Treatment of the infected region with a topical pharmaceutical composition requires the composition to deliver a therapeutically effective amount of the active agent through the nail in order to reach the site of infection. The only U.S. Food and Drug Agency approved topical treatment for onychomycosis is ciclopirox (Penlac®, Dermik) an 8% topical solution applied as a nail lacquer. In De Berker, N. Engl. J. Med. (2009) 360: 2108-16, the mycologic cure for DSO using Penlac daily for 48 weeks was reported to be 28 to 36%. However, a clear nail was achieved in only 7% of cases. Amorolfine (Loceryl®, Galderma) is another topical therapy that has long treatment times and low cure rates, likely as a result of poor drug penetration through the nail. De Berker, supra. Topical therapeutics for onychomycosis thus fail to provide optimal treatment of the infection site. Orally administered drugs are an alternative to topical treatments for onychomycosis, but have their own disadvantages, including prolonged systemic exposure to an active agent when only a specific site is infected. Ketoconazole (Nizoral®, Janssen-Cilag) was the first oral imidazole introduced for the treatment of onychomycosis in the 1980s. However, due to hepatotoxicity its use is now restricted to nail infections that have failed to respond to other therapies. Griseofulvin (Grisovin®, Glaxo Welcome) is an oral therapeutic that has been available since the 1950s which results in low cure and high relapse rates. Elewski, B. E., Clinical Microbiology Reviews (1998) 11:415-429. The newer oral anti-fungals, terbinafine (Lamisil®) and itraconazole (Sporanox®) are effective in the treatment of onychomycosis with mycological cure rates of 70-80% and treatment periods of 12-16 weeks. However, even in the newer oral anti-fungals, the percentage of patients exhibiting both mycological cure and clinical cure remain low. For example, in a study of patients being treated for onychomycosis of the toenail with Lamisil®, only 38% of patients treated demonstrated both mycological cure (simultaneous occurrence of negative KOH plus negative culture) and clinical cure (0% nail involvement). See Lamisil® Package Insert. In a study of patients being treated for onychomycosis of the toenail with Sporanox®, only 14% of patients treated demonstrated both mycological cure and clinical cure. See Sporanox® Package Insert. These drugs also have significant side effects and interact with many medications, which limits their use. For example, liver failure requiring liver transplant or resulting in death have occurred in patients, with and without preexisting liver disease, taking oral Lamisil® for the treatment of onychomycosis. In addition, Lamisil® is known to inhibit CYP450 2D6 isozyme. Drugs that are predominately metabolized by the CYP450 2D6 isozyme include tricyclic antidepressants, selective serotonin reuptake inhibitors, beta-blockers, antiarrhyhmics class 1C and monoamino oxidase inhibitors type B, and individuals who are taking one or more of these medications concurrently with Lamisil® must be carefully monitored and may require a reduction in dosage of such drugs. Sporanox® has been associated with cases of serious hepatotoxicity, including liver failure and death, with certain instances occurring in individuals having neither pre-existing liver disease or a serious underlying medical condition. Sporanox®, which is an inhibitor of CYP3A4, is also contraindicated in patients with evidence of ventricular dysfunction, such as patients with congestive heart failure and in patients taking cisapride, pimozide, levacetylmethadol (levomethadyl), or quinidine concomitantly with Sporanox® and/or other CYP3A4 inhibitors. Thus, oral therapies do not provide sufficient or effective cure rates, are associated with series adverse side affects and limited in their application. A significant unmet medical need remains for an effective treatment of onychomycosis. A treatment that has fewer and/or less severe side effects than those associated with current therapies would be particularly beneficial.

Since some onychomycosis infections may require up to a year of treatment for healthy, non-infected nail to fully regrow, the active agent must be present at the infected site in therapeutic concentrations long enough to effect a cure. Such agents should also prevent relapse and re-infection after discontinuation of therapy, have minimal side effects and exhibit an acceptable safety profile. Chronic administration of either a topical or oral treatment is therefore required, and will typically last for the period of time required for new, healthy nail to regrow, which can vary on an individual basis. Treatment periods for onychomycosis generally start at several weeks to several months long and last up to a year. Chronic administration of a topical or oral antifungal drug presents unique toxicity concerns. For example, even if an active agent is deemed safe for chronic use, its topical administration must be carried out in a manner that formulates the active agent at a desired concentration and where the carrier itself is safe for chronic administration to the nail. Chronic administration of a topical composition also requires patient compliance, which can be compromised if the treatment regimen is difficult or otherwise undesirable. For example, patient compliance in the treatment of onychomycosis is more likely to be compromised if the pharmaceutical composition has any one or more of the following features: is sticky or has an unpleasant texture, irritates the nail or surrounding skin, leaves an uncomfortable film on the nail, is messy to apply (e.g., when its application results in 'run-off' in which the composition does not stay on the nail and uncontrollably rolls or seeps off the nail and onto the surrounding skin), has a bad odor, requires periodic (e.g., weekly) removal of resulting film or lacquer, and the like. Thus, in the context of chronic administration of an active agent to the nail, the safety and performance characteristics of the pharmaceutical composition containing the active agent are highly important. Chronic administration of an oral drug also requires patient compliance. In addition, chronic administration of an oral drug in the treatment of onychomycosis results in prolonged systemic exposure to the active agent, which can have adverse health consequences such as undesired drug-drug interactions with existing medications and toxicity concerns, both of which can greatly limit use in a large portion of the patient population (e.g., in elderly patients who are more susceptible to onychomycosis and also who are more likely to be on a daily regimen of other pharmaceutical agents). Patients taking oral antifungal medications should also have periodic laboratory evaluations to monitor liver and blood cell function. Elewski, B. E., supra.

Onychomycosis affects toenails substantially more than fingernails and toenails are approximately twice as thick as fingernails. The reported prevalence of toenail onychomycosis in the Western adult population is approximately 14% and increases with age. De Berker, supra. The nail plate, through which an active agent must travel to reach the site of onychomycosis infection, is dense and hard. In addition, the nail plate of a toenail is substantially thicker than the nailplate of a fingernail, providing a formidable barrier to the nail bed. In contrast to Tinea pedis treatment, in which the active agent has to pass the thin, elastic and pliable Stratum coreum (the outermost layer of the epidermis) of the skin, treatment of onychomycosis requires an active agent to pass through the hard, dense and thick nail plate of a fingernail or toenail. The natural barrier of a nail provides a harsher environment and a much longer diffusion pathway for drug delivery as compared to treatment applications that only need to penetrate the Stratum coreum of the skin, with toenails having about twice the diffusion pathway of fingernails. The physical and chemical differences between the nail and the Stratum coreum account for the unique treatment challenges for fungal infections involving the nail, especially the toenail, which are not shared by fungal infections of the skin.

Factors that contribute to the development of onychomycosis include advanced age, diabetes (which reduces circulation to the extremities), history of prior infection, wearing heat- and moisture-retaining footwear, communal bathing, immunosuppression (e.g., HIV infection, the use of antibiotics or immunosuppressive drugs), trauma to the nail, use of insufficiently cleaned manicure tools, poor overall health, and warm climates.

It is estimated that about half of those affected with onychomycosis are not receiving treatment. Medical News Today, Mar. 21, 2008. However, it is important to treat onychomycosis, as it is an infection and does not resolve spontaneously. The infection may worsen, spread to other uninfected locations (e.g., other nails or to the surrounding skin) or infect other individuals. Onychomycosis infections can greatly affect an individual's quality of life and cause pain and morbidity. Infections of the fingernails, which are plainly visible, may be cosmetically unacceptable and result in embarrassment, emotional distress, loss of self-esteem, anxiety and depression. Individuals with moderate to severe onychomycosis may experience limits in manual performance and ambulation, loosing their ability to perform many routine tasks.

Current therapies do not sufficiently or effectively meet the challenges presented by onychomycosis. Existing topical therapies for onychomycosis have low mycologic cure rates and poor complete cure rates. They can also be inconvenient to the user, requiring the daily application of a nail laquer and weekly removal of the resulting film. Oral therapies for onychomycosis are assoicated with higher mycologic cure rates than existing topical therapies, but these drugs exhibit poor cure rates, are contraindicated in numerous patient populations and have been associated with severe, and even deadly, side effects. Due to the low cure rates and significant drawbacks to existing therapies, the development of new topical treatments for onychomycosis is desired. A topical treatment that results in high cure rates, provides a clear nail, has minimal side effects, and is associated with high patient compliance, is particularly desired. An effective topical treatment for onychomycosis preferably addresses each of the challenges presented by onychomycosis. The compositions and formulations described herein provide a significant solution to this problem and provide additional benefits as provided herein.

The foregoing examples of the related art and limitations are intended to be illustrative and not exclusive. Other limitations of the related art will become apparent to those of skill in the art upon a reading of the specification as provided herein.

SUMMARY OF THE INVENTION

In one embodiment of the application, there is provided a stable pharmaceutical composition comprising a luliconazole type antifungal agent or a pharmaceutically acceptable salt thereof wherein the antifungal agent comprises greater than about 5% by weight of the composition. In one aspect, the antifungal agent is greater than about 7% by weight of the composition. In another aspect, the antifungal agent is greater than about 10% by weight of the composition. In yet another aspect, the antifungal agent is from about 5% to about 12.5% by weight of the composition. In one aspect, a pharmaceutical composition described herein comprises luliconazole in about 5 weight percent to about 15 weight percent or from about 8 weight percent to about 15 weight percent or from about 10 weight percent to about 15 weight percent or from about 12 weight percent to about 15 weight percent or from about 5 weight percent to about 12 weight percent or from about 5 weight percent to about 10 weight percent or from about 5 weight percent to about 8 weight percent or from about 8 weight percent to about 12 weight percent or from about 9 weight percent to about 11 weight percent. In another aspect, a pharmaceutical composition comprises luliconazole in at least about or about any of 5 or 8 or 10 or 12 or 15 weight percent.

In one particular aspect, the compositions provided herein are stable for at least 4 weeks. In another aspect, the compositions are stable for at least 4 weeks at a temperature of about 4° C. The luliconazole compositions provided herein may exhibit any one or more of the following attributes: (i) the composition remains as a clear solution without evidence of crystal formation upon visual inspection after any of 1 or 2 or 3 or 4 or 5 or 6 or 12 or 18 or 24 months or more of storage at any of 5° C., 25° C. and 40° C.; (ii) the composition contains at least about any of 80% or 85% or 90% or 95% of the theoretical maximum amount of luliconazole after 2 or 4 or 6 months of storage at any of 5° C., 25° C. and 40° C.; (iii) the composition contains no more than any of 0.2 or 0.3 or 0.5 or 0.75 or 1 weight percent of the Z form of luliconazole after any of 1 or 2 or 3 or 4 or 5 or 6 or 12 or more months of storage at any of 5° C., 25° C. and 40° C.; (iv) the composition contains no more than any of 0.2 or 0.3 or 0.5 or 0.75 or 1 or 2 or 3 or 4 or 5 weight percent of the SE form of luliconazole after any of 1 or 2 or 3 or 4 or 5 or 6 or 12 or more months of storage at any of 5° C., 25° C. and 40° C.; (v) the composition contains no more than any of 0.5, or 1 or 2 or 3 or 4 or 5 combined weight percent of the Z and SE forms of luliconazole after any of 1 or 2 or 3 or 4 or 5 or 6 or 12 or more months of storage at any of 5° C., 25° C. and 40° C.; and (vi) the composition contains at least about any of 80% or 90% or 100% or 110% label of luliconazole after any of 1 or 2 or 3 or 4 or 5 or 6 or 12 or more months of storage at any of 5° C., 25° C. and 40° C.

In another aspect, the compositions provided herein comprise at least one excipient, or alternatively at least two excipients, or alternatively at least three excipients selected from the group consisting of an alcohol, a ketone, a polar aprotic solvent and an ethylene glycol derivative. In another aspect, the alcohol is benzyl alcohol, ethanol or a combination thereof. In yet another aspect, the ketone is acetone. In yet another aspect, the polar aprotic solvent is propylene carbonate. In still yet another aspect, the ethylene glycol derivative is diethylene glycol monoethyl ether (such as Transcutol™ P). In one aspect, the ethanol is from about 35% to about 60% by weight of the composition. In another aspect, the benzyl alcohol is from about 1% to about 15% by weight of the composition. In another aspect, the acetone is from about 5% to about 15% by weight of the composition. In yet another aspect, the diethylene glycol monoethyl ether (such as Transcutol™ P) is from about 5% to about 30% by weight of the composition.

In another aspect, the compositions provided herein comprise 10% active agent, 2% benzyl alcohol, 12% acetone and 25% diethylene glycol monoethyl ether (such as Transcutol™ P). In another aspect, the compositions provided herein comprise 12.5% active agent, 4% benzyl alcohol, 12% acetone and 25% diethylene glycol monoethyl ether (such as Transcutol™ P). In yet another aspect, the compositions provided herein further comprise a film-forming agent, such as, but not limited to methylvinyl ether-maleic anhydride (Gantrez). In still yet another aspect, the compositions provided herein are formulated as a gel or cream for topical administration.

In one aspect of the above, the antifungal agent is luliconazole of the formula:

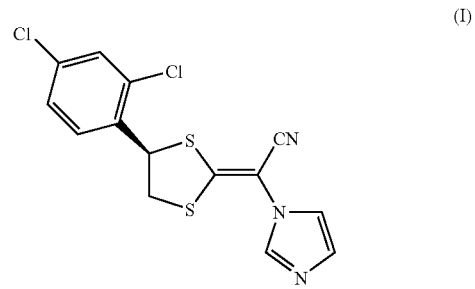

(I)

or a pharmaceutically acceptable salt thereof.

Luliconazole in the compositions described herein may be present in substantially pure form (e.g., the composition contains no more than 15% or preferably no more than 10% or more preferably no more than 5% or even more preferably no more than 3% and most preferably no more than 1% impurity, which impurity in one aspect is a different stereochemical form of luliconazole, such as the Z or SE forms of luliconazole) or may also be present in the context of a racemic or other mixture, e.g., together with the Z or SE forms of luliconazole.

In one embodiment, the invention provides for a pharmaceutical composition comprising about 5 weight percent to about 15 weight percent luliconazole, an alcohol, a ketone and a polar aprotic solvent. In one aspect, the alcohol is benzyl alcohol or ethanol. In another aspect, the ketone is acetone. In a further aspect, the polar aprotic solvent is propylene carbonate. In a particular variation, the composition comprises two alcohols, which in one embodiment are benzyl alcohol and ethanol. In one aspect, the composition may further comprises an ethylene glycol derivative, such as an ethylene glycol derivative of the formula HOCH$_2$CH$_2$OCH$_2$CH$_2$OR where R is an alkyl group having 1 to 6 carbon atoms. Thus, in one aspect the ethylene glycol derivative is diethyleneglycol monoethyl ether.

In another embodiment, the invention provides for a pharmaceutical composition comprising luliconazole, an ethylene glycol derivative and at least two of an alcohol, a ketone, and a polar aprotic solvent. In one aspect, the alcohol is benzyl alcohol or ethanol. In another aspect, the ketone is acetone. In a further aspect, the polar aprotic solvent is propylene carbonate. In a particular variation, the composition comprises two alcohols, which in one embodiment are benzyl alcohol and ethanol. In one aspect, the composition comprises at least two of benzyl alcohol, acetone, propylene carbonate and ethanol. In another aspect, the composition comprises at least three of benzyl alcohol, acetone, propylene carbonate and ethanol. In one such variation, the composition comprises benzyl alcohol, acetone and propylene carbonate and wherein the ethylene glycol derivative, acetone and propylene carbonate when taken together account for about 40 weight percent to about 45 weight percent of the composition. In another embodiment, the composition comprises at least four of benzyl alcohol, acetone, propylene carbonate, ethanol and where the an ethylene glycol derivative is of the formula HOCH$_2$CH$_2$OCH$_2$CH$_2$OR where R is an alkyl group having 1 to 6 carbon atoms. Thus, in one aspect the ethylene glycol derivative is diethyleneglycol monoethyl ether.

In any of the preceding embodiments, in one aspect the composition comprises 0.01 weight percent to about 5 weight percent benzyl alcohol. In another aspect of such embodiments, the composition comprises about 8 weight percent to about 15 weight percent luliconazole. In a further aspect of such embodiments, the composition further comprises a film forming agent in from 0.01 weight percent to about 4 weight percent. In one aspect, the film-forming agent is a maleic anhydride/methyl vinyl ether copolymer, which in a particular variation is Gantrez® ES-425.

In any of the preceding embodiments, in one aspect the composition is substantially anhydrous.

In any of the preceding embodiments, in one aspect the composition is a clear solution without evidence of crystal formation upon visual inspection after 6 months of storage at any of 5° C., 25° C. and 40° C.

In any of the preceding embodiments, in one aspect the composition comprises at least about 95% of the theoretical maximum amount of luliconazole after 6 months of storage at any of 5° C., 25° C. and 40° C.

In any of the preceding embodiments, in one aspect the composition is a clear solution without evidence of crystal formation upon visual inspection after 6 months of storage at any of 5° C., 25° C. and 40° C. and wherein the composition contains at least about 95% of the theoretical maximum amount of luliconazole after 6 months of storage at any of 5° C., 25° C. and 40° C.

In any of the preceding embodiments, in one aspect the composition eradicates at least 80% of a fungal infection of the nail after 14 days of treatment, as measured by the recovery of less than 20% of the theoretical amount of recoverable ATP from the fungus.

In any of the preceding embodiments, in one aspect the composition is a clear solution without evidence of crystal formation upon visual inspection after 6 months of storage at any of 5° C., 25° C. and 40° C. and wherein the composition contains at least about 95% of the theoretical maximum amount of luliconazole after 6 months of storage at any of 5° C., 25° C. and 40° C.

In any of the preceding embodiments, in one aspect the composition is provided wherein at least 50 μg/cm$^2$ of luliconazole penetrates through a 0.5 mm thick nail when 1 μL the composition is applied to the nail once daily for 3 days.

In any of the preceding embodiments, in one aspect the composition is free of an alpha-hydroxycarboxylic acid, NMP and crotamiton. In any of the preceding embodiments, in one aspect the composition dries in less than about 5 minutes after application to a nail.

Also provided is a pharmaceutical composition, comprising: from about 5 weight percent to about 15 weight percent luliconazole; from about 5 weight percent to about 25 weight percent acetone; from about 1 weight percent to about 15 weight percent propylene carbonate; from about 15 weight percent to about 35 weight percent of an ethylene glycol derivative of the formula HOCH$_2$CH$_2$OCH$_2$CH$_2$OR where R is an alkyl group having 1 to 6 carbon atoms; and from 0.01 weight percent to about 6 weight percent benzyl alcohol. In one aspect, R is ethyl. In another aspect, the composition comprises 2 weight percent to 4 weight percent benzyl alcohol. In a further aspect, the composition comprises a film forming agent in from 0.01 weight percent to about 4 weight percent. In one variation, the film-forming agent is a maleic anhydride/methyl vinyl ether copolymer, such as the film forming agent Gantrez® ES-425. In one variation, the composition further comprises ethanol. In another variation, the composition comprises from about 35 weight percent to about 45 weight percent ethanol.

In a particular variation, a pharmaceutical composition is provided wherein the composition comprises from about 9 weight percent to about 12.5 weight percent luliconazole; from about 8 weight percent to about 15 weight percent acetone; from about 3 weight percent to about 8 weight percent propylene carbonate; from about 20 weight percent to about 30 weight percent of an ethylene glycol derivative of the formula HOCH$_2$CH$_2$OCH$_2$CH$_2$OR where R is an alkyl group having 1 to 6 carbon atoms; and benzyl alcohol from 0.01 weight percent to about 5 weight percent. In one such variation, R is ethyl. IN one aspect, the composition comprises about 2 weight percent to about 4 weight percent benzyl alcohol. In another aspect, the composition further comprises a film forming agent in from 0.01 weight percent to about 4 weight percent. In one variation, the film-forming agent is a maleic anhydride/methyl vinyl ether copolymer, such as the film forming agent is Gantrez® ES-425. In one variation, the composition further comprises ethanol. In another variation, the composition comprises from about 35 weight percent to about 45 weight percent ethanol.

In one variation, the composition comprises about 10 weight percent luliconazole. In another variation, the composition comprises about 12.5 weight percent luliconazole.

In a specific variation, a pharmaceutical composition is provided, wherein the composition comprises about 10 weight percent luliconazole; about 12 weight percent acetone; about 5 weight percent propylene carbonate; about 25 weight percent of an ethylene glycol derivative of the formula HOCH$_2$CH$_2$OCH$_2$CH$_2$OR where R is ethyl; and about 4 weight percent benzyl alcohol. In one such variation, the composition further comprises a film forming agent in about 1 weight percent. In on aspect, the film-forming agent is a maleic anhydride/methyl vinyl ether copolymer. In another aspect, the film forming agent is Gantrez® ES-425. In a further variation, the composition comprises ethanol.

Also provided is a method of treating onychomycosis in an individual in need thereof, comprising contacting the individual's nail with any of the preceding pharmaceutical compositions. In one aspect, the method is a method of treating distal subungual onychomycosis. In another aspect, the method is a method of treating onychomycosis of a toenail or fingernail. In one aspect, method comprises contacting the individual's nail with the composition once daily. In one variation, the individual is diabetic, is of an advanced age or is immunocompromised.

Also provided is a method of penetrating a nail with luliconazole in an individual in need thereof, comprising contacting the individual's nail with any of the preceding compositions. In one aspect, the method comprises administering a composition comprising at least about 10 weight percent luliconazole to the individual's nail once daily for at least three days. In one aspect, the nail is a toenail. In another aspect, the nail is a fingernail.

Methods for preparing a pharmaceutical composition comprising luliconazole are also described. In one aspect, the method comprises combining luliconazole with an ethylene glycol derivative, an alcohol, a ketone, a polar aprotic solvent. In one variation, the ethylene glycol derivative of the formula $HOCH_2CH_2OCH_2CH_2OR$ where R is an alkyl group having 1 to 6 carbon atoms. Thus, in one variation, the ethylene glycol derivative is diethyleneglychol monoethyl ether. In one aspect, the ketone is acetone. In another aspect, the polar aprotic solvent is propylene carbonate. In another aspect, the alcohol is benzyl alcohol or ethanol. In a particular variation, the composition comprises benzyl alcohol and ethanol.

Kits are also provided herein, such as kits comprising any of the preceding pharmaceutical compositions. In one aspect, the kit further comprises instructions for use in the treatment of onychomycosis, which in one aspect is distal subungual onychomycosis.

Articles of manufacture are also provided, such as articles of manufacture comprising a container in which any of the preceding pharmaceutical compositions is contained. In one aspect, the container is plastic. In another aspect, the container is a device. In a particular variation, the article of manufacture comprises a unit dosage form of the composition.

In one aspect, a pharmaceutical composition of luliconazole is provided, wherein the composition comprises from about 5 weight percent to about 15 weight percent luliconazole; from about 5 weight percent to about 25 weight percent acetone; from about 1 weight percent to about 15 weight percent propylene carbonate; from about 15 weight percent to about 35 weight percent of an ethylene glycol derivative, which in certain embodiments is of the formula $HOCH_2CH_2OCH_2CH_2OR$ where R is an alkyl group having 1 to 6 carbon atoms (e.g., ethyl); and from 0.01 weight percent to about 6 weight percent benzyl alcohol. In one aspect, the composition comprises about 2 weight percent to about 4 weight percent benzyl alcohol. The composition may additionally contain a film forming agent, e.g., in from 0.01 weight percent to about 4 weight percent. In one aspect, the film-forming agent is a maleic anhydride/methyl vinyl ether copolymer, such as Gantrez® ES-425 or Gantrez® ES-435. The composition may also contain an alcohol, such as ethanol, which in one variation is present in the composition in from about 35 weight percent to about 45 weight percent. It is understood that reference to relative weight percentages assumes that the combined total weight percentages of all components in the formulation add up to 100. It is further understood that relative weight percentages of one or more components may be adjusted upwards or downwards such that the weight percent of the components in the composition combine to a total of 100. For example, reference to a composition comprising from about 5 weight percent to about 15 weight percent luliconazole; from about 5 weight percent to about 25 weight percent acetone; from about 1 weight percent to about 15 weight percent propylene carbonate; from about 15 weight percent to about 35 weight percent of an ethylene glycol derivative, which in certain embodiments is of the formula $HOCH_2CH_2OCH_2CH_2OR$ where R is an alkyl group having 1 to 6 carbon atoms (e.g., ethyl); and from 0.01 weight percent to about 6 weight percent benzyl alcohol intends a composition wherein the weight percent of the composition components add to a total of 100 (e.g., where additional components account for any amount under 100).

In one variation, compositions are provided wherein one or more of the components (in some embodiments all of the components) of the composition are within 15%, or in an alternative embodiment, 10%, of the weight percent of each component as described in a product label accompanying distribution of the composition. For example, a composition whose accompanying product label at distribution lists 10 weight percent of luliconazole intends in one embodiment compositions comprising 9 to 11 weight percent luliconazole. It is understood that the weight percent of one or more components of these formulations can change over time (e.g., upon storage, due to volatility of one more components, such as acetone).

In some embodiments, "about X" refers to within 15 percent of X for any one (or in some embodiments all) components in a composition. In other embodiments, "about X" refers to within 10 percent of X for any one (or in some embodiments all) components in a composition.

Other relative weight percentages of the composition components are envisioned, e.g., a composition may comprise from about 9 weight percent to about 11 weight percent luliconazole; from about 8 weight percent to about 15 weight percent acetone; from about 3 weight percent to about 8 weight percent propylene carbonate; from about 20 weight percent to about 30 weight percent of an ethylene glycol derivative, which in certain embodiments of the formula $HOCH_2CH_2OCH_2CH_2OR$ where R is an alkyl group having 1 to 6 carbon atoms; and benzyl alcohol in at least 0.01 weight percent but no more than about 5 weight percent. Such compositions may also contain a film forming agent, such as a maleic anhydride/methyl vinyl ether copolymer, e.g., in from 0.01 weight percent to about 4 weight percent. Such compositions may additionally contain an alcohol, such as ethanol, e.g., in from about 35 weight percent to about 45 weight percent.

Pharmaceutical compositions comprising about 5 weight percent to about 15 weight percent luliconazole, benzyl alcohol, acetone and propylene carbonate are also provided. Such compositions may additionally contain ethanol and/or an ethylene glycol derivative of the formula $HOCH_2CH_2OCH_2CH_2OR$ where R is an alkyl group having 1 to 6 carbon atoms, such as ethyl.

Pharmaceutical compositions comprising luliconazole, an ethylene glycol derivative of the formula $HOCH_2CH_2OCH_2CH_2OR$ where R is an alkyl group having 1 to 6 carbon atoms and at least two of benzyl alcohol, acetone, propylene carbonate and ethanol are also described herein. In one aspect, such compositions comprise at least three of benzyl alcohol, acetone, propylene carbonate and ethanol. In a particular aspect, such compositions comprise benzyl alcohol, acetone and propylene carbonate, wherein the ethylene glycol derivative, acetone and propylene carbonate when taken together account for about 40 weight percent to about 45 weight percent of the composition.

Also provided are pharmaceutical compositions comprising luliconazole and at least four of benzyl alcohol, acetone, propylene carbonate, ethanol and an ethylene glycol derivative of the formula $HOCH_2CH_2OCH_2CH_2OR$ where R is an alkyl group having 1 to 6 carbon atoms (e.g., ethyl).

In one variation of the luliconazole formulations containing benzyl alcohol, the composition comprises at least 0.01 weight percent but no more than about 5 weight percent benzyl alcohol. In other aspects, the luliconazole formulations contain about 2 to about 4 weight percent benzyl alcohol.

In particular variations, compositions of luliconazole comprise about 8 weight percent to about 15 weight percent luliconazole. In further variations, compositions of luliconazole comprise about 10 weight percent or about 12.5 weight percent luliconazole.

In luliconazole compositions comprising a film forming agent, in one aspect the film forming agent is present in from 0.01 weight percent to about 4 weight percent. In one aspect, the film-forming agent is a maleic anhydride/methyl vinyl ether copolymer, such as Gantrez® ES-425 or Gantrez® ES-435.

In one aspect, luliconazole compositions described herein are substantially anhydrous.

The luliconazole compositions may provide a clear solution without evidence of crystal formation upon visual inspection after 6 months of storage at any of 5° C., 25° C. and 40° C. Such compositions solubilize luliconazole under the given conditions.

The luliconazole compositions may provide a stable composition of luliconazole in that the compositions contain at least about 95% of the theoretical maximum amount of luliconazole after 6 months of storage at any of 5° C., 25° C. and 40° C. The amount of luliconazole in solution may be measured by methods known in the art, which may include the methods described herein.

The luliconazole compositions may both solubilize luliconazole and provide a stable composition in that such compositions provide a clear solution without evidence of crystal formation upon visual inspection after 6 months of storage at any of 5° C., 25° C. and 40° C. and wherein the composition contains at least about 95% of the theoretical maximum amount of luliconazole after 6 months of storage at any of 5° C., 25° C. and 40° C.

The compositions may also exhibit efficacy against fungal infections, such as onychomycosis. In one aspect, the compositions provided herein eradicates at least 80% of a fungal infection of the nail after 14 days of treatment, as measured by the recovery of less than 20% of the theoretical amount of recoverable ATP from the fungus. Preferably, such compositions result in both high (e.g., greater than any of 80% or 85% or 90% or 95% or 98% or 99%) mycological cure and clinical cure rates.

The compositions described may also provide for penetration of luliconazole through a nail after contacting the surface of the nail, such as a toenail, with a composition described herein. For example, in one aspect a luliconazole formulation comprising about 10 weight percent luliconazole provides at least about any of 50 or 75 or 100 or 120 or 140 or 160 or 175 or 200 or more $\mu g/cm^2$ of luliconazole penetration through a 0.5-0.8 mm thick or 0.5-1.2 mm thick nail when 1 µL the composition is applied to a 0.05 cm² area of the nail once daily for 3 days. In one variation, a luliconazole formulation comprising about 10 weight percent luliconazole provides at least any of 80 or 90 or 100 or 120 or 150 or more $\mu g/cm^2$/day of luliconazole penetration through a 0.5-0.8 mm or a 0.5-1.2 mm thick nail when 1 µL the composition is applied to a 0.05 cm² area of the nail once daily for 3 days.

In one variation, the luliconazole composition is free of any of an alpha-hydroxycarboxylic acid (such as lactic acid), N-methyl-2-pyrrolidone (NMP) and crotamiton. In one aspect, the luliconazole composition is free of all of an alpha-hydroxycarboxylic acid (such as lactic acid), NMP and crotamiton. In another variation, the composition is free from any one or more (and in a particular embodiment, all of) the following: triacetin; 2-ethyl-1,3-hexanediol; lauromacrogol; polyoxyethylene; polyoxypropylene; propylene glycol; lactic acid; polypropylene glycols, diesters of dibasic acids; triacetin; 2-ethyl-1,3-hexanediol; lauromacrogol; polyoxyethylene-polyoxypropylene glycols; glycono-d-lactone; propylene glycol; glycerin; water (including free of 0.1-35% by mass of water); anionic surfactant; and a cellulose thickener.

Formulations having a quick drying time one applied to the nail are also provided, such as formulations that dry in less than about any of 5 or 3 or 2 minutes after application to a nail.

In another variation, the composition, when applied to a nail, leaves a minimal residue or film of luliconazole on the nail.

A method for treating or ameliorating a disease comprising the topical administration of a composition is provided herein. In one aspect, the disease is dermatomycosis or an onychomycosis, such as onychomycosis of a toenail and/or fingernail. In another aspect, the disease is Tinea corporis, Tinea cruris or Tinea pedis.

A method of treating onychomycosis in an individual in need thereof is provided, which in one aspect may be a method of treating distal subungual onychomycosis of a toenail and/or fingernail. In one aspect, the methods involve a once daily application of a luliconazole composition provided herein, such as a composition comprising about 10 weight percent luliconazole, to the infected nail.

Methods of delivering luliconazole to the underside of a nail and/or the nail bed are provided, wherein the method comprises administering a luliconazole composition described herein to the surface of a nail. In one aspect of the method, a luliconazole composition is applied to the surface of the nail once daily for a period of time, such as any of 1 or 2 or 3 or 4 or 5 or 6 or 9 or 12 months.

Methods of penetrating a nail, such as a fingernail or toenail, with luliconazole by contacting a nail surface with a luliconazole formulation as described herein are also provided. In one aspect, the methods employ a luliconazole formulation comprising about 10 weight percent luliconazole.

An individual that has or is suspected of having onychomycosis may administer a luliconazole composition according to the methods described herein. In one aspect, the individual is a mammal, such as a human. In a particular aspect, the individual is a human and the methods provided are directed to treating a human nail. In one aspect, the individual is diabetic, is of an advanced age or is immunocompromised.

Methods of preparing a pharmaceutical composition of luliconazole are also provided, such as methods comprising combining luliconazole with an ethylene glycol derivative of the formula $HOCH_2CH_2OCH_2CH_2OR$ where R is an alkyl group having 1 to 6 carbon atoms (e.g., ethanol), acetone, propylene carbonate, benzyl alcohol and ethanol. In one aspect, a method of preparing a luliconazole composition comprises: (a) dissolving luliconazole in one or both of benzyl alcohol and the ethylene glycol derivative; and (b) adding ethanol, propylene carbonate and acetone, to provide the composition, where a maleic anhydride/methyl vinyl ether copolymer may optionally be included in step (b) of the method.

Kits are also described, wherein the kits comprise a luliconazole composition as provided herein, and may further comprise instructions for use, such as in the treatment of onychomycosis, which may be distal subungual onychomycosis.

Articles of manufacture comprising a container in which a luliconazole composition provided herein is contained are also provided. In one aspect, the container is plastic. In one aspect, the container is glass. In another aspect, the container is a device, such as a device containing a unit dosage form of the luliconazole composition.

Other aspects of the invention are provided throughout.

BRIEF DESCRIPTION OF THE FIGURES

FIGS. 1A and 1B are graphs of scoring results for the Erythema and Eschar formation for days 1-28 in a dermal irritation study assessing the effect of a 12.5 weight percent luliconazole formulation.

FIGS. 2A and 2B are graphs of scoring results for Edema Formation for days 1-28 in a dermal irritation study assessing the effect of a 12.5 weight percent luliconazole formulation.

FIGS. 3A, 3B, 3C and 3D are graphs of scoring results for the Erythema and Eschar and Edema formation for days 35 and 42 in a dermal irritation study assessing the effect of a 12.5 weight percent luliconazole formulation.

DETAILED DESCRIPTION OF THE INVENTION

Figure 4:
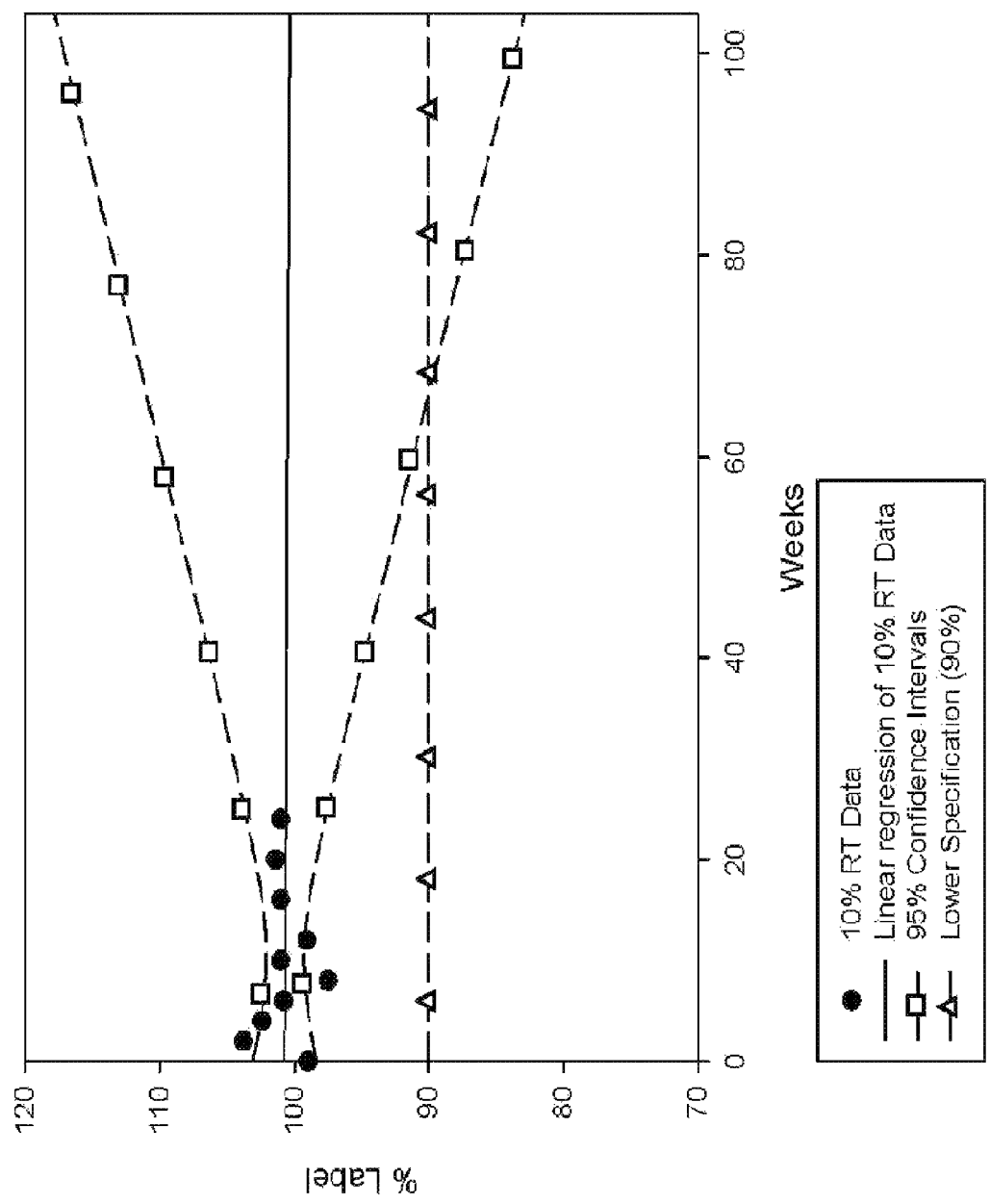
FIG. 4 is a linear regression of a 6 month stability study at 25° C. for a 10 weight percent luliconazole formulation through 2 years, indicating that the product will remain stable for up to 24 months.

Pharmaceutical compositions of luliconazole in a solvent system that solubilizes a sufficient amount of luliconazole for the treatment of onychomycosis, is stable over time, and maintains the advantages of an effective therapeutic for the treatment of onychomycosis (e.g., safety, high patient compliance, etc.) are provided. Methods of using and making pharmaceutical compositions of luliconazole are also embraced, as are kits and articles of manufacture comprising the luliconazole compositions.

It is understood that aspects and embodiments of the invention described herein include "consisting" and/or "consisting essentially of" aspects and embodiments.

Pharmaceutical Compositions

Although certain pharmaceutical compositions comprising up to 5 weight percent luliconazole are known, pharmaceutical compositions comprising greater than 5 weight percent of luliconazole are desired for use in the treatment of onychomycosis in view of the challenges associated with effective treatment of this difficult to eradicate infection. Higher concentrations of luliconazole in a pharmaceutical composition (e.g., a composition comprising about 10 weight percent to about 15 weight percent luliconazole) applied to a nail are much more likely to be able to deliver a therapeutically effective amount of luliconazole to the site of infection (e.g., a toenail, including the underside of the nail, and the nail bed) and result in complete and effective treatment that is less susceptible to reinfection and/or relapse. In addition, higher concentration compositions of luliconazole may provide easier treatment regimens, such as less than once-daily applications of the composition to an infected nail. Compositions that are stable over time and under a variety of conditions are also provided.

The difficulties in achieving higher concentration luliconazole pharmaceutical compositions suitable for chronic use are multifold. They include safety considerations as well as the interrelated and interdependent performance characteristics of a multi-solvent system, which impact the ability of the solvent system to dissolve a sufficient amount of luliconazole and its stability over time. In addition, patient compliance associated with chronic application of the composition to an infected nail is affected. That is, a solvent system containing higher luliconazole concentrations should adequately dissolve a sufficient amount of luliconazole, be safe for chronic use, provide a homogenous and physically stable composition with appropriate rheological properties, be suitable for application to the nail, have a relatively short drying time upon application, produce little to no irritation when applied, deliver a therapeutically effective amount of luliconazole to the site of infection (e.g., a toenail and/or nail bed), be chemically stable with adequate antimicrobial properties and be convenient to the user. A highly tuned system is thus required to adequately address each of these formulation challenges. The pharmaceutical compositions described herein meet each of the formulation challenges and comprise luliconazole in concentrations sufficient for use in the treatment of onychomycosis.

Luliconazole is practically insoluble in water and requires a substantially non-aqueous solvent for its complete dissolution. The luliconazole pharmaceutical compositions herein provide good efficacy in models of onychomycosis, are safe for chronic use and are stable over time. Moreover, the compositions are generally formulated with ingredients and at concentrations which are safe for topical application, as described in the U.S. Food and Drug Administration's Inactive Ingredient Guide (IIG), and contain a concentration of luliconazole sufficient for use in the treatment of onychomycosis.

Although Transcutol™ P is referred to in certain instances, it is understood that compositions comprising diethylene glycol monoethyl ether may be used. In addition, although Gantez (including Gantrez ES® 435 and Gantrez ES® 425) is referred to in certain instances, it is understood that compositions comprising butyl ester of PVM/MA copolymer may be used (such as butyl ester of PVM/MA copolymer, 38-52% isopropyl alcohol, <10% butyl alcohol). In addition, it is understood that reference to Alcohol (200 Proof) includes and intends ethanol.

In one aspect, a pharmaceutical composition of luliconazole comprising from about 9 weight percent to about 12.5 weight percent luliconazole or from about 10 weight percent to about 12.5 weight percent luliconazole; about 12 weight percent acetone; about 5 weight percent propylene carbonate; about 25 weight percent $HOCH_2CH_2OCH_2CH_2OR$ where R is an alkyl group having 1 to 6 carbon atoms (e.g., ethyl) and benzyl alcohol in at least a detectable amount but in no more than about 4 weight percent is provided. In one variation, the composition also comprises from about 40 weight percent to about 45 weight percent ethanol. The foregoing compositions in one aspect also comprise a film forming agent, such as Gantrez® ES-425 (which uses ethanol and butyl alcohol as a solvent) or Gantrez® ES-435 (which uses an isopropanol-based solvent). In a particular variation, a pharmaceutical composition of luliconazole is provided, wherein the composition comprises between about 10 weight percent luliconazole and about 15 weight percent luliconazole; about 12 weight percent acetone; about 5 weight percent propylene carbonate; about 25 weight percent $HOCH_2CH_2OCH_2CH_2OR$ where R is an alkyl group having 1 to 6 carbon atoms (e.g., ethyl); benzyl alcohol in about 2 weight percent to about 4 weight percent; and Gantrez® ES-435 in about 1 weight percent.

In any formulation described herein in which the weight percent of the listed components of the composition is less than 100, in one variation, the composition further comprises ethanol in a weight percent that provides a total weight percent of 100 for the composition. For example, in one aspect, a pharmaceutical composition of luliconazole is provided, wherein the composition comprises between about 10 weight percent luliconazole and about 15 weight percent luliconazole; about 12 weight percent acetone; about 5 weight percent propylene carbonate; about 25 weight percent $HOCH_2CH_2OCH_2CH_2OR$ where R is an alkyl group having 1 to 6 carbon atoms (e.g., ethyl); benzyl alcohol in about 2 weight percent to about 4 weight percent; Gantrez® ES-435 in about 1 weight percent; and ethanol in a weight percent that provides a total of 100 weight percent for the composition. In a particular variation, a pharmaceutical composition of luliconazole is provided, comprising about 40.5 weight percent ethanol; about 4 weight percent benzyl alcohol; about 5 weight percent propylene carbonate; about 12 weight percent acetone; about 25 weight percent $HOCH_2CH_2OCH_2CH_2OR$ where R is an alkyl group having 1 to 6 carbon atoms (e.g., ethyl); and about 12.5 weight percent luliconazole.

Because pharmaceutical compositions of luliconazole for chronic application to the nail are provided, it is important that mixed solvent components that have higher safety concerns than others are minimized. For example, in one variation of the luliconazole pharmaceutical compositions provided herein, the compositions contain sufficiently high luliconazole concentrations (e.g., about 10 weight percent luliconazole or more) for use in the treatment of onychomycosis and where the compositions contain benzyl alcohol in detectable amounts but no more than about 5 weight percent. Benzyl alcohol, which is a highly effective solvent for dissolving luliconazole, may thus be used sparingly in the present compositions. Use of less than about any of 6 or 5 or 4 or 3 or 2 weight percent benzyl alcohol can limit an individual's exposure to benzyl alcohol as compared to compositions containing greater amounts of benzyl alcohol, and result in a reduction or elimination of hemolytic effects associated with its exposure. This may be especially important in the context of chronic exposure of an individual to benzyl alcohol, e.g., by the daily use of a composition containing benzyl alcohol for a period of time that can last several months or a year or more. Significantly, mixed solvent systems comprising luliconazole concentrations in amounts sufficient to treat onychomycosis (e.g., about 10 weight percent to about 15 weight percent) are able to adequately solubilize luliconazole using only relatively low amounts of benzyl alcohol. Thus, stable pharmaceutical compositions for chronic use in the treatment of onychomycosis comprising only about 4 weight percent benzyl alcohol or less, are provided. In yet another variation, such compositions contain about 2 weight percent benzyl alcohol. In particular variations, such compositions further comprise at least one of acetone, propylene carbonate and diethylene glycol monoethyl ether. In still another variation, such compositions further comprise any two of acetone, diethylene glycol monoethyl ether and propylene carbonate. In still another variation, such compositions comprise acetone, diethylene glycol monoethyl ether and propylene carbonate.

In one variation, a pharmaceutical composition for the topical treatment of onychomycosis is provided, wherein the composition comprises luliconazole, diethylene glycol monoethyl ether, acetone and propylene carbonate. In one such variation, diethylene glycol monoethyl ether, acetone and propylene carbonate together account for about 40 weight percent to about 45 weight percent of the composition. In another variation, the multi-component solvent solution comprises acetone, propylene carbonate, diethylene glycol monoethyl ether and benzyl alcohol. A pharmaceutical composition comprising luliconazole and diethylene glycol monoethyl ether and at least two of benzyl alcohol, acetone, propylene carbonate and ethanol is also provided for use in the treatment of onychomycosis. Also described is a pharmaceutical composition comprising luliconazole and at least four of benzyl alcohol, acetone, propylene carbonate, ethanol and diethylene glycol monoethyl ether.

In one aspect, the pharmaceutical luliconazole compositions further comprises a film forming agent, such as Gantrez (e.g., Gantrez® ES-425 or Gantrez® ES-435). The film forming agent may be present in one about 1 weight percent. In one variation, the compositions provided herein comprise Gantrez® ES-435 in about 1 weight percent.

The pharmaceutical compositions of luliconazole for chronic application to the nail contain sufficiently high luliconazole concentrations such that the composition is suitable for use in the treatment of onychomycosis. In one aspect the pharmaceutical composition comprises about 8 weight percent luliconazole. In one aspect, the pharmaceutical composition comprises about 10 weight percent luliconazole. In another aspect, the pharmaceutical composition comprises about 12.5 weight percent luliconazole. In yet another aspect, the pharmaceutical composition comprises between about 10 weight percent luliconazole and about 15 weight percent luliconazole. In still a further aspect, the pharmaceutical composition comprises between about 10 weight percent luliconazole and about 12.5 weight percent luliconazole. In a further aspect, the pharmaceutical composition comprises between about 8 weight percent luliconazole and about 12 weight percent luliconazole. In a further aspect, the pharmaceutical composition comprises between about 9 weight percent luliconazole and about 11 weight percent luliconazole.

In one aspect, the compositions described herein are substantially anhydrous. By substantially anhydrous it is meant that the composition contains no more than about 5 weight percent water. A substantially anhydrous composition may in one variation contain no more than about 3 weight percent water. A composition containing no more than about 2 weight percent water is also substantially anhydrous, as is a composition containing no more than about 1 weight percent water or 0.5 weight percent water. In one variation, a composition as described herein does not contain detectable levels of water.

The compositions provided herein are, in one aspect, free of any one or more of an alpha-hydroxycarboxylic acid (e.g., lactic acid), NMP and crotamiton.

In one variation, a pharmaceutical composition of luliconazole is clear, indicating that luliconazole is soluble in the composition. In a particular variation, a pharmaceutical composition of luliconazole remains a clear solution, without evidence of crystal formation upon visual inspection after any of 1 or 2 or 3 or 4 or 5 or 6 months of storage at any of 5° C., 25° C. and 40° C.

In one variation, a pharmaceutical composition of luliconazole is chemically stable, as evidenced by any more or more of the following: (i) the composition contains at least about any of 80% or 85% or 90% or 95% of the theoretical maximum amount of luliconazole after 2 or 4 or 6 or 12 or 18 or 24 or more months of storage at any of 5° C., 25° C. and 40° C., where the theoretical maximum amount of luliconazole is the amount of luliconazole present in the composition at the time the composition is prepared, which may be referred to herein as time 0 (ii) the composition contains no more than any of 0.2 or 0.3 or 0.5 or 0.75 or 1 weight percent of the Z form of luliconazole after any of 1 or 2 or 3 or 4 or 5 or 6 or 12 or more months of storage at any of 5° C., 25° C. and 40° C.; (iii) the composition contains no more than any of 0.2 or 0.3 or 0.5 or 0.75 or 1 or 2 or 3 or 4 or 5 weight percent of the SE form of luliconazole after any of 1 or 2 or 3 or 4 or 5 or 6 or 12 or more months of storage at any of 5° C., 25° C. and 40° C.; (iv) the composition contains no more than any of 0.5, or 1 or 2 or 3 or 4 or 5 combined weight percent of the Z and SE forms of luliconazole after any of 1 or 2 or 3 or 4 or 5 or 6 or 12 or more months of storage at any of 5° C., 25° C. and 40° C.; and (v) the composition contains at least about any of 80% or 90% or 100% or 110% label of luliconazole after any of 1 or 2 or 3 or 4 or 5 or 6 or 12 or more months of storage at any of 5° C., 25° C. and 40° C.

The pharmaceutical composition, when applied to an individual's nail, in one aspect leaves only a minimal residue or film of luliconazole on the nail.

The pharmaceutical compositions of luliconazole for chronic application to the nail in one aspect provide for the penetration of a therapeutically effective amount of luliconazole through a nail after 3 days of continuous dosing of the composition to the surface of the nail. In one aspect, the composition comprises about 10 weight percent to about 15 weight percent luliconazole, wherein the composition eradicates at least 80% of a fungal infection of the nail after 14 days of treatment, as measured by the recovery of less than 20% of the theoretical amount of recoverable ATP from the fungus. In one aspect, the composition comprises about 10 weight percent to about 15 weight percent luliconazole, wherein the composition, when applied to the nail once daily for about any of 1 or 2 or 3 or 4 or 5 or 6 or 7 or 8 or 9 or 10 or 11 or 12 months, results in at least any of 80% or 85% or 90% or 95% or 100% mycological cure and/or complete clinical cure, as evaluated by methods known in the art, which in one variation are the methods described herein.

The compositions described may also provide for penetration of luliconazole through a nail, such as a toenail, after a period of time following application of the composition to the nail surface. For example, in one aspect a luliconazole formulation comprising about 10 weight percent luliconazole provides at least about any of 50 or 75 or 100 or 120 or 140 or 160 or 175 or 200 or more µg/cm² of luliconazole penetration through a 0.5-0.8 mm thick or 0.5-1.2 mm thick nail when 1 µL of the composition is applied to a 0.05 cm² area of the nail once daily for 3 days. In one variation, a luliconazole formulation comprising about 10 weight percent luliconazole provides at least any of 80 or 90 or 100 or 120 or 150 or more µg/cm²/day of luliconazole penetration through a 0.5-0.8 mm thick or 0.5-1.2 mm thick nail when 1 µL of the composition is applied to a 0.05 cm² area of the nail once daily for 3 days.

The pharmaceutical compositions described here may be in any pharmaceutically acceptable form, including but not limited to a liquid, gel, spray, foam and the like.

Methods of Use

The luliconazole pharmaceutical compositions described herein may be used in a method of treating onychomycosis in an individual in need thereof, comprising contacting the individual's nail with the composition. In one aspect, the individual is a mammal, such as a human. In a particular aspect, the individual is a human and the methods provided are directed to treating a human nail. Treatment of all categories and combinations of categories of onychomycosis with the luliconazole pharmaceutical compositions are embraced. For example, in one aspect, a method of treating distal subungual onychomycosis is provided, wherein the method comprises contacting the infected nail with the luliconazole composition. In one aspect, the nail of the present method is a toenail. In another variation, the nail of the present method is a fingernail.

In a particular variation, methods of treating onychomycosis (including but not limited to distal subungual onychomycosis) of a toenail are provided, comprising contacting the infected toenail with a luliconazole pharmaceutical composition.

A luliconazole pharmaceutical composition described herein above and throughout may be used in the methods of treating onychomycosis, the same as if each and every composition were specifically and individually listed for use in the treatment of onychomycosis. For example, it is understood that a method of treating onychomycosis, e.g., distal subungual onychomycosis, with a composition of luliconazole comprising from about 10 weight percent to about 12.5 weight percent luliconazole; about 12 weight percent acetone; about 5 weight percent propylene carbonate; about 25 weight percent diethylene glycol monoethyl ether; and benzyl alcohol in at least a detectable amount but in no more than about 4 weight percent is provided.

Methods of penetrating a nail with luliconazole, comprising contacting the individual's nail with a luliconazole pharmaceutical composition provided herein. In one aspect, the nail of the present method is a toenail. In another variation, the nail of the present method is a fingernail. In one aspect, a method of penetrating a nail with luliconazole is provided by administering a composition comprising at least about any of 8 or 10 or 12 weight percent luliconazole to the individual's nail once daily for at least about any of 3 or 7 or 21 days. In one aspect, a method of penetrating a nail with luliconazole is provided by administering a composition comprising at least about any of 8 or 10 or 12 weight percent luliconazole to the individual's nail once daily for at least about any of 1 or 2 or 3 or 4 or 6 or 8 or 10 or 12 months.

Methods of delivering luliconazole to a nail bed are provided, wherein the method comprises administering a luliconazole composition described herein to the surface of a nail. In one aspect of the method, a luliconazole composition is applied to the surface of the nail once daily for a period of time, such as any of 3 or 7 or 14 days or any of 1 or 2 or 3 or 4 or 5 or 6 or 9 or 12 months. In a particular variation, the luliconazole formulation comprises about 9-11 weight percent luliconazole.

In any of the methods provided herein, in one aspect the individual is diabetic, is of an advanced age or is immunocompromised. In any methods described herein in one aspect the individual is an individual for whom Lamisil® and/or Sporanox® are contraindicated or who would require a reduction in other medications (e.g., agents metabolized by CYP450 2D6 or CYP3A4) if they were to be administered Lamisil® and/or Sporanox®.

In one embodiment, the methods described herein can be used in conjunction with another anti-fungal therapy, such as a therapy for onychomycosis. Various exemplary therapies, such as oral anti-fungal therapies are described herein. Generally, in conjunction with refers to giving therapies in the context of a single treatment regimen.

In one aspect, treatment of onychomycosis is measured by a reduction in or the absence of the fungal infection. In one variation, treatment is achieved by an amelioration of one or more symptoms of the infection (e.g., onychomycosis), as detailed herein. Preferably, the treatments provide both a reduction or absence of fungal infection and the regrowth of clear, healthy nail.

In another aspect, the methods provide for both the treatment of onychomycosis and protection against relapse or reinfection, wherein the individual does not become reinfected with a nail fungus for at least about any of 1 or 2 or 3 months after terminating treatment of a previously infected nail for onychomycosis using a luliconazole pharmaceutical composition described herein.

Dosing Regimens and Amounts

The luliconazole pharmaceutical compositions for use in the treatment of onychomycosis are administered to the nail of an individual in an amount that provides a therapeutically effective amount of luliconazole to the infected site, which in one aspect includes the toenail and nail bed.

In one variation, a luliconazole pharmaceutical composition is administered to an infected nail once daily for the duration of the infection, which may be any of at least 1 or 2 or 4 or 6 or 9 or 12 months or more. In some instances, an individual will continue administration of a luliconazole pharmaceutical composition for a period of time after eradication of the infection, as a prophylactic measure to guard against reinfection and/or relapse. It is also contemplated that dosing regimens for the treatment of onychomycosis may be less than once daily, e.g., once every other day or thrice weekly or twice weekly or once weekly or twice a month or once a month. The less than once daily dosing regimens are particularly contemplated with luliconazole pharmaceutical compositions comprising from about 10 weight percent luliconazole to about 15 weight percent luliconazole.

In one variation of the methods, a topical daily dose of 0.1 mL of a pharmaceutical composition comprising about 8 to about 15 weight percent luliconazole is provided. In one aspect, a method of treating onychomycosis is provided wherein a topical daily dose of 0.1 mL of a pharmaceutical composition comprising about 10 weight percent luliconazole is applied to each infected nail.

Mixed dosing regimens are also provided. Given the long period of time for complete cure of onychomycosis, it is contemplated that in one aspect, an individual will administer a luliconazole pharmaceutical composition as provided herein once daily for a first period of time, after which the individual will administer the luliconazole pharmaceutical composition in a less than daily regimen (e.g., in once weekly intervals) for a second period of time. Further tapering of the dosing interval is contemplated and may be determined based on progress of the individual's treatment.

Methods of Making Pharmaceutical Compositions

Also embraced herein is a method for preparing a pharmaceutical composition of luliconazole for topical application, comprising combining luliconazole with diethylene glycol monoethyl ether, acetone, propylene carbonate, benzyl alcohol and ethanol.

In one aspect, the method comprises (a) dissolving luliconazole in one or both of benzyl alcohol and diethylene glycol monoethyl ether; and (b) adding ethanol, propylene carbonate, acetone and Gantrez, to provide the composition.

In one variation, a formulation comprising a film former (e.g., Gantrez® ES-435 or Gantrez® ES-425), ethanol, benzyl alcohol, propylene carbonate and diethylene glycol monoethyl ether is prepared by mixing in a primary mixing vessel, the film former, ethanol, benzyl alcohol, propylene carbonate and diethylene glycol monoethyl ether. Acetone and luliconazole are added and the contents are mixed until all solids are visually dissolved. In one aspect, acetone and luliconazole are added under amber lighting.

In one embodiment, the invention embraces products produced from the processes described herein.

Kits

Kits comprising a luliconazole pharmaceutical composition are also provided. In one aspect, the kit comprises instructions for use in the treatment of onychomycosis. In a particular variation, the instructions are directed to use of a luliconazole pharmaceutical composition for the treatment of distal subungual onychomycosis.

Any luliconazole pharmaceutical composition detailed herein above and throughout may be used in the kits, the same as if each and every composition were specifically and individually listed for use a kit. For example, it is understood that a kit comprising a luliconazole pharmaceutical composition comprising from about 10 weight percent to about 12.5 weight percent luliconazole; about 12 weight percent acetone; about 5 weight percent propylene carbonate; about 25 weight percent diethylene glycol monoethyl ether; and benzyl alcohol in at least a detectable amount but in no more than about 4 weight percent is provided. The kit may optionally include instructions, such as for the use in treating a nail (e.g., a toenail) for onychomycosis. The kit may include additional components relating to care of a nail, such as a nail file.

Articles of Manufacture

Articles of manufacture comprising a container in which a luliconazole pharmaceutical composition is contained are provided. The article of manufacture may be a bottle, vial, ampoule, single-use disposable applicator, or the like, containing a luliconazole pharmaceutical composition as described herein. The container may be formed from a variety of materials, such as glass or plastic and in one aspect also contains a label on, or associated with, the container which indicates directions for use in the treatment of onychomycosis.

In one aspect, the container is a medical device containing a unit dosage form of a luliconazole pharmaceutical composition. The device may be a brush or applicator for applying the composition to the surface of the nail plate.

Unit dosage forms of the luliconazole pharmaceutical compositions are also provided.

Any luliconazole pharmaceutical composition described herein above and throughout may be used in the articles of manufacture, the same as if each and every composition were specifically and individually listed for use an article of manufacture. For example, it is understood that a article of manufacture may comprise a luliconazole pharmaceutical composition comprising from about 10 weight percent to about 12.5 weight percent luliconazole; about 12 weight percent acetone; about 5 weight percent propylene carbonate; about 25 weight percent diethylene glycol monoethyl ether; and benzyl alcohol in at least a detectable amount but in no more than about 4 weight percent is provided.

DEFINITIONS AND FURTHER EMBODIMENTS

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

As is well understood by one skilled in the art, reference to "about" a value or parameter herein includes (and describes) embodiments that are directed to that value or parameter per se. For example, "about X" includes description of and describes "X."

"Therapeutically effective amount" means a drug amount that elicits any of the biological effects listed in the specification.

"Treatment" includes any one or more of desirable endpoints, including clinical endpoints, as described herein.

The term "composition" used herein may be used interchangeably with the term "formulation."

The compositions described herein are used to treat conditions of the skin or the nail. Examples of such conditions include, but are not limited to, infections, inflammation, psoriasis, paronychia, benign or malignant skin or nail tumors and aesthetic conditions. In one aspect of the present application, the compositions are used to treat dermatomycoses or onychomycosis.

Dermatomycoses refers to an infection of the skin caused by dermatophytes or other fungi. Examples of dermatomycoses include, but are not limited to Tinea corporis, Tinea cruris or Tinea pedis. Examples of pathogens which are known to cause dermatomycoses include, but are not limited to *Trichophyton rubrum, Trichophyton interdigitale, Trichophyton rubrum* (most common in New Zealand), *Trichophyton interdigitale, Trichophyton tonsurans* (very common in the USA), *Microsporum audouinii, Trichophyton violaceum, Microsporum ferrugineum, Trichophyton schoenleinii, Trichophyton megninii, Trichophyton soudanense, Trichophyton yaoundei, Trichophyton mentagrophytes* and *Trichophyton tonsurans*.

Onychomycosis refers to a fungal infection of the nail plate and/or nail bed, also known as Tinea unguium. Examples of pathogens which are known to cause onychomycosis include, but are not limited to dermatophytes, such as *Trichophyton rubrum, Trichophyton interdigitale, Epidermophyton floccosum, Trichophyton violaceum, Microsporum gypseum, Trichophyton tonsurans, Trichophyton soudanense* and *Trichophyton verrucosum; Candida*, such as, *Candida albicans* and non-dermatophytic moulds, such as *Scopulariopsis brevicaulis* and *Fusarium* species.

Onychomycosis can affect the nail plate, the nail bed (the tissue directly under the nail plate), the nail matrix or nail root (the thickened skin at the base of the nail from which the nail plate develops), the cuticle, the hyponychium (the thickened layer of epidermis beneath the free end of the nail), and the proximal and lateral nail folds (the skin adjacent to the base and sides of the nail). Onychomycosis can be categorized into several varieties based on clinical appearance. All categories of onychomycosis are encompassed in the methods described herein, including distal and lateral subungual onychomycosis (DLSO), endonyx onychomycosis (EO), white superficial onychomycosis (WSO), proximal subungual onychomycosis (PSO), *Candida* onychomycosis (CO) and total dystrophic onychomycosis (TDO). An individual with onychomycosis may have one variety or any combination of varieties.

Examples of active agents that may be employed in the formulations described herein include, but are not limited to, antibiotics, antifungals, anti-inflammatories, antipsoratic, anticancers, and other active agents steroids, methotrexate, cyclosporine, retinoids, pharmaceutically acceptable salts thereof and combinations thereof.

Examples of antifungal agents include, but are not limited to, ketoconazole, miconazole, bifonazole, butoconazole, clomidazole, clotrimazole, croconazole, eberconazole, econazole, fenticonazole, flutimazole, isoconazole, ketoconazole, lanoconazole, luliconazole, neticonazole, omoconazole, oxiconazole, setraconazole, sulconazole, tioconazole, fluconazole, itraconazole, terconazole, terbinafine, natrifine, amorolfine, amphotericin B, nystatin, natamaycin, flucytosine, griseofulvin, potassium iodide, butenafine, ciclopirox, ciloquinol (iodochlorhydroxyquin), haloprogin, tolnaftate, aluminum chloride, undecylenic acid, potassium permanganate, selenium sulphide, salicylic acid, zinc pyruthione, bromochlorsalicylanilide, methylrosaniline, tribromometacresol, undecylenic acid, polynoxylin, 2-(4-chlorphenoxy)-ethanol, chlorophensesin, ticlatone, sulbentine, ethyl hydroxybenzoate, dimazole, tolciclate, sulphacetamide, benzoic acid and pharmaceutically acceptable salts thereof. A preferred antifungal agent is luliconazole, which is also described in Table 1b.

TABLE 1b

Luliconazole Names and Description

| Name: luliconazole | Description |
| --- | --- |
| CAS Registry Number | 187164-19-8 |
| Chemical Names | (−)-(E)-[(4R)-(2,4-dichlorophenyl)-1,3-dithiolan-2-ylidene](1H-imidazol-1-yl)acetonitrile |
| Chemical Class | Imidazole |
| Molecular Formula | $C_{14}H_9Cl_2N_3S_2$ |
| Company codes | NND-502, PR-2699 |

Luliconazole has excellent antifungal activity against dermatophyte (*Trichophyton, Microsporum*, and *Epidermaophyton* spp.), *Candida* and *Malassezia*. Luliconazole also has excellent antifungal activity against *T. ruburm*, which is the major dermatophyte in onychomycosis. Minimal inhibitory concentrations (MICs) of luliconazole against fresh clinical isolates of the dermatopyte have been found to be between 0.00012 and 0.004 μg/mL, and its fungicidal activity has been demonstrated in low concentrations. Luliconazole exhibits strong antifungal activity against other pathogenic fungi (yeast-like fungus), *Aspergillus*, and dematiaceae). See, e.g., Niwano, Y, et al., In Vitro and In Vivo Antidermatophyte Activities of NND-502, a Novel Optically Active Imidazole Antimycotic Agent. *Antimicrob. Agents Chemother.* 1998; 42:967-970 and Koga H. et al, In Vitro Antifungal Activities of Luliconazole, a New Topical Imidazole. *Med. Mycology*, 2008:1-8.

In addition to having a broad antifungal spectrum, luliconazole has high retention in the skin and reversible binding to keratine. In animal infection models, luliconazole has equivalent or stronger therapeutic effects compared to commercially available externally applied anti-fungal drugs within shorter application periods.

The phrase "luliconazole type" refers to any antifungal agents having similar properties and activities against dermatophytes or other fungi known or suspected to cause disease as luliconazole.

The term "stable" refers to a composition or a formulation that remains substantially unchanged or substantially unaltered under conditions of manufacture and storage over a period of time under specific conditions. In particular, the composition remains substantially unchanged or unaltered when kept at a temperature of about 30° C. or less, at about 25° C. or less, at about 15° C. or less, at about 5° C. or less, for at least one week, at least two weeks, at least three weeks or at least four weeks. In certain formulations of the antifungal agents as known in the art, under certain conditions over a period of time, the agents may precipitate out or crystallize out from the formulation upon storage, and such precipitation or crystallization may be deemed to result in an "unstable" formulation.

The term "excipient" refers to an inactive substance used as a carrier for the active agent for the compositions described herein. In one aspect of the invention, excipients include by example an alcohol, such as, but not limited to, ethanol or benzyl alcohol; a ketone, such as, but not limited to acetone; an ethylene glycol derivative, such as, but not limited to diethylene glycol monoethyl ether (such as Transcutol™ P), including the ethyl ether or methyl ether analogues; or polar aprotic solvents, such as, but not limited to dimethyl sulfoxide (DMSO) and propylene carbonate (PC). In other aspects of the invention, excipients include, without limitation, alpha-hydroxycarboxylic acids and their salts and diesters of dibasic acids. In yet another aspect of the invention, the excipient is a surface active agent. Also included herein are diisopropyl adipate, N-methyl-2-pyrrolidone and lactic acid. Examples of excipients include, but are not limited to 1,2,6-hexanetriol, 1,3-dimethylol-5,5-dimethyl-hydantoin, 1-o-tolylbiguanide, 2-amino-2-methyl-1-propanol, 2-ethylhexyl salicylate, acetic acid, acetone, acrylates copolymer, acrylic acid homopolymer, acrylic acid/isooctylacrylate copolymer, adcote 72A103, adhesive tape, adhesive tape, aerotex resin 3730, ethyl alcohol, dehydrated ethyl alcohol, denatured ethyl alcohol, diluted 50% aqueous ethyl alcohol, alkyl ammonium sulfonic acid betaine, alkyl aryl sodium sulfonate, allantoin, almond oil, alpha-terpineol, alpha-tocopherol, aluminum acetate, aluminum chlorhydroxy allantoinate, aluminum hydroxide, aluminum hydroxide—sucrose, hydrated aluminum hydroxide gel, aluminum hydroxide gel F 500, aluminum hydroxide gel F 5000, aluminum monostearate, aluminum oxide, aluminum polyester, aluminum silicate, aluminum starch octenylsuccinate, aluminum stearate, aluminum sulfate anhydrous, amerchol C, amerchol-cab, ammonia solution, strong ammonia solution, ammonium hydroxide, ammonium lauryl sulfate, ammonium nonoxynol 4 sulfate, ammonium salt of C-12-C-15 linear primary alcohol ethoxylate, ammonyx, amphoteric-2, amphoteric-9, anhydrous dibasic calcium phosphate, anoxid SBN, antifoam, apricot kernel oil PEG-6 esters, aquaphor, arlacel, arlatone 289, ascorbic acid, ascorbyl palmitate, canada balsam, beeswax, synthetic beeswax, beheneth-10, bentonite, bentonite, benzalkonium chloride, benzoic acid, benzyl alcohol, betadex, boric acid, butyl alcohol, butyl ester of PVM/MA copolymer, butyl stearate, butylated hydroxyanisole, butylated hydroxytoluene, butylene glycol, butylparaben, C20-40 pareth-24, calcium acetate, calcium chloride, calcium hydroxide, caprylic/capric triglyceride, caprylic/capric/stearic triglyceride, captan, caramel, carbomer 1342, carbomer 934, carbomer 934-p, carbomer 940, carbomer 941, carbomer 974P, carbomer 980, carbomer 980, carbomer 981, carbomer homopolymer type C, carboxy vinyl copolymer, carboxymethylcellulose, carboxymethylcellulose sodium, carrageenan, carrageenan salt, castor oil, castor oil hydrogenated, cedar leaf oil, cellulose, cerasynt-se, ceresin, ceteareth-12, ceteareth-15, ceteareth-30, cetearyl alcohol, cetearyl alcohol/ceteareth-20, cetearyl octanoate, ceteth-10, ceteth-2, ceteth-20, ceteth-23, cetrimonium chloride, cetyl alcohol, cetyl esters, cetyl palmitate, cetylpyridinium chloride, chemoderm 6401B, chlorobutanol, chlorocresol, chloroxylenol, cholesterol, choleth-24, citric acid, citric acid monohydrate, hydrous citric acid, cocamide diethanolamine, cocamide ether sulfate, cocamine oxide, coco betaine, cocoa butter, cocoglycerides, cocomonoethanolamide, coconut oil, fractioned coconut oil, cocoyl caprylocaprate, collagen, coloring suspension, cream base, creatinine, crospovidone, crospovidone, cyclomethicone, cyclomethicone/dimethicone copolyol, daubert 1-5 PESTR (matte) 164Z, dehydroacetic acid, dehymuls E, denatonium benzoate, dextrin, diazolidinylurea, dichlorobenzyl alcohol, dichlorodifluoromethane, dichlorotetrafluoroethane, diethanolamine, diethyl sebacate, diethylene glycol monoethyl ether, diethylene glycol monoethyl ether, dihydroxyaluminum aminoacetate, diisopropanolamine, diisopropyl adipate, diisopropyl dimerate, dimethicone 350, dimethicone 360, dimethicone copolyol, dimethicone MDX4-4210, dimethyl isosorbide, dimethyl sulfoxide, dioctyl phthalate, dipropylene glycol, disodium cocoamphodiacetate, disodium laureth sulfosuccinate, disodium lauryl sulfosuccinate, docosanol, docusate sodium, duro-TAK 280-2516, duro-TAK 80-1196, duro-TAK 87-2070, duro-TAK 87-2194, duro-TAK 87-2287, duro-TAK 87-2296, duro-TAK 87-2888, duro-TAK 87-2979, edetate sodium, edetic acid, entsulfon, entsulfon sodium, essence, bouquet 9200, ethyl acetate, ethyl hexanediol, ethyl oleate, ethylcellulose, ethylene glycol, ethylene vinyl acetate copolymer, ethylenediamine, ethylenediamine dihydrochloride, ethylene-propylene copolymer, ethylparaben, eudragit E 100, fatty acid esters, fatty acid pentaerythriol ester, fatty acids, fatty alcohol citrate, ferric oxide, flavor rhodia pharmaceutical #RF 451, formaldehyde, formaldehyde solution, gelatin, gelva 737, gluconolactone, glycerin, glyceryl citrate, glyceryl isostearate, glyceryl laurate, glyceryl monostearate, glyceryl oleate, glyceryl oleate, glyceryl oleate/propylene glycol, glyceryl palmitate, glyceryl ricinoleate, glyceryl stearate-laureth-23, glyceryl stearate SE, glyceryl stearate/PEG-100 stearate, glyceryl stearate-stearamidoethyl diethylamine, glycol distearate, guar gum, hair conditioner (18N195-1M), herbacol, hexylene glycol, hyaluronate sodium, plasticized hydrocarbon gel, hydrochloric acid, diluted hydrochloric acid, hydrogen peroxide, hydrogenated palm/palm kernel oil PEG-6 esters, hydroxyethyl cellulose, hydroxyethyl cellulose, hydroxymethyl cellulose, hydroxyoctacosanyl hydroxystearate, hydroxypropyl cellulose, hydroxypropyl cellulose, hypromellose, imidurea, ink flexographic pink, ink/polyethylene, terephthalate/aluminum/polyethylene/sodium polymethacrylate/ethylene vinylacetate copolymer, irish moss extract, isoceteth-20, isooctylacrylate, isopropyl alcohol, isopropyl isostearate, isopropyl myristate, isopropyl myristate, isopropyl myristate—myristyl alcohol, isopropyl palmitate, isopropyl stearate, isostearic acid, isostearyl alcohol, jelene, kaolin, kathon CG, kathon CG II, lactate, lactic acid, dl-lactic acid, lactose, laneth, lanolin, lanolin alcohol-mineral oil, lanolin alcohols, acetylated lanolin alcohols, lanolin anhydrous, lanolin cholesterols, lanolin, hydrogenated, lauramine oxide, laurdimonium hydrolyzed animal collagen, laureth sulfate, laureth-2, laureth-23, laureth-4, lauric diethanolamide, lauric myristic diethanolamide, lauryl lactate, lauryl sulfate, lecithin, lemon oil, light mineral oil, limonene, dl-, lipocol SC-15, magnesium aluminum silicate, magnesium aluminum silicate hydrate, magnesium nitrate, magnesium stearate, mannitol, maprofix, medical adhesive modified S-15, medical antiform a-f emulsion, menthol, methoxypolyoxyethylene glycol 350, methyl alcohol, methyl gluceth-10, methyl gluceth-120 dioleate, methyl gluceth-20, methyl gluceth-20 sesquistearate, methyl glucose sesquistearate, methyl laurate, methyl salicylate, methyl stearate, methylcellulose, methylchloroisothiazolinone, ethylisothiazolinone, methylparaben, microcrystalline wax, mineral oil, multisterol extract, myristyl alcohol, myristyl lactate, n,n-bis(2-hydroxyethyl)stearamide, n,n-dimethyl lauramine oxide, n-3-chloroallyl-methenamine chloride, n-decyl-methyl sulfoxide, niacinamide, nitric acid, nonoxynol-15, nonoxynol-9, octadecene-1/maleic acid copolymer, octoxynol-1, octoxynol-9, octyl hydroxystearate, octyldodecanol, octyldodecanol, oleic acid, oleth-10/oleth-5, oleth-2, oleth-20, oleyl alcohol, oleyl oleate, olive oil, orvus k liquid, palmitamine oxide, parabens, paraffin, white soft paraffin, parfum creme 45/3, peanut oil, pectin, PEG 6-32 stearate/glycol stearate, PEG-22 methyl ether/dodecyl glycol copolymer, PEG-25 propylene glycol stearate, PEG-45/dodecyl glycol copolymer, peglicol-5-oleate, pegoxol 7 stearate, pentadecalactone, pentaerythritol cocoate, peppermint oil, perfume 25677, perfume bouquet, perfume E-1991, perfume GD 5604, perfume tana 90/42 SCBA, perfume W-1952-1, petrolatum, white petrolatum, petroleum distillates, phenonip, phenoxyethanol, phenylmercuric acetate, phosphoric acid, pine needle oil, plastibase-50w, polacrilin, poloxamer 124, poloxamer 181, poloxamer 182, poloxamer 188, poloxamer 237, poloxamer 407, polybutene, polycarbophil, polyester, fluoro-polyester chemical releasing agent, polyester fluorocarbon diacrylate, polyester polyamine copolymer, polyethylene, polyethylene glycol 1000, polyethylene glycol 1500, polyethylene glycol 1540, polyethylene glycol 200, polyethylene glycol 300, polyethylene glycol 300-1600, polyethylene glycol 3350, polyethylene glycol 400, polyethylene glycol 4000, polyethylene glycol 540, polyethylene glycol 600, polyethylene glycol 6000, polyethylene glycol 8000, polyethylene glycol 900, polyethylene terephthalates, polyhydroxyethyl methacrylate, polyisobutylene, polyisobutylene 1,200,000, polyisobutylene 1,200,000, polyisobutylene 35,000, polyisobutylene low molecular weight, polyisobutylene medium molecular weight, polyisobutylene/polybutene adhesive, polyoxyethylene-polyoxypropylene 1800, polyoxyethylene alcohols, polyoxyethylene fatty acid esters, polyoxyethylene propylene, polyoxyl 100 glyceryl stearate, polyoxyl 100 stearate, polyoxyl 15 cocamine, polyoxyl 150 distearate, polyoxyl 2 stearate, polyoxyl 20 cetostearyl ether, polyoxyl 4 dilaurate, polyoxyl 40 hydrogenated castor oil, polyoxyl 40 stearate, polyoxyl 400 stearate, polyoxyl 50 stearate, polyoxyl 6 and polyoxyl 32 palmitostearate, polyoxyl 6 isostearate, polyoxyl 60 hydrogenated castor oil, polyoxyl 75 lanolin, polyoxyl 8 laurate, polyoxyl 8 stearate, polyoxyl distearate, polyoxyl glyceryl stearate, polyoxyl lanolin, polyoxyl stearate, polypropylene, polyquaternium-1, polyquaternium-10, polyquaternium-7, polysorbate 20, polysorbate 20, polysorbate 40, polysorbate 60, polysorbate 65, polysorbate 80, polyvinyl acetate, polyvinyl alcohol, polyvinyl alcohol, polyvinyl chloride-polyvinyl acetate copolymer, polyvinylpyridine, potash, potassium citrate, potassium hydroxide, potassium soap, potassium sorbate, povidone acrylate copolymer, povidone hydrogel, povidone K29-32, povidone K90, povidone/eicosene copolymer, PPG-12/SMDI copolymer, PPG-15 stearyl ether, PPG-20 methyl glucose ether distearate, PPG-26 oleate, product WAT, promalgen type G, promulgen D, promulgen G, propellant A-46, propyl gallate, propylene carbonate, propylene glycol, propylene glycol, propylene glycol, propylene glycol diacetate, propylene glycol dicaprylate, propylene glycol monolaurate, propylene glycol monostearate, propylene glycol palmitostearate, propylene glycol ricinoleate, propylene glycol/diazolidinyl urea/methylparaben/propylparben, propylparaben, protein hydrolysate, quaternium-15, quaternium-52, quatrimycin hydrochloride, RA-2397, RA-3011, saccharin, saccharin sodium, safflower oil, scotchpak 1109, scotchpak 9739 backing film PET/EVA, SD alcohol 3A, SD alcohol 40, SD alcohol 40-2, SD alcohol 40b, silicon dioxide, colloidal silicon dioxide, silicone, silicone adhesive 4102, silicone emulsion, silicone/polyester film strip, simethicone, simethicone emulsion, sipon 1-20, sodium acetate, sodium acetate anhydrous, sodium alkyl sulfate, sodium benzoate, sodium cetearyl sulfate, sodium chloride, sodium chloride, sodium citrate, sodium citrate, sodium cocoyl sarcosinate, sodium dodecyl benzene sulfonate, sodium formaldehyde sulfoxylate, sodium hydroxide, sodium iodide, sodium lactate, sodium laureth sulfate, sodium laureth-2 sulfate, sodium laureth-5 sulfate, sodium lauroyl sarcosinate, sodium lauryl sulfate, sodium lauryl sulfoacetate, sodium metabisulfite, sodium phosphate, dibasic sodium phosphate, dibasic anhydrous sodium phosphate, dibasic dihydrate sodium phosphate, sodium phosphate, dibasic, heptahydrate monobasic sodium phosphate, monobasic sodium phosphate anhydrous, monohydrate sodium phosphate, monobasic, sodium polyacrylate, sodium pyrrolidone carboxylate, sodium sulfite, sodium sulfosuccinated undecyclenic monoalkylolamide, sodium thiosulfate, sodium xylenesulfonate, solulan, somay 44, sorbic acid sorbitan, sorbitan monolaurate, sorbitan monooleate, sorbitan monooleate, sorbitan monopalmitate, sorbitan monostearate, sorbitan sesquioleate, sorbitol, sorbitol solution, soybean flour, soybean oil, spearmint oil, spermaceti, squalane, starch, starch aluminum octenyl succinate, stearalkonium chloride, stearalkonium hectorite/propylene carbonate, stearamidoethyl diethylamine, steareth-10, steareth-100, steareth-2, steareth-20, steareth-21, stearic acid, stearoxytrimethylsilane, steartrimonium hydrolyzed animal collagen, stearyl alcohol, stearyl citrate, styrene/isoprene/styrene block copolymer, sucrose, sucrose distearate, sucrose polyesters, sulfacetamide sodium, sulfuric acid, surfactol SQ, talc, tall oil, tallow glycerides, tartaric acid, tenox, tenox-2, tert-butyl alcohol, thimerosal, titanium dioxide, titanium dioxide, tocopherol, tocophersolan, triacetin, trichloromonofluoromethane, trideceth-10, medium chain triglycerides, trihydroxystearin, trilaneth-4 phosphate, trilaureth-4 phosphate, trisodium citrate dihydrate, trisodium citrate, anhydrous, trisodium hedta, triton X-200 sodium salt of alkyllauryl polyether sulfonate, trolamine, trolamine lauryl sulfate, tromethamine, tromethamine, tyloxapol, undecylenic acid, union 76 AMSCO-RES 6038, vegetable oil, hydrogenated vegetable oil, viscarin, viscose/cotton, wax, dehydag, emulsifying wax, white wax, wecobee FS, xanthan gum, xanthan gum and zinc acetate.

The term "surface active agents" includes a variety of ethylene glycol derivatives and other compounds including, withour limitation compounds belonging to the following classes: polyethoxylated fatty acids, PEG-fatty acid diesters, PEG-fatty acid mono-ester and all-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, and ionic surfactants. Certain of these have been disclosed as ethylene glycol derivatives before. Certain non-limiting, commercially available, examples for each class of excipient are provided below.

Polyethoxylated fatty acids can be used as excipients for the compositions provided herein. Examples of commercially available polyethoxylated fatty acid monoester surfactants include: PEG 4-100 monolaurate (Crodet L series, Croda), PEG 4-100 monooleate (Crodet 0 series, Croda), PEG 4-100 monostearate (Crodet S series, Croda, and Myrj Series, Atlas/ICI), PEG 400 distearate (Cithrol 4DS series, Croda), PEG 100, 200, or 300 monolaurate (Cithrol ML series, Croda), PEG 100, 200, or 300 monooleate (Cithrol MO series, Croda), PEG 400 dioleate (Cithrol 4D0 series, Croda), PEG 400-1000 monostearate (Cithrol MS series, Croda), PEG-1 stearate (Nikkol MYS-1EX, Nikko, and Coster K1, Condea), PEG-2 stearate (Niklol MYS-2, Nikko), PEG-2 oleate (Nikkol MYO-2, Nikko), PEG-4 laurate (Mapeg( ) 200 mL, PPG), PEG-4 oleate (Mapeg( ) 200 MO, PPG), PEG-4 stearate (Kessco PEG 200 MS, Stepan), PEG-5 stearate (Nikkol TMGS-5, Nikko), PEG-5 oleate (Nikkol TMGO-5, Nikko), PEG-6 oleate (Argon OL 60, Auschem SpA), PEG-7 oleate (Argon OL 70, Auschem SpA), PEG-6 laurate (Kessco PEG300 mL, Stepan), PEG-7 laurate (Lauridac 7, Condea), PEG-6 stearate (Kessco, PEG300 MS, Stepan), PEG-8 laurate (Mapeg( ) 400 mL, PPG), PEG-8 oleate (Mapeg 400 MO, PPG), PEG-8 stearate (Mapeg) 400 MS, PPG), PEG-9 oleate (Emulgante A9, Condea), PEG-9 stearate (Cremophor S9, BASF), PEG-10 laurate (Nikkol MYL-10, Nikko), PEG-10 oleate (Nikkol MYO-10, Nikko), PEG-12 stearate (Nikkol MYS-10, Nikko), PEG-12 laurate (Kessco PEG 600 mL, Stepan), PEG-12 oleate (Kessco PEG 600 MO, Stepan), PEG-12 ricinoleate (CAS 9004-97-1), PEG-12 stearate (Mapeg 600 MS, PPG), PEG-15 stearate (Nikkol TMGS-15, Nikko), PEG-15 oleate (Nikkol TMGO-15, Nikko), PEG-20 laurate (Kessco PEG 1000 mL, Stepan), PEG-20 oleate (Kessco PEG 1000 MO, Stepan), PEG-20 stearate (Mapeg 1000 MS, PPG), PEG-25 stearate (Nikkol MYS-25, Nikko), PEG-32 laurate (Kessco@D PEG 1540 mL, Stepan), PEG-32 oleate (Kessco) PEG 1540 MO, Stepan), PEG-32 stearate (Kessco PEG 1540 MS, Stepan), PEG-30 stearate (Myrj 51), PEG-40 laurate (Crodet L40, Croda), PEG-40 oleate (Crodet 040, Croda), PEG-40 stearate (Emerest 2715, Henkel), PEG-45 stearate (Nikkol MYS-45, Nikko), PEG-50 stearate (Myrj 53), PEG-55 stearate (Nikkol MYS 55, Nikko), PEG-100 oleate (Crodet 0-100, Croda), PEG-100 stearate (Ariacel 165, ICI), PEG-200 oleate (Albunol 200 MO, Taiwan Surf.), PEG-400 oleate (LACTO-MUL, Henkel), and PEG-600 oleate (Albunol 600 MO, Taiwan Surf.). Compositions of the application can include one or more of the polyethoxylated fatty acids above.

Polyethylene glycol fatty acid diesters can also be used as excipients for the compositions provided herein. Examples of commercially available polyethylene glycol fatty acid diesters include: PEG-4 dilaurate (Mapeg) 200 DL, PPG), PEG-4 dioleate (Mapeg 200 DO, PPG), PEG-4 distearate (Kessco 200 DS, Stepan), PEG-6 dilaurate (Kessco PEG 300 DL, Stepan), PEG-6 dioleate (Kessco PEG 300 DO, Stepan), PEG-6 distearate (Kessco PEG 300 DS, Stepan), PEG-8 dilaurate (Mapeg 400 DL, PPG), PEG-8 dioleate (Ma peg 400 DO, PPG), PEG-8 distearate (Ma peg 400 DS, PPG), PEG-10 dipalmitate (Polyaldo 2PKFG), PEG-12 dilaurate (Kessco PEG 600 DL, Stepan), PEG-12 distearate (Kessco PEG 600 DS, Stepan), PEG-12 dioleate (Mapeg) 600 DO, PPG), PEG-20 dilaurate (Kessco PEG 1000 DL, Stepan), PEG-20 dioleate (Kessco) PEG 1000 DO, Stepan), PEG-20 distearate (Kessco PEG 1000 DS, Stepan), PEG-32 dilaurate (Kessco PEG 1540 DL, Stepan), PEG-32 dioleate (Kessco) PEG 1540 DO, Stepan), PEG-32 distearate (Kessco PEG 1540 DS, Stepan), PEG-400 dioleate (Cithrol 4D0 series, Croda), and PEG-400 distearate Cithrol 4DS series, Croda). Certain compositions of the application can include one or more of the polyethylene glycol fatty acid diesters above.

PEG-fatty acid mono- and all-ester mixtures can be used as excipients for the formulation of the compositions provided herein. Examples of commercially available PEG-fatty acid mono- and all-ester mixtures include: PEG 4-150 mono, dilaurate (Kessco PEG 200-6000 mono, Dilaurate, Stepan), PEG 4-150 mono, dioleate (Kessco PEG 200-6000 mono, Dioleate, Stepan), and PEG 4-150 mono, distearate (Kessco 200-6000 mono, Distearate, Stepan). Certain compositions of the application can include one or more of the PEG-fatty acid mono- and all-ester mixtures above.

In addition, polyethylene glycol glycerol fatty acid esters can be used as excipients for the compositions described herein. Examples of commercially available polyethylene glycol glycerol fatty acid esters include: PEG-20 glyceryl laurate (Tagat) L, Goldschmidt), PEG-30 glyceryl laurate (Tagat L2, Goldschmidt), PEG-15 glyceryl laurate (Glycerox L series, Croda), PEG-40 glyceryl laurate (Glycerox L series, Croda), PEG-20 glyceryl stearate (Capmul EMG, ABITEC), and Aldo MS-20 KFG, Lonza), PEG-20 glyceryl oleate (Tagat O, Goldschmidt), and PEG-30 glyceryl oleate (Tagat 02, Goldschmidt). Certain compositions of the application can include one or more of the polyethylene glycol glycerol fatty acid esters above.

Alcohol-oil transesterification products can also be used as excipients for the compositions provided herein. Examples of commercially available alcohol-oil transesterification products include: PEG-3 castor oil (Nikkol C0-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin PRT 56, Pulcra SA), PEG-60 castor oil (Nikkol CO-60TX, Nikko), PEG-100 castor oil, PEG-200 castor oil (Eumulgin PRT 200, Fulcra SA), PEG-5 hydrogenated castor oil (Nikkol HCO-5, Nikko), PEG-7 hydrogenated castor oil (Cremophor W07, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol 1292, Seppic), PEG-30 hydrogenated castor oil (Nikkol HCO 30, Nikko), PEG-40 hydrogenated castor oil (Cremophor RH 40, BASF), PEG hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), PEG-100 hydrogenated castor oil (Nikkol HCO 100, Nikko), PEG-6 corn oil (Labrafl M 2125 CS, Gattefosse), PEG-6 almond oil (Labrafil M 1966 CS, Gattefosse), PEG-6 apricot kernel oil (Labrafl M 1944 CS, Gattefosse), PEG-6 olive oil (Labrafil) M 1980 CS, Gattefosse), PEG-6 peanut oil (Labrafil) M 1969 CS, Gattefosse), PEG-6 hydrogenated palm kernel oil (Labrafil M 2130 BS, Gattefosse), PEG-6 palm kernel oil (Labrafil M 2130 CS, Gattefosse), PEG-6 triolein (Labrafl M 2735 CS, Gattefosse), PEG-8 corn oil (Labrafl WL 2609 BS, Gattefosse), PEG-20 corn glycerides (Crovol M40, Croda), PEG-20 almond glycerides (Crovol A40, Croda), PEG-25 trioleate (TAGAT TO, Goldschmidt), PEG-40 palm kernel oil (Crovol PK-70), PEG-60 corn glycerides (Crovol M70, Croda), PEG-60 almond glycerides (Crovol A70, Croda), PEG-4 caprylic/capric triglyceride (Labrafac( ) Hydro, Gattefos se), PEG-8 caprylic/capric glycerides (Labrasol, Gattefosse), PEG-6 caprylic/capric glycerides (SOFTIGEN767, Huls), lauroyl macrogol-32 glyceride (GELUCIRE 44/14, Gattefosse), stearoyl macrogol glyceride (GELUCIRE 50/13, Gattefosse), mono, di, tri, tetra esters of vegetable oils and sorbitol (SorbitoGlyceride, Gattefosse), pentaerythrityl tetraisostearate (Crodamol PTIS, Croda), pentaerythrityl distearate (Albunol DS, Taiwan Surf.), pentaerythrityl tetraoleate (Liponate PO-4, Lipo Chem.), pentaerythrityl tetrastearate (Liponate PS-4, Lipo Chem.), pentaerythrityl tetracaprylate tetracaprate (Liponate PE-810, Lipo Chem.), and pentaerythrityl tetraoctanoate (Nilol Pentarate 408, NikLo) Also included as oils, are oil-soluble vitamins, such as vitamins A, D, E, K, etc. Derivatives of these vitamins, such as, tocopheryl PEG-1000 succinate (TPGS, available from Eastman), are also suitable surfactants for use in the compositions of the present application.

Polyglycerized fatty acids can also be used as excipients for the compositions provided herein. Commercially available polyglycerized fatty acids include: polyglyceryl-2 stearate (NikLol DGMS, Nikko), polyglyceryl-2 oleate (Nildol DGMO, Nildco), polyglyceryl-2 isostearate (Nikkol DGMIS, Nikko), polyglyceryl-3 oleate (Caprol 3GO, ABITEC), polyglyceryl-4 oleate (Nildol Tetraglyn 1-O, NikLo), polyglyceryl 4 stearate (NikLol Tetraglyn 1-S, Niliko), polyglyceryl-6 oleate (Drewpol 6-1 O, Stepan), polyglyceryl-10 laurate (Nildcol Decaglyn 1-L, Nikko), polyglyceryl-10 oleate (NikLol Decaglyn 1-O, Nildo), polyglyceryl-10 stearate (Nikkol Decaglyn 1-S, Nikko), polyglyceryl-6 ricinoleate (Nikkol Hexaglyn PR-15, Nikko), polyglyceryl-10 linoleate (Nikkol Decaglyn 1-LN, Nikko), polyglyceryl-6 pentaoleate (Nikkol Hexaglyn 5-O, Nikko), polyglyceryl-3 dioleate (Cremophor G032, BASF), polyglyceryl-3 distearate (Cremophor GS32, BASF), polyglyceryl-4 pentaoleate (Nikkol Tetraglyn 5-O, Nikko), polyglyceryl-6 dioleate (Caprol( ) 6G20, ABITEC), polyglyceryl-2 dioleate (Nikkol DGDO, Nikko), polyglyceryl-10 trioleate (Nikkol Decaglyn 3-O, Nikko), polyglyceryl-10 pentaoleate (Nikkol Decaglyn 5-O, Nikko), polyglyceryl-10 septaoleate (Nikkol Decaglyn 7-O, Nikko), polyglyceryl-10 tetraoleate (Caprol 1OG40, ABITEC), polyglyceryl-10 decaisostearate (Nikkol Decaglyn 10-IS, Nikko), polyglyceryl-101 decaoleate (Drewpol 10-10 O, Stepan), polyglyceryl-10 mono, dioleate (Caprol PGE 860, ABITEC), and polyglyceryl polyricinoleate (Polymuls, Henkel). Certain compositions of the application can include one or more of the polyglycerized fatty acids above.

In addition, propylene glycol fatty acid esters can be used as excipients for the compositions provided herein. Examples of commercially available propylene glycol fatty acid esters include: propylene glycol monocaprylate (Capryol 90, Gattefosse), propylene glycol monolaurate (Lauroglycol 90, Gattefosse), propylene glycol oleate (Lutrol OP2000, BASF), propylene glycol myristate (Mirpyl), propylene glycol monostearate (LIPO PGMS, Lipo Chem.), propylene glycol hydroxystearate, propylene glycol ricinoleate (PROPYMULS, Henkel), propylene glycol isostearate, propylene glycol monooleate (Myverol P-06, Eastman), propylene glycol dicaprylate dicaprate (Captex 200, ABITEC), propylene glycol dioctanoate (Captex 800, ABITEC), propylene glycol caprylate caprate (LABRAFAC PG, Gattefosse), propylene glycol dilaurate, propylene glycol distearate (Kessco PODS, Stepan), propylene glycol dicaprylate (Nikkol Sefsol 228, Nikko), and propylene glycol dicaprate (Nikkol PDD, Nikko). Certain compositions of the application can include one or more of the propylene glycol fatty acid esters above.

Mixtures of propylene glycol esters and glycerol esters can also be used as excipients for the compositions provided herein. One such mixture is composed of the oleic acid esters of propylene glycol and glycerol (ARLACEL 186). Examples of these surfactants include: oleic (ATMOS 300, ARLACEL 186, ICI), and stearic (ATMOS 150). Certain compositions of the application can include one or more of the mixtures of propylene glycol esters and glycerol esters above.

Further, mono- and diglycerides can be used as excipients for the compositions provided herein. Examples of commercially available mono- and diglycerides include: monopalmitolein (C16:1) (Larodan), monoelaidin (C18:1) (Larodan), monocaproin (C6) (Larodan), monocaprylin (Larodan), monocaprin (Larodan), monolaurin (Larodan), glyceryl monomyristate (C14) (Nilol MGM, Nikko), glyceryl monooleate (C18:1) (PECEOL, Gattefosse), glyceryl monooleate (Myverol, Eastman), glycerol monooleate/linoleate (OLICINE, Gattefosse), glycerol monolinoleate (Maisine, Gattefosse), glyceryl ricinoleate (Softigen 701, Huls), glyceryl monolaurate (ALDO MLD, Lonza), glycerol monopalmitate (Emalex GMS-P, Nihon), glycerol monostearate (Capmul GMS, ABITEC), glyceryl mono- and dioleate (Capmul GMO-K, ABITEC), glyceryl palmitic/stearic (CUTINA MD-A, ESTAGEL-G18), glyceryl acetate (Lamegin EE, Grunau GmbH), glyceryl laurate (Imwitor 312, Huls), glyceryl citrate/lactate/oleate/linoleate (Imwitor) 375, Huls), glyceryl caprylate (Imwitor 308, Huls), glyceryl caprylate/caprate (Capmul MCM, ABITEC), caprylic acid mono- and diglycerides (Imwitor 988, Huls), caprylic/capric glycerides (Imwitor 742, Huls), mono- and diacetylated monoglycerides (Myvacet 9-45, Eastman), glyceryl monostearate (Aldo MS, Arlacel 129, ICI), lactic acid esters of mono and diglycerides (LAMEGIN GLP, Henkel), dicaproin (C6) (Larodan), dicaprin (C10) (Larodan), dioctanoin (C8) (Larodan), dimyristin (C14) (Larodan), dipalmitin (C16) (Larodan), distearin (Larodan), glyceryl dilaurate (C12) (Capsule GDL, ABITEC), glyceryl dioleate (Capmul( ) GDO, ABITEC), glycerol esters of fatty acids (GELUCIRE 39/01, Gattefosse), dipalmitolein (C16:1) (Larodan), 1,2 and 1,3-diolein (C18:1) (Larodan), dielaidin (C18:1) (Larodan), and dilinolein (C18:2) (Larodan). Certain compositions of the application can include one or more of the mono- and diglycerides above.

Sterol and sterol derivatives can also be used as excipients for the compositions provided herein. Examples of commercially available sterol and sterol derivatives include: cholesterol, sitosterol, lanosterol, PEG-24 cholesterol ether (Solulan C-24, Amerchol), PEG-30 cholestanol (Phytosterol GENEROL series, Henkel), PEG-25 phytosterol (Nilol BPSH 25, Nikko), PEG-5 soyasterol (Nikkol BPS-5, Nilo), PEG-10 soyasterol (NikLol BPS-10, Niliko), PEG-20 soyasterol (Nikkol BPS-20, NikLo), and PEG-30 soyasterol (NikLol BPS-30, NikLo) Certain compositions of the application can include one or more of the sterol and sterol derivatives above.

Polyethylene glycol sorbitan fatty acid esters can also be used as excipients for the compositions provided herein. Examples of commercially available polyethylene glycol sorbitan fatty acid esters include: PEG-10 sorbitan laurate (Liposorb L-10, Lipo Chem.), PEG-20 sorbitan monolaurate (Tween 20, Atlas/ICI), PEG-4 sorbitan monolaurate (Tween) 21, Atlas/ICI), PEG-80 sorbitan monolaurate (Hodag PSML- 80, Calgene), PEG-6 sorbitan monolaurate (NikLol GL-1, NikLo), PEG-20 sorbitan monopalmitate (Tween 40, Atlas/ICI), PEG-20 sorbitan monostearate (Tween 60, Atlas/ICI), PEG-4 sorbitan monostearate (Tween (D 61, Atlas/ICI), PEG-8 sorbitan monostearate (DACOL MS S. Condea), PEG-6 sorbitan monostearate (Nikkol TS106, Nilo), PEG-20 sorbitan tristearate (Tween 65, Atlas/ICI), PEG-6 sorbitan tetrastearate (NikLol OS-6, Nildco), PEG-60 sorbitan tetrastearate (NikLol GS-460, Nikko), PEG-5 sorbitan monooleate (Tweed 81, Atlas/ICI), PEG-6 sorbitan monooleate (Nikkol TO 106, Nikko), PEG-20 sorbitan monooleate (Tweedy 80, Atlas/ICI), PEG-40 sorbitan oleate (Emalex ET 5040, Nihon Emulsion), PEG-20 sorbitan trioleate (Tweedy 85, Atlas/ICI), PEG-6 sorbitan tetraoleate (Nikkol GO-4, Nikko), PEG-30 sorbitan tetraoleate (Nikkol GO-430, Nikko), PEG-40 sorbitan tetraoleate (Nikkol GO-440, Nikko), PEG-20 sorbitan monoisostearate (Tween 120, Atlas/ICI), PEG sorbitol hexaoleate (Atlas G-1086, ICI), polysorbate 80 (Tweed 80, Pharma), polysorbate 85 (Tweed 85, Pharma), polysorbate 20 (Tween 20, Pharma), polysorbate 40 (Tween 40, Pharma), polysorbate 60 (Tween 60, Pharma), and PEG-6 sorbitol hexastearate (Nikkol OS-6, Nikko). Compositions of the application can include one or more of the polyethylene glycol sorbitan fatty acid esters above.

In addition, polyethylene glycol alkyl ethers can be used as excipients for the compositions described herein. Examples of commercially available polyethylene glycol alkyl ethers include: PEG-2 oleyl ether, oleth-2 (Brij 92/93, Atlas/ICI), PEG-3 oleyl ether, oleth-3 (Volpo 3, Croda), PEG-5 oleyl ether, oleth-5 (Volpo 5, Croda), PEG-10 oleyl ether, oleth-10 (Volpo 10, Croda), PEG-20 oleyl ether, oleth-20 (Volpo 20, Croda), PEG-4 lauryl ether, laureth-4 (Brij 30, Atlas/ICI), PEG-9 lauryl ether, PEG-23 lauryl ether, laureth-23 (Brij 35, Atlas/ICI), PEG-2 cetyl ether (Brij 52, ICI), PEG-10 cetyl ether (Brij 56, ICI), PEG-20 cetyl ether (BriJ 58, ICI), PEG-2 stearyl ether (Brij 72, ICI), PEG-10 stearyl ether (Brij 76, ICI), PEG-20 stearyl ether (Brij 78, ICI), and PEG-100 stearyl ether (Brij 700, ICI). Compositions of the application can include one or more of the polyethylene glycol alkyl ethers above.

Sugar esters can also be used as excipients for the compositions provided herein. Examples of commercially available sugar esters include: sucrose distearate (SUCRO ESTER 7, Gattefosse), sucrose distearate/monostearate (SUCRO ESTER 11, Gattefosse), sucrose dipalmitate, sucrose monostearate (Crodesta F-160, Croda), sucrose monopalmitate (SUCRO ESTER 15, Gattefosse), and sucrose monolaurate (Saccharose monolaurate 1695, Mitsubisbi-Kasei). Compositions of the application can include one or more of the sugar esters above.

Polyethylene glycol alkyl phenols are also useful as excipients for the compositions provided herein. Examples of commercially available polyethylene glycol alkyl phenols include: PEG-10-100 nonylphenol series (Triton X series, Rohm & Haas) and PEG-15-100 octylphenol ether series (Triton N-series, Rohm & Haas). Compositions of the application can include one or more of the polyethylene glycol alkyl phenols above.

Polyoxyethylene-polyoxypropylene block copolymers can also be used as excipients for the compositions provided herein. These surfactants are available under various trade names, including one or more of Synperonic PE series (ICI), Pluronic series (BASF), Lutrol (BASF), Supronic, Monolan, Pluracare, and Plurodac. The generic term for these copolymers is "poloxamer" (CAS 9003-11-6). These polymers have the formula shown below: $HO(C_2H_4O)_a (C_3H_6O)_b (C_2H_4O)_a$ H where "a" and "b" denote the number of polyoxyethylene and polyoxypropylene units, respectively. These copolymers are available in molecular weights ranging from 1000 to 15000 daltons, and with ethylene oxide/propylene oxide ratios between 0.1 and 0.8 by weight. Compositions of the application can include one or more of the polyoxyethylene-polyoxypropylene block copolymers above.

Polyoxyethylenes, such as PEG 300, PEG 400, and PEG 600, can be used as excipients for the compositions provided herein.

Sorbitan fatty acid esters can also be used as excipients for the compositions provided herein. Examples of commercially sorbitan fatty acid esters include: sorbitan monolaurate (Span-20, Atlas/ICI), sorbitan monopalmitate (Span-40, Atlas/ICI), sorbitan monooleate (Span-80, Atlas/ICI), sorbitan monostearate (Span-60, Atlas/ICI), sorbitan trioleate (Span-85, Atlas/ICI), sorbitan sesquioleate (Arlacel-C, ICI), sorbitan tristearate (Span-65, Atlas/ICI), sorbitan monoisostearate (Crill 6, Croda), and sorbitan sesquistearate (Nildcol SS-15, Nikko). Compositions of the application can include one or more of the sorbitan fatty acid esters above.

Esters of lower alcohols ($C_2$ to $C_4$) and fatty acids are suitable surfactants for use in the application. Examples of these surfactants include: ethyl oleate (Crodamol HO, Croda), isopropyl myristate (Crodamol IPM, Croda), isopropyl palmitate (Crodamol IPP, Croda), ethyl linoleate (Nilol VF-E, Nikko), and isopropyl linoleate (NikLol VF-IP, Nikko) Compositions of the application can include one or more of the lower alcohol fatty acid esters above.

In addition, ionic surfactants can be used as excipients for the compositions provided herein. Examples of useful ionic surfactants include: sodium caproate, sodium caprylate, sodium caprate, sodium laurate, sodium myristate, sodium myristolate, sodium palmitate, sodium palmitoleate, sodium oleate, sodium ricinoleate, sodium linoleate, sodium linolenate, sodium stearate, sodium lauryl sulfate (dodecyl), sodium tetradecyl sulfate, sodium lauryl sarcosinate, sodium dioctyl sulfosuccinate, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco chenodeoxycholate, sodium cholylsarcosinate, sodium N-methyl taurocholate, egg yolk phosphatides, hydrogenated soy lecithin, dimyristoyl lecithin, lecithin, hydroxylated lecithin, lysophosphatidylcholine, cardiolipin, sphingomyelin, phosphatidylcholine, phosphatidyl ethanolamine, phosphatidic acid, phosphatidyl glycerol, phosphatidyl serine, diethanolamine, phospholipids, polyoxyethylene-10 oleyl ether phosphate, esterification products of fatty alcohols or fatty alcohol ethoxylates, with phosphoric acid or anhydride, ether carboxylates (by oxidation of terminal OH group of, fatty alcohol ethoxylates), succinylated monoglycerides, sodium stearyl fumarate, stearoyl propylene glycol hydrogen succinate, mono/diacetylated tartaric acid esters of mono- and diglycerides, citric acid esters of mono-, diglycerides, glyceryl-lacto esters of fatty acids, acyl lactylates, lactylic esters of fatty acids, sodium stearoyl-2-lactylate, sodium stearoyl lactylate, alginate salts, propylene glycol alginate, ethoxylated alkyl sulfates, alkyl benzene sulfones, alpha-olefin sulfonates, acyl isethionates, acyl taurates, alkyl glyceryl ether sulfonates, sodium octyl sulfosuccinate, sodium undecylenamido-MEA-sulfosuccinate, hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (trialkylglycine), lauryl betaine (N-lauryl, N,N-dimethylglycine), and ethoxylated amines (polyoxyethylene-15 coconut amine). For simplicity, typical counter ions are provided above. It will be appreciated by one skilled in the art, however, that any bioacceptable counter ion can be used. For example, although the fatty acids are shown as sodium salts, other cationic counter ions can also be used, such as, for example, alkali metal cations or ammonium. Compositions of the application can include one or more of the ionic surfactants above.

The term "penetration enhancers" includes, but is not limited to, chloroform, methyl isobutyl ketone, monoethanolamine, tetradecylmethyl salfoxide, N-(2-Hydroxyethyl)pyrrolidone, dimethyl acetamide, tetrahydrofurfuryl alcohol, Clofibric acid amides, proteolytic enzymes, hexamethylene lauramide, terpenes and sesquiterpenes, alpha-bisbolol, d-limonene, and N,N-diethyl-m-toluamide. One of skill in the art will appreciate that certain penetration enhancers are also useful in the composition of the present invention as excipients.

Compositions

In one embodiment of the application, there is provided a stable pharmaceutical composition comprising a luliconazole type antifungal agent or a pharmaceutically acceptable salt thereof, wherein the antifungal agent comprises greater than about 5% by weight of the composition. In one aspect, the antifungal agent is greater than about 7% by weight of the composition. In another aspect, the antifungal agent is greater than about 10% by weight of the composition. In another aspect, the antifungal agent is from about 5% to about 12.5% by weight of the composition.

In one aspect of the application, there is provided a stable pharmaceutical composition comprising luliconazole or a luliconazole type antifungal agent or a pharmaceutically acceptable salt thereof wherein the antifungal agent comprises greater than about 5% by weight of the composition. In one aspect, the antifungal agent is greater than about 7% by weight of the composition. In another aspect, the antifungal agent is greater than about 10% by weight of the composition. In yet another aspect, the antifungal agent is from about 5% to about 12.5% by weight of the composition. In yet another aspect, the antifungal agent is about 10% by weight of the composition.

In another aspect, the composition is stable for at least 4 weeks. In another aspect, the composition is stable for at least 4 weeks at a temperature of about 4° C.

In another aspect, the compositions provided herein comprise at least one excipient selected from the group consisting of an alcohol, a ketone, a polar aprotic solvent and an ethylene glycol derivative. In one aspect, the compositions described herein comprise at least one excipient selected from the group consisting of an alcohol, a ketone, a polar aprotic solvent and an ethylene glycol derivative wherein the excipient is present in the composition in an amount provided in Table A. It is understood that the compositions may include more than one excipient selected from the group consisting of an alcohol, a ketone, a polar aprotic solvent and an ethylene glycol derivative, including more than one excipient of the same class (e.g., the composition may comprise two or more different alcohols, such as benzyl alcohol and ethanol). It is also understood that such compositions may comprise luliconazole in amounts described herein, including but not limited to from about any of 5 or 8 or 10 or 12 weight percent to about 15 weight percent; from about 5 weight percent to about any of 8 or 10 or 12 weight percent; from about 8 weight percent to about 12 weight percent; from about 9 weight percent to about 11 weight percent; about any of 5 or 8 or 10 or 12 or 15 weight percent; at least about any of 5 or 8 or 10 or 12 or 15 weight percent; at least 0.01 weight percent but not more than about 15 weight percent.

TABLE A

Exemplary Weight Percent of Certain Components (Excipients) for use in Luliconzole Formulations

| Formulation Component | Weight Percent of Component in Formulation |
|---|---|
| an alcohol (e.g., ethanol) | From about 20 to about 80; from about 25 to about 75; from about 30 to about 70; from about 35 to about 65; from about 30 or about 40 to about 60; from about 40 to about 50; from about 35 or about 45 to about 55; about any of 20 or 25 or 30 or 35 or 40 or 45 or 50 or 55 or 60 or 65 or 70 or 75 or 80 weight percent or more; and at least about any of 20 or 25 or 30 or 35 or 40 or 45 or 50 or 55 or 60 or 65 or 70 or 75 or 80 weight percent. |
| an alcohol (e.g., benzyl alcohol) | From 0.01 to about any of 2 or 4 or 6 or 8 or 10; from about any of 1 or 2 or 4 to about 10; from about 6 to about 10; from about 8 to about 10; about any of 1 or 2 or 3 or 4 or 5 or 6 or 7 or 8 or 9 or 10; at least about any of 1 or 2 or 3 or 4 or 5 or 6 or 7 or 8 or 9 or 10; at least 0.01 but not more than about any of 10 or 8 or 6 or 5 or 4 or 3 or 2 weight percent. |
| a ketone (e.g., acetone) | From 0.01 to about any of 5 or 10 or 15 or 20 or 25; from about 1 to about 20 or about 25; from about 5 to about 15 or about 25; from about 8 to about 15; from about 10 to about 15 or about 25; from about 11 to about 13; about any of 1 or 5 or 8 or 10 or 12 or 15 or 20 or 25; at least about any of 1 or 5 or 8 or 10 or 12 or 15 or 20 or 25; at least 0.01 but not more than about any of 25 or 20 or 15 or 10 or 5 weight percent. |
| a polar aprotic solvent (e.g., propylene carbonate) | From 0.01 to about any of 3 or 5 or 8 or 10 or 15 or 20; from about 1 to about 15 or about 20; from about 5 to about 20; from about 10 to about 20; from about 15 to about 20; from about 3 to about 8 or about 10; from about 4 to about 6; about any of about 1 or 3 or 5 or 8 or 10 or 12 or 15 or 20 or 25; at least about any of 1 or 3 or 5 or 8 or 10 or 12 or 15 or 20 or 25; at least 0.01 but not more than about 25 or 20 or 15 or 10 or 5 weight percent. |

TABLE A-continued

Exemplary Weight Percent of Certain Components
(Excipients) for use in Luliconzole Formulations

| Formulation Component | Weight Percent of Component in Formulation |
|---|---|
| ethylene glycol derivative. (e.g., a diethylene glycol monosubstituted ether of the formula HOCH$_2$CH$_2$OCH$_2$CH$_2$OR, where R is an alkyl group having 1-6 carbon atoms (e.g., ethyl)) | From about any of 1 or 10 or 20 or 30 or 40 to about 50; from about 1 to about any of 10 or 20 or 30 or 40; from about 10 to about 40; from about 15 to about 35; from about 20 or about 30; from about 20 to about 25; about any of 1 or 5 or 10 or 15 or 20 or 25 or 30 or 35 or 40 or 45 or 50; at least about any of or 5 or 10 or 15 or 20 or 25 or 30 or 35 or 40 or 45 or 50; at least 0.01 but not more than about any of 40 or 30 or 25 or 20 or 15 or 10 or 5 weight percent. |

It is understood that components of a luliconazole composition may be present in amounts that result in one or more advantageous properties as described herein. In one variation the amounts are as described in Table A. Thus, the pharmaceutical compositions described may comprise the formulation components in a weight percentage detailed herein, the same as if each and every combination of component and weight percent were specifically and individually listed. For example, in a luliconazole composition comprising at least one of an alcohol, a ketone, a polar aprotic solvent and an ethylene glycol derivative, in one aspect luliconazole is present in the composition in about 10 weight percent and the alcohol, ketone, polar aprotic solvent or an ethylene glycol derivative is present in an amount provided in Table A. In one aspect, a composition is provided wherein the composition comprises from about any of 5 or 8 or 10 or 12 weight percent to about 15 weight percent luliconazole and an alcohol (such as ethanol and/or benzyl alcohol) in an amount described in Table A. In a particular variation, the composition comprises both ethanol and benzyl alcohol. In one aspect, a composition is provided wherein the composition comprises from about any of 5 or 8 or 10 or 12 weight percent to about 15 weight percent luliconazole and a ketone (such as acetone, ethylmethyl ketone and isobutyl ketone) in an amount described in Table A. In one aspect, a composition is provided wherein the composition comprises from about any of 5 or 8 or 10 or 12 weight percent to about 15 weight percent luliconazole and a polar aprotic solvent (such as propylene carbonate, ethylene carbonate and glycerin carbonate) in an amount described in Table A. In a particular variation, the polar aprotic solvent is other than NMP. In one aspect, a composition is provided wherein the composition comprises from about any of 5 or 8 or 10 or 12 weight percent to about 15 weight percent luliconazole and an ethylene glycol derivative (such as diethylene glycol monoethyl ether) in an amount described in Table A.

In another aspect, the compositions provided herein comprise at least two excipients selected from the group consisting of an alcohol, a ketone, a polar aprotic solvent and an ethylene glycol derivative. It is understood that when at least two excipients selected from the group consisting of an alcohol, a ketone, a polar aprotic solvent and an ethylene glycol derivative are components of a luliconazole composition, such components may be present in amounts that result in one or more advantageous properties as described herein. In one variation the amounts are as described in Table A. Thus, the pharmaceutical compositions described may comprise two or more of an alcohol, a ketone, a polar aprotic solvent and an ethylene glycol derivative in a weight percentage detailed herein, the same as if each and every combination of component and weight percent were specifically and individually listed. For example, in a luliconazole composition comprising at least two of an alcohol, a ketone, a polar aprotic solvent and an ethylene glycol derivative, in one aspect luliconazole is present in the composition in about 10 weight percent and the two components selected from an alcohol, ketone, polar aprotic solvent or an ethylene glycol derivative are present in an amount provided in Table A. In one aspect, a composition is provided wherein the composition comprises from about any of 5 or 8 or 10 or 12 weight percent to about 15 weight percent luliconazole and two or more alcohols (such as ethanol and benzyl alcohol) in an amount described in Table A. In a particular variation, ethanol is provided in an amount specified in the first row of Table A and benzyl alcohol is provided in an amount specified in the second row of Table A. In one aspect, a composition is provided wherein the composition comprises from about any of 5 or 8 or 10 or 12 weight percent to about 15 weight percent luliconazole; and, in an amount described in Table A, a combination of excipients selected from: (i) an alcohol and a ketone; (ii) an alcohol and a polar aprotic solvent; (iii) an alcohol and an ethylene glycol derivative; (iv) a ketone and a polar aprotic solvent; (v) a ketone and an ethylene glycol derivative; and (vi) a polar aprotic solvent and an ethylene glycol derivative. In a particular variation, the alcohol is ethanol and/or benzyl alcohol; the ketone is acetone, ethylmethyl ketone and isobutyl ketone; the polar aprotic solvent is propylene carbonate, ethylene carbonate or glycerin carbonate and the ethylene glycol derivative is a diethyleneglycol monosubstituted ether of the formula HOCH$_2$CH$_2$OCH$_2$CH$_2$OR, where R is an alkyl group having 1-6 carbon atoms (e.g., ethyl). In a more particular variation, the alcohol is ethanol and/or benzyl alcohol; the ketone is acetone; the polar aprotic solvent is propylene carbonate and the ethylene glycol derivative is a diethyleneglycol monosubstituted ether of the formula HOCH$_2$CH$_2$OCH$_2$CH$_2$OR, where R is ethyl (diethyleneglycol monoethyl ether).

In another aspect, the compositions provided herein comprise at least three excipients selected from the group consisting of an alcohol, a ketone, a polar aprotic solvent and an ethylene glycol derivative. It is understood that when at least three excipients selected from the group consisting of an alcohol, a ketone, a polar aprotic solvent and an ethylene glycol derivative are components of a luliconazole composition, such components may be present in amounts that result in one or more advantageous properties as described herein. In one variation the amounts are as described in Table A. Thus, the pharmaceutical compositions described may comprise three or more of an alcohol, a ketone, a polar aprotic solvent and an ethylene glycol derivative in a weight percentage detailed herein, the same as if each and every combination of component and weight percent were specifically and individually listed. For example, in a luliconazole composition comprising at least three of an alcohol, a ketone, a polar aprotic solvent and an ethylene glycol derivative, in one aspect luliconazole is present in the composition in about 10 weight percent and the three components selected from an alcohol, ketone, polar aprotic solvent or an ethylene glycol derivative are present in an amount provided in Table A. In one aspect, a composition is provided wherein the composition comprises from about any of 5 or 8 or 10 or 12 weight percent to about 15 weight percent luliconazole and two or more alcohols (such as ethanol and benzyl alcohol) in an amount described in Table A. In a particular variation, ethanol is provided in an amount specified in the first row of Table A and benzyl alcohol is provided in an amount specified in the second row of Table A. In one aspect, a composition is provided wherein the composition comprises from about any of 5 or 8 or 10 or 12 weight percent to about 15 weight percent luliconazole; and, in any amount described in Table A, a combination of excipients selected from: (i) an alcohol, a ketone and a polar aprotic solvent; (ii) an alcohol, a ketone and an ethylene glycol derivative; (iii) an alcohol, a polar aprotic solvent and an ethylene glycol derivative; and (iv) a ketone, a polar aprotic solvent and an ethylene glycol derivative. In a particular variation, the alcohol is ethanol and/or benzyl alcohol; the ketone is acetone, ethylmethyl ketone and isobutyl ketone; the polar aprotic solvent is propylene carbonate, ethylene carbonate or glycerin carbonate and the ethylene glycol derivative is a diethyleneglycol monosubstituted ether of the formula $HOCH_2CH_2OCH_2CH_2OR$, where R is an alkyl group having 1-6 carbon atoms (e.g., ethyl). In a more particular variation, the alcohol is ethanol and/or benzyl alcohol; the ketone is acetone; the polar aprotic solvent is propylene carbonate and the ethylene glycol derivative is a diethyleneglycol monosubstituted ether of the formula $HOCH_2CH_2OCH_2CH_2OR$, where R is ethyl.

In another aspect, the compositions provided herein comprise each of the excipients selected from the group consisting of an alcohol, a ketone, a polar aprotic solvent and an ethylene glycol derivative. It is understood that when each of the excipients selected from the group consisting of an alcohol, a ketone, a polar aprotic solvent and an ethylene glycol derivative are components of a luliconazole composition, such components may be present in amounts that result in one or more advantageous properties as described herein. In one variation the amounts are as described in Table A. Thus, the pharmaceutical compositions described may comprise an alcohol, a ketone, a polar aprotic solvent and an ethylene glycol derivative in a weight percentage detailed herein, the same as if each and every combination of component and weight percent were specifically and individually listed. For example, in a luliconazole composition comprising each of an alcohol, a ketone, a polar aprotic solvent and an ethylene glycol derivative, in one aspect luliconazole is present in the composition in about 10 weight percent and the alcohol, ketone, polar aprotic solvent and ethylene glycol derivative are present in an amount provided in Table A. In one aspect, a composition is provided wherein the composition comprises from about any of 5 or 8 or 10 or 12 weight percent to about 15 weight percent luliconazole and two or more alcohols (such as ethanol and benzyl alcohol) in an amount described in Table A. In a particular variation, ethanol is provided in an amount specified in the first row of Table A and benzyl alcohol is provided in an amount specified in the second row of Table A. In one aspect, a composition is provided wherein the composition comprises from about any of 5 or 8 or 10 or 12 weight percent to about 15 weight percent luliconazole; and, in an amount described in Table A, each of an alcohol, a ketone a polar aprotic solvent and an ethylene glycol derivative. In a particular variation, the alcohol is ethanol and/or benzyl alcohol; the ketone is acetone, ethylmethyl ketone and isobutyl ketone; the polar aprotic solvent is propylene carbonate, ethylene carbonate or glycerin carbonate and the ethylene glycol derivative is a diethyleneglycol monosubstituted ether of the formula $HOCH_2CH_2OCH_2CH_2OR$, where R is an alkyl group having 1-6 carbon atoms (e.g., ethyl). In a more particular variation, the alcohol is ethanol and/or benzyl alcohol; the ketone is acetone; the polar aprotic solvent is propylene carbonate and the ethylene glycol derivative is a diethyleneglycol monosubstituted ether of the formula $HOCH_2CH_2OCH_2CH_2OR$, where R is ethyl.

In one embodiment, the luliconazole compositions (including but not limited to the compositions comprising at least one or two or three or each of an alcohol, a ketone, a polar aprotic solvent and an ethylene glycol derivative) further comprise a film forming agent, such as a maleic anhydride/methyl vinyl ether copolymer as described herein. In one aspect, the film forming agent is present in from 0.01 weight percent to about any of 1 or 2 or 4 or 6 or 8 or 10 weight percent or from about 5 to about 1 weight percent or from about 1 to about 3 weight percent or in about any of 0.5 or 1 or 2 or 3 or 5 weight percent or at least about any of 0.01 or 0.5 or 1 or 2 or 3 or 5.

In one embodiment, the luliconazole compositions (including but not limited to the compositions comprising at least one or two or three or each of an alcohol, a ketone, a polar aprotic solvent and an ethylene glycol derivative), and optionally a film forming agent, in one aspect is substantially anhydrous.

In another embodiment, the luliconazole compositions (including but not limited to the compositions comprising at least one or two or three or each of an alcohol, a ketone, a polar aprotic solvent and an ethylene glycol derivative), and optionally a film forming agent, in one aspect provide a clear solution without evidence of crystal formation upon visual inspection after 6 months of storage at any of 5° C., 25° C. and 40° C.

In another embodiment, the luliconazole compositions (including but not limited to the compositions comprising at least one or two or three or each of an alcohol, a ketone, a polar aprotic solvent and an ethylene glycol derivative), and optionally a film forming agent, in one aspect contain at least about 95% of the theoretical maximum amount of luliconazole after 6 months of storage at any of 5° C., 25° C. and 40° C.

In another embodiment, the luliconazole compositions (including but not limited to the compositions comprising at least one or two or three or each of an alcohol, a ketone, a polar aprotic solvent and an ethylene glycol derivative), and optionally a film forming agent, in one aspect provide a clear solution without evidence of crystal formation upon visual inspection after 6 months of storage at any of 5° C., 25° C. and 40° C. and contain at least about 95% of the theoretical maximum amount of luliconazole after 6 months of storage at any of 5° C., 25° C. and 40° C.

In another embodiment, the luliconazole compositions (including but not limited to the compositions comprising at least one or two or three or each of an alcohol, a ketone, a polar aprotic solvent and an ethylene glycol derivative), and optionally a film forming agent, in one exhibit efficacy against fungal infections, such as onychomycosis. In one aspect, the compositions provided herein eradicates at least 80% of a fungal infection of the nail after 14 days of treatment, as measured by the recovery of less than 20% of the theoretical amount of recoverable ATP from the fungus. Preferably, such compositions result in both high (e.g., greater than any of 80% or 85% or 90% or 95% or 98% or 100%) mycological cure and clinical cure rates.

In another embodiment, the luliconazole compositions (including but not limited to the compositions comprising at least one or two or three or each of an alcohol, a ketone, a polar aprotic solvent and an ethylene glycol derivative) and optionally a film forming agent, in one aspect the composition exhibits penetration through a nail, such as a toenail.

In another aspect, the alcohol is benzyl alcohol, ethanol or a combination thereof. In another aspect, the ethanol is from about 5% to about 80% by weight of the composition. In another aspect, the ethanol is from about 35% to about 60% by weight of the composition. In another aspect, the ethanol is from about 40% to about 48% by weight of the composition. In another aspect, the benzyl alcohol is from about 0.5% to about 50% by weight of the composition. In another aspect, the benzyl alcohol is from about 1% to about 15% by weight of the composition. In another aspect, the benzyl alcohol is from about 1% to about 6% by weight of the composition.

In another aspect, the ketone is acetone. In another aspect, the acetone is from about 0.5% to about 50% by weight of the composition. In another aspect, the acetone is from about 5% to about 15% by weight of the composition. In another aspect, the acetone is from about 10% to about 14% by weight of the composition.

In another aspect, the polar aprotic solvent is propylene carbonate. In another aspect, the propylene carbonate is from about 0.5% to about 50% by weight of the composition. In another aspect, the propylene carbonate is from about 5% to about 15% by weight of the composition. In another aspect, the propylene carbonate is from about 3% to about 7% by weight of the composition.

In another aspect, the ethylene glycol derivative is diethylene glycol monoethyl ether (such as Transcutol™ P). In another aspect the diethylene glycol monoethyl ether (such as Transcutol™ P) is from about 0.5% to about 70% by weight of the composition. In another aspect, the diethylene glycol monoethyl ether (such as Transcutol™ P) is from about 5% to about 30% by weight of the composition. In another aspect, the diethylene glycol monoethyl ether (such as Transcutol™ P) is from about 23% to about 27% by weight of the composition.

In another aspect, the compositions provided herein comprise about 10% of the antifungal agent, about 2% benzyl alcohol, about 12% acetone and about 25% diethylene glycol monoethyl ether (such as Transcutol™ P). In another aspect, the compositions provided herein comprise about 12.5% active agent, about 4% benzyl alcohol, about 12% acetone and about 25% diethylene glycol monoethyl ether (such as Transcutol™ P).

In another aspect, the antifungal agent is luliconazole. In another aspect, the antifungal agent is lanoconazole of the formula:

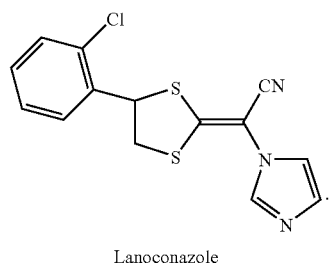

Lanoconazole (II)

In another aspect, luliconazole is about 10% by weight of the composition.

Embodiments that contain luliconazole can apply to lanoconazole.

In another aspect, the compositions provided herein comprise at least one excipient, or alternatively at least two excipients, or alternatively at least three excipients selected from the group consisting of an alcohol, a ketone, a polar aprotic solvent, an ethylene glycol derivative, an alpha hydroxyl acid or its salt, a diester of a dibasic acid, and a surface active agent.

In another aspect, the compositions provided herein comprise at least one excipient, or alternatively at least two excipients, or alternatively at least three excipients selected from the group consisting of an alcohol, a ketone, a polar aprotic solvent and an ethylene glycol derivative. Within this aspect, in certain other aspects, the compositions of the present application further comprise at least one excipient or alternatively at least two excipients selected from the group consisting of an alpha-hydroxy acid, a diester of a dibasic acid, and a surface active agent.

In another aspect, the compositions provided herein further comprise a film-forming agent. In another aspect, the film-forming agent is methylvinyl ether-maleic anhydride (Gantrez).

In another aspect, the compositions provided herein are gels or creams suitable for topical administration.

Certain excipients useful in the compositions of the present application are disclosed below.

Alcohols

In one aspect, the alcohol, useful as an excipient in the compositions of the present application, is ethyl alcohol selected from the group consisting of dehydrated ethyl alcohol, denatured ethyl alcohol, diluted ethyl alcohol (50% aqueous), SD alcohol 3a, SD alcohol 40, SD alcohol 40-2, SD alcohol 40b. As used herein, SD refers to specially denatured alcohol.

In another aspect, the alcohol is a short chain aliphatic alcohol. In another aspect, the short chain aliphatic alcohol is selected from the group consisting of butyl alcohol, isopropyl alcohol, methyl alcohol, phenoxyethanol and tert butyl alcohol. In another aspect, the alcohol is alpha-terpinol. In another aspect, the alcohol is a long chain fatty alcohol. In another aspect, the long chain fatty alcohol is selected from the group consisting of ceteryl alcohol, cetyl alcohol, docosanol, myristyl alcohol, oleyl alcohol, and stearyl alcohol. In another aspect, the alcohol is selected from alpha-tocopherol, amerchol CAB, chlorobutanol (3,3,3,-trichloromethyl-2,2-dimethylethanol), hydroxyethyl cellulose, hydroxymethyl cellulose, hydroxyoctacosanyl hydroxystearate, hydroxypropyl cellulose (e.g., Krucel® hydroxypropyl cellulose), isostearyl alcohol, menthol, N,N-bis(2-hydroxyethyl)stearamide, octyl hydroxystearate, sorbitol, N-(2-Hydroxyethyl)pyrrolidone, and tetrahydrofurfuryl alcohol. In another aspect, the alcohol is an amino alcohol. In another aspect, the amino alcohol is selected from the group consisting of 2-amino-2-methyl-1-propanol, diethanolamine, di-isopropanolamine, and mono-ethanolamine.

In another aspect, the alcohol used in the compositions of the present application is a $C_1$-$C_{25}$ alkanol. In another aspect, the alcohol is a $C_1$-$C_{12}$ alkanol. In another aspect, the alcohol is a $C_1$-$C_7$ alkanol. Within these aspects, the alcohol is a primary alcohol, a secondary alcohol, or a tertiary alcohol. The carbon backbone of the alkanol is optionally substituted with a phenyl, amino, alkoxy, phenoxy or a halo group. In another aspect, the alcohol used in the compositions of the present application has a formula $C_3$-$C_8$ cycloalkyl-OH or $C_3$-$C_8$ heterocyclyl-OH, provided that the hydroxyl group is not attached to a carbon atom that is attached to a heteroatom.

In another aspect, the alcohol is benzyl alcohol. In another aspect, the alcohol is 2,4-dichlorobenzyl alcohol.

In certain aspects, the content of alcohols in the pharmaceutical composition of the present application is about 5 to about 80%, about 10 to about 70%, about 20 to about 60%, about 30 to about 50%, about 35 to about 55%, or about 50%, by mass, with respect to the total amount of the pharmaceutical composition.

Ethylene Glycol Derivatives

In one aspect, the ethylene glycol derivative is a diol or a diol derivative selected from the group consisting of butylene glycol, dipropylene glycol, ethylene glycol, hexylene glycol, and propylene glycol. In another aspect, the ethylene glycol derivative is a diol derivative selected from the group consisting of diethylene glycol monomethyl ether, diethylene glycol monoethyl ether (such as Transcutol™), ethyl hexanediol, propylene glycol monolaurate, propylene glycol monostearate, propylene glycol palmitostearate and propylene glycol ricinoleate.

In one embodiment, the formulation comprises a diethylene glycol monosubstituted ether. In another embodiment, the diethylene glycol monosubstituted ether is a compound of the formula $HOCH_2CH_2OCH_2CH_2OR$, wherein R is selected from the group consisting of a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group and an alkynylacyl group, and combinations thereof. In another embodiment, R is a linear alkyl group having 1-6 carbon atoms or a branched alkyl group having 2-12 carbon atoms. In another embodiment, R is a linear alkyl group having 1-6 carbon atoms. In another embodiment, R is a linear alkyl group having 2 to 3 carbon atoms. In another embodiment, R is ethyl, which corresponds to ethoxy diglycol reagent (also known as diethylene glycol monoethyl ether and 2-(2-ethoxyethoxy)ethanol), shown below.

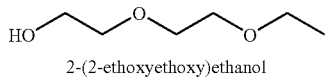

2-(2-ethoxyethoxy)ethanol

In another embodiment, the formulation comprises a polyoxylglyceride. In one embodiment, the polyoxylglyceride is a caprylocaproyl, linoleoyl, oleoyl, lauroyl, or stearoyl polyoxylglyceride. In another embodiment, the polyoxylglyceride is lauroyl polyoxyl-32 glycerides, stearoyl polyoxyl-32 glycerides, medium chain triglycerides, oleoyl polyoxyl-6 glycerides, linoleoyl polyoxyl-6 glycerides, lauroyl polyoxyl-6 glycerides, or caprylocaproyl polyoxyl-8-glycerides. Such polyoxylglycerides are available from Gattefosse (Canada) under the tradenames Labrasol, Labrafil, and Gelucire.

In yet another aspect, the ethylene glycol derivative is a polyol selected from the group consisting of glycerin, glyceryl acetate, glyceryl citrate, glyceryl isostearate, glyceryl laurate, glyceryl monostearate, glyceryl oleate, glyceryl palmitate, glyceryl ricinoleate, glyceryl stearate-laureth-23, glyceryl stearate SE, glyceryl stearate/PEG-100 stearate and 1,2,6-hexanetriol.

In another aspect, the ethylene glycol derivative has the formula R-alkylene-R or R-heteroalkylene-R wherein R is selected from the group consisting of hydroxy, alkoxy, phenoxy, alkylcarbonyloxy and arylcarbonyloxy, and wherein the alkylene or heteroalkylene moiety is optionally substituted with a hydroxyl, alkoxy, phenoxy, alkylcarbonyloxy and arylcarbonyloxy group, provided however that, 2 heteroatoms (for example, 2 oxygen atoms) are not attached to the same carbon atom. Within this aspect, the alkylene moiety is $C_1$-$C_7$ alkylene, $C_1$-$C_5$ alkylene, or $C_1$-$C_3$ alkylene. In another related aspect, the heteroalkylene moiety is $C_1$-$C_7$ heteroalkylene, $C_1$-$C_5$ heteroalkylene or $C_1$-$C_3$ heteroalkylene.

In another aspect, the ethylene glycol derivative is a polyethylene glycol (PEG) moiety selected from the group consisting of polyethylene glycol 1000, polyethylene glycol 1500, polyethylene glycol 1540, polyethylene glycol 200, polyethylene glycol 300, polyethylene glycol 300-1600, polyethylene glycol 3350, polyethylene glycol 400, polyethylene glycol 4000, polyethylene glycol 540, polyethylene glycol 600, polyethylene glycol 6000, polyethylene glycol 8000, polyethylene glycol 900, polyoxyethylene-polyoxypropylene 1800 and polyoxyethylene alcohols.

In another aspect, the ethylene glycol derivative is a PEG derivative selected from the group consisting of ceteth-2, ceteth-10, ceteth-20, ceteth-23, dimethicone copolyol, PEG 6-32 stearate/glycol stearate, PEG-22 methyl ether/dodecyl glycol copolymer, PEG-25 propylene glycol stearate, PEG-45/dodecyl glycol copolymer, peglicol-5-oleate, pegoxol 7 stearate, PPG-12/SMDI copolymer, polypropylene glycol (PPG)-15 stearyl ether, PPG-20 methyl glucose ether distearate, PPG-26 oleate, steareth-10, steareth-100, steareth-2, steareth-20 and steareth-21.

In another aspect, the ethylene glycol derivative is a PEG derivative selected from the group consisting of poloxamer 124, poloxamer 181, poloxamer 182, poloxamer 188, poloxamer 237, poloxamer 407, polyoxyethylene fatty acid esters, polyoxyethylene propylene, methoxypolyoxyethylene glycol 350 and tyloxapol.

In another aspect, the ethylene glycol derivative is a PEG derivative selected from nonoxynol-15, nonoxynol-15, nonoxynol-9, octoxynol-1 and octoxynol-9.

In another aspect, the ethylene glycol derivative is a PEG derivative selected from polyoxyl 100 glyceryl stearate, polyoxyl 100 stearate, polyoxyl 15 cocamine, polyoxyl 150 distearate, polyoxyl 2 stearate, polyoxyl 4 dilaurate, polyoxyl 40 hydrogenated castor oil, polyoxyl 40 stearate, polyoxyl 400 stearate, polyoxyl 50 stearate, polyoxyl 6 and polyoxyl 32 palmitostearate, polyoxyl 6 isostearate, polyoxyl 60 hydrogenated castor oil, polyoxyl 75 lanolin, polyoxyl 8 laurate, polyoxyl 8 stearate, polyoxyl distearate, polyoxyl glyceryl stearate, polyoxyl lanolin and polyoxyl stearate.

In certain aspects, the content of ethylene glycol derivatives in the pharmaceutical composition of the present application is about 1 to about 50%, about 5 to about 45%, about 10 to about 40%, about 15 to about 35%, about 20 to about 30%, or about 25%, by mass, with respect to the total amount of the pharmaceutical composition.

Ketones

In another aspect, the ketone is selected from the group consisting of acetone, ethyl methyl ketone and methyl isobutyl ketone.

In certain aspects, the content of alcohols in the pharmaceutical composition of the present application is about 1 to about 40%, about 5 to about 35%, about 10 to about 30%, or about 15%, by mass, with respect to the total amount of the pharmaceutical composition.

Polar Aprotic Solvents

In another aspect, the polar aprotic solvent is selected from the group consisting of propylene carbonate, ethylene carbonate, and glycerin carbonate. In another aspect, the polar aprotic solvent is selected from the group consisting of N-methylpyrrolidone, dimethyl acetamide and DMSO.

In certain aspects, the content of alcohols in the pharmaceutical composition of the present application is about 1 to about 50%, about 2 to about 40%, about 3 to about 30%, about 4 to about 20%, or about 5 to about 10%, by mass, with respect to the total amount of the pharmaceutical composition.

Alpha-Hydroxycarboxylic Acids and their Salts

In certain other aspects, the alpha-hydroxycarboxylic acid is an alpha-hydroxycarboxylic acid having from 2 to 25, from 5 to 20, from 10 to 15, and from 2 to 5 carbon atoms. The alkylene backbone of such acids can be suitably substituted. Suitable substituents include, without limitation, alkoxy, amino, halo, hydroxy and phenoxy groups. In another aspect, the alpha-hydroxycarboxylic acid is selected from lactic acid, glycolic acid and malic acid. Salts of the alpha-hydroxycarboxylic acids include, without limitation, sodium salt and potassium salt; alkaline earth metal salts, such as calcium salt and magnesium salt; amine salts, such as ammonium salt, triethylamine salt, and triethanol amine salt; and basic amino acid salts, such as arginine salt and lysine salt.

In certain aspects, the content of alpha-hydroxycarboxylic acids in the pharmaceutical composition of the present application is about 0.1 to about 20% by mass, or about 1 to about 10% by mass, with respect to the total amount of the pharmaceutical composition.

In certain other aspects, the mass ratio of alpha-hydroxycarboxylic acid or its salt to luliconazole or luliconazole type antifungal agent is about 0.1 to about 10, about 0.5 to about 5, or about 0.8 to 2.

Diesters of Dibasic Acids

In certain aspects, the diesters of dibasic acids comprise, as part of the ester moiety, alcohols having from 1 to 25, from 5 to 20, from 10 to 15, and from 1 to 4 carbon atoms. In certain other aspects, the alcohol useful as part of the diester of a dibasic acid is selected from the group consisting of methyl alcohol, ethyl alcohol, propyl alcohol, isopropyl alcohol, butyl alcohol, isobutyl alcohol and tert-butyl alcohol. Any polyol, such as an ethylene glycol and a propylene glycol can be used as the alcohol having 1 to 4 carbon atoms.

In certain aspect, the dibasic acids are those having from 1 to 25, from 5 to 20, from 10 to 15, and from 1 to 10 carbon atoms. In certain other aspects, the dibasic acid is selected from the group consisting of adipic acid, sebacic acid, oxalic acid and carbonic acid. In another aspect, a diester of the dibasic acid is selected from the group consisting of diethyl adipate, di-isopropyl adipate, diethyl sebacate, and di-isopropyl sebacate.

In certain aspects, the overall content of the diesters of dibasic acids used in the compositions of the invention is about 1 to about 30% by mass or about 5 to about 15% by mass, with respect to the total amount of the pharmaceutical composition.

One of skilled in the art, upon this disclosure will appreciate that penetration enhancers are useful in the compositions of the present invention in accordance with the present invention.

Film-forming agents are also useful in the practice of the present invention, including for example maleic anhydride/methyl vinyl ether copolymers such as Gantrez copolymers sold by Internationals Specialty Products (Wayne, N.J.), as well as the ethyl, isopropyl, and butyl esters of these copolymers, and maleic anhydride/butyl vinyl ether copolymers. Hydroxyalkylcellulose polymers, such as Krucel® hydroxypropyl cellulose sold by Hercules Incorporated (Wilmington, Del.) may also be used as a film-forming agent.

Certain compositions of the present invention are tabulated below.

While the compositions tabulated below include luliconazole as the antifungal agent, one of ordinary skill in the art will appreciate, upon reading this disclosure, that similar compositions including lanoconazole instead of luliconazole is within the scope of the present invention. Although grades of components are indicated in some variations, it is understood that other grades may be used. In addition, although Transcutol™ P is referred to in certain instances, such as the tables below, it is understood that compositions comprising diethylene glycol monoethyl ether may be used. In addition, although Gantez is referred to in certain instances, it is understood that compositions comprising butyl ester of PVM/MA copolymer may be used (such as butyl ester of PVM/MA copolymer, 38-52% isopropyl alcohol, <10% butyl alcohol). In addition, it is understood that reference to Alcohol (200 Proof) includes and intends ethanol.

TABLE 1a

| Ingredients | % wt/wt | % wt/wt | % wt/wt | % wt/wt | % wt/wt | % wt/wt | % wt/wt | % wt/wt | % wt/wt | % wt/wt |
|---|---|---|---|---|---|---|---|---|---|---|
| Ethanol (200 Proof) USP | 5-80 | 10-70 | 20-60 | 35-45 | 40-50 | 40-50 | 40-50 | 40-48 | 45-47 | 40-42 |
| Benzyl alcohol, USP | 0.5-50 | 0.5-40 | 0.5-30 | 1-15 | 1-10 | 1-10 | 1-10 | 1-6 | 1-3 | 3-6 |
| Propylene Carbonate NF | 0.5-50 | 0.5-40 | 0.5-30 | 5-15 | 5-10 | 5-10 | 5-10 | 3-7 | 4-6 | 4-6 |
| Acetone NF | 0.5-50 | 0.5-40 | 0.5-30 | 5-15 | 5-10 | 5-10 | 5-10 | 10-14 | 11-13 | 11-13 |
| Transcutol™ P | 0.5-70 | 0.5-60 | 0.5-50 | 5-30 | 10-30 | 15-30 | 20-30 | 23-27 | 24-26 | 24-26 |
| Luliconazole | 5-15 | 5-15 | 5-15 | 5-15 | 6-13 | 8-12 | 9-11 | 10-13 | 9-11 | 11-13 |

TABLE 2a

| Ingredients | % wt/wt | % wt/wt | % wt/wt | % wt/wt | % wt/wt | % wt/wt |
|---|---|---|---|---|---|---|
| Ethanol (200 Proof) USP | 40-50 | 40-50 | 40-50 | 40-50 | 40-50 | 40-50 |
| Benzyl alcohol, USP | 1-10 | 1-10 | 1-10 | 1-10 | 1-10 | 1-10 |
| Propylene Carbonate NF | 5-10 | 5-10 | 5-10 | 5-10 | 5-10 | 5-10 |
| Acetone NF | 5-10 | 5-10 | 5-10 | 5-10 | 5-10 | 5-10 |

TABLE 2a-continued

| Ingredients | % wt/wt | % wt/wt | % wt/wt | % wt/wt | % wt/wt | % wt/wt |
|---|---|---|---|---|---|---|
| Transcutol ™ P | 15-30 | 15-30 | 15-30 | 20-25 | 20-25 | 20-25 |
| Luliconazole | 8-12 | 8-12 | 8-12 | 9-11 | 9-11 | 9-11 |
| Alpha-hydroxycarboxylic acids or their salts | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 |

TABLE 3a

| Ingredients | % wt/wt | % wt/wt | % wt/wt | % wt/wt | % wt/wt | % wt/wt |
|---|---|---|---|---|---|---|
| Ethanol (200 Proof) USP | 5-80 | 5-80 | 5-80 | 40-50 | 40-50 | 40-50 |
| Benzyl alcohol, USP | 0.5-50 | 0.5-50 | 0.5-50 | 1-10 | 1-10 | 1-10 |
| Propylene Carbonate NF | 0.5-50 | 0.5-50 | 0.5-50 | 5-10 | 5-10 | 5-10 |
| Acetone NF | 0.5-50 | 0.5-50 | 0.5-50 | 5-10 | 5-10 | 5-10 |
| Transcutol ™ P | 0.5-70 | 0.5-70 | 0.5-70 | 10-30 | 10-30 | 10-30 |
| Luliconazole | 6-15 | 6-15 | 6-15 | 6-13 | 6-13 | 6-13 |
| Alpha-hydroxycarboxylic acids or their salts | 0.1-20 | 0.1-20 | 5-15 | 0.1-20 | 0.1-20 | 5-15 |
| Diesters of dibasic acids | 1-30 | 5-15 | 5-15 | 1-30 | 5-15 | 5-15 |

TABLE 4a

| Ingredients | % wt/wt | % wt/wt | % wt/wt | % wt/wt | % wt/wt | % wt/wt | % wt/wt | % wt/wt | % wt/wt |
|---|---|---|---|---|---|---|---|---|---|
| Ethanol (200 Proof) USP | 10-70 | 10-70 | 10-70 | 20-60 | 20-60 | 20-60 | 35-45 | 35-45 | 35-45 |
| Benzyl alcohol, USP | 0.5-40 | 0.5-40 | 0.5-40 | 0.5-30 | 0.5-30 | 0.5-30 | 1-15 | 1-15 | 1-15 |
| Propylene Carbonate NF | 0.5-40 | 0.5-40 | 0.5-40 | 0.5-30 | 0.5-30 | 0.5-30 | 5-15 | 5-15 | 5-15 |
| Acetone NF | 0.5-40 | 0.5-40 | 0.5-40 | 0.5-30 | 0.5-30 | 0.5-30 | 5-15 | 5-15 | 5-15 |
| Transcutol ™ P | 0.5-60 | 0.5-60 | 0.5-60 | 0.5-50 | 0.5-50 | 0.5-50 | 5-30 | 5-30 | 5-30 |
| Luliconazole | 5-15 | 5-15 | 5-15 | 5-15 | 5-15 | 5-15 | 5-15 | 5-15 | 5-15 |
| Alpha-hydroxycarboxylic acids or their salts | 0.1-20 | 0.1-20 | 1-10 | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 | 1-30 | 5-15 | 5-15 |

TABLE 5a

| Ingredients | % wt/wt | % wt/wt | % wt/wt | % wt/wt | % wt/wt | % wt/wt | % wt/wt | % wt/wt | % wt/wt |
|---|---|---|---|---|---|---|---|---|---|
| Ethanol (200 Proof) USP | 40-48 | 40-48 | 40-48 | 45-47 | 45-47 | 45-47 | 40-42 | 40-42 | 40-42 |
| Benzyl alcohol, USP | 1-6 | 1-6 | 1-6 | 1-3 | 1-3 | 1-3 | 3-6 | 3-6 | 3-6 |
| Propylene Carbonate NF | 3-7 | 3-7 | 3-7 | 4-6 | 4-6 | 4-6 | 4-6 | 4-6 | 4-6 |
| Acetone NF | 10-14 | 10-14 | 10-14 | 11-13 | 11-13 | 11-13 | 11-13 | 11-13 | 11-13 |
| Transcutol ™ P | 23-27 | 23-27 | 23-27 | 24-26 | 24-26 | 24-26 | 24-26 | 24-26 | 24-26 |
| Luliconazole | 10-13 | 10-13 | 10-13 | 9-11 | 9-11 | 9-11 | 11-13 | 11-13 | 11-13 |
| Alpha-hydroxycarboxylic acids or their salts | 0.1-20 | 0.1-20 | 1-10 | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 | 1-30 | 5-15 | 5-15 |

TABLE 6a

| Ingredients | % wt/wt | % wt/wt | % wt/wt | % wt/wt | % wt/wt | % wt/wt |
|---|---|---|---|---|---|---|
| Alcohol other than benzyl alcohol | 40-50 | 40-50 | 40-50 | 40-50 | 40-50 | 40-50 |
| Benzyl alcohol, USP | 1-10 | 1-10 | 1-10 | 1-10 | 1-10 | 1-10 |
| Polar aprotic solvent | 5-10 | 5-10 | 5-10 | 5-10 | 5-10 | 5-10 |
| Ketone | 5-10 | 5-10 | 5-10 | 5-10 | 5-10 | 5-10 |
| Ethylene glycol derivative | 15-30 | 15-30 | 15-30 | 20-25 | 20-25 | 20-25 |
| Luliconazole | 8-12 | 8-12 | 8-12 | 9-11 | 9-11 | 9-11 |
| Alpha-hydroxycarboxylic acids or their salts | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 |

TABLE 7a

| Ingredients | % wt/wt | % wt/wt | % wt/wt | % wt/wt | % wt/wt | % wt/wt |
|---|---|---|---|---|---|---|
| Alcohol other than benzyl alcohol | 5-80 | 5-80 | 5-80 | 40-50 | 40-50 | 40-50 |
| Benzyl alcohol, USP | 0.5-50 | 0.5-50 | 0.5-50 | 1-10 | 1-10 | 1-10 |
| Polar aprotic solvent | 0.5-50 | 0.5-50 | 0.5-50 | 5-10 | 5-10 | 5-10 |
| Ketone | 0.5-50 | 0.5-50 | 0.5-50 | 5-10 | 5-10 | 5-10 |
| Ethylene glycol derivative | 0.5-70 | 0.5-70 | 0.5-70 | 10-30 | 15-30 | 20-30 |
| Luliconazole | 6-15 | 6-15 | 6-15 | 6-13 | 6-13 | 6-13 |
| Alpha-hydroxycarboxylic acids or their salts | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 |

TABLE 8a

| Ingredients | % wt/wt | % wt/wt | % wt/wt | % wt/wt | % wt/wt | % wt/wt | % wt/wt | % wt/wt | % wt/wt |
|---|---|---|---|---|---|---|---|---|---|
| Alcohol other than benzyl alcohol | 10-70 | 10-70 | 10-70 | 20-60 | 20-60 | 20-60 | 35-45 | 35-45 | 35-45 |
| Benzyl alcohol, USP | 0.5-40 | 0.5-40 | 0.5-40 | 0.5-30 | 0.5-30 | 0.5-30 | 1-15 | 1-15 | 1-15 |
| Polar aprotic solvent | 0.5-40 | 0.5-40 | 0.5-40 | 0.5-30 | 0.5-30 | 0.5-30 | 5-15 | 5-15 | 5-15 |
| Ketone | 0.5-40 | 0.5-40 | 0.5-40 | 0.5-30 | 0.5-30 | 0.5-30 | 5-15 | 5-15 | 5-15 |
| Ethylene glycol derivative | 0.5-60 | 0.5-60 | 0.5-60 | 0.5-50 | 0.5-50 | 0.5-50 | 5-30 | 5-30 | 5-30 |
| Luliconazole | 5-15 | 5-15 | 5-15 | 5-15 | 5-15 | 5-15 | 5-15 | 5-15 | 5-15 |
| Alpha-hydroxycarboxylic acids or their salts | 0.1-20 | 0.1-20 | 1-10 | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 | 1-30 | 5-15 | 5-15 |

TABLE 9a

| Ingredients | % wt/wt | % wt/wt | % wt/wt | % wt/wt | % wt/wt | % wt/wt | % wt/wt | % wt/wt | % wt/wt |
|---|---|---|---|---|---|---|---|---|---|
| Alcohol other than benzyl alcohol | 40-48 | 40-48 | 40-48 | 45-47 | 45-47 | 45-47 | 40-42 | 40-42 | 40-42 |
| Benzyl alcohol, USP | 1-6 | 1-6 | 1-6 | 1-3 | 1-3 | 1-3 | 3-6 | 3-6 | 3-6 |
| Polar aprotic solvent | 3-7 | 3-7 | 3-7 | 4-6 | 4-6 | 4-6 | 4-6 | 4-6 | 4-6 |
| Ketone | 10-14 | 10-14 | 10-14 | 11-13 | 11-13 | 11-13 | 11-13 | 11-13 | 11-13 |
| Ethylene glycol derivative | 23-27 | 23-27 | 23-27 | 24-26 | 24-26 | 24-26 | 24-26 | 24-26 | 24-26 |
| Luliconazole | 10-13 | 10-13 | 10-13 | 9-11 | 9-11 | 9-11 | 11-13 | 11-13 | 11-13 |
| Alpha-hydroxycarboxylic acids or their salts | 0.1-20 | 0.1-20 | 1-10 | 0.1-20 | 0.1-20 | 1-10 | 0.1-20 | 0.1-20 | 1-10 |
| Diesters of dibasic acids | 1-30 | 5-15 | 5-15 | 1-30 | 5-15 | 5-15 | 1-30 | 5-15 | 5-15 |

In another embodiment of the application, there is provided a method for treating or ameliorating a disease comprising the topical administration of a composition provided herein. In one aspect, the disease treated is dermatomycosis or an onychomycosis. In another aspect, the disease treated is selected from the group consisting of Tinea corporis, Tinea cruris, Tinea pedis and Tinea unguium. In one aspect, the individual is a mammal, such as a human. In a particular aspect, the individual is a human and the methods provided are directed to treating a human nail.

All references throughout, such as publications, patents, patent applications and published patent applications, are incorporated herein by reference in their entireties.

The following examples are provided to illustrate, but not to limit the invention.

Experimental

The following procedures may be employed for the preparation of exemplary compositions of the present application. The starting materials and reagents used in preparing these compounds are either available from commercial suppliers such as the Sigma Aldrich Chemical Company (Milwaukee, Wis.) and Bachem (Torrance, Calif.).

EXAMPLES

Example 1

Determination of Solubility of Luliconazole in Different Solvents Suitable for Topical Formulations A study was performed to determine the solubility of luliconazole in various solvents that have been listed in the FDA inactive ingredients (IIG) database as approved drug products for topical formulations.

Materials and Methods

The solvents selected for the study along with their maximum potencies for use in a topical drug product, as listed in the FDA-IIG database, are given in Table 1B. Luliconazole (lot#08LLCZ28) was used as supplied by Nichino Service Co. (Japan).

TABLE 1B

Solvents used in the current study and their maximum potencies in topical formulations.

| Solvents | Sources | Maximum potency listed in FDA IIG database for topical formulation |
|---|---|---|
| Acetone, NF | DPT part# 150000 | 12.69% (solution) |
| Ethanol, USP (200 proof) | DPT part#160475 | 91% (solution) |
| Ethyl acetate | Fisher Scientific, part# E195-1 | 31% (solution) |
| Propylene carbonate, NF | Huntsman, #JSPCNFS1 | 5% (ointment) |
| Benzyl alcohol, USP | DPT part #710400 | 50% (gel), 2% (solution) |
| Transcutol ™ P (diethylene glycol monoethyl ether) | Gattefosse, lot#450647011 | 25% (gel) |
| Isopropyl alcohol, USP | DPT part# 153230 | 51.5% (solution) |
| Isopropyl myristate, NF | DPT part# 153250 | 10% (gel), 35% (ointment) |

Two model formulations were prepared for solubility studies with luliconazol at 5%, which was the target strength for the initial formulation. Details of the formulations are given in Tables 2 and 3.

TABLE 2

Model formulation-1
Model Formula 802-1215A04 (luliconazole at 5.1%)

| Ingredients | % wt/wt |
|---|---|
| 3% Stock solution in Ethanol (200 proof) (802-1215A01) | 50 |
| 6% Stock solution in Ethyl acetate (802-1215A02) | 30 |
| 15% Stock solution in Acetone (802-1215A03) | 12 |
| Benzyl alcohol, USP | 2 |
| Transcutol ™ P | 6 |

Stock solutions of luliconazole were prepared separately in ethanol (at 3%, wt/wt), ethyl acetate (at 6%, wt/wt) and in acetone (at 15%, wt/wt). The three stock solutions were mixed together with benzyl alcohol and Transcutol™ P at the compositions (% wt/wt) shown in Table 2 to obtain a clear solution of luliconazole at 5.1%.

TABLE 3

Model formulation-2
Model Formula 802-1219A01 (luliconazole at 5%)

| Ingredients | % wt/wt |
|---|---|
| luliconazole | 5 |
| Benzyl alcohol, USP | 14 |
| Ethanol, USP (200 proof) | 50 |
| Propylene carbonate, NF | 5 |
| Transcutol ™ P | 20 |
| Acetone, NF | 6 |

Formula 802-1219A01 was prepared by completely dissolving luliconazole in benzyl alcohol followed by addition of the solvents shown in Table 3 and mixed until uniform. A clear solution of luliconazole at 5% was obtained and was then stored in tightly closed screw-cap glass vials at room temperature (RT) and at 4° C.

Solubility Sample Preparation

Typically, luliconazole was weighed into a screw-cap glass vial, the desired solvent was added and the vial was tightly closed. The vials containing suspension were sonicated in an ultra-sonicator bath at 40° C. for 20-30 seconds; the vials were taken out of the bath and swirled to mix the contents. The sonication and swirling steps were repeated 3-4 times till most of the luliconazole was dissolved. Based on the pilot studies on solubility, 5-50% (wt/wt) luliconazole was suspended in different solvents. Visual observations revealed that luliconazole was completely soluble in benzyl alcohol at ~40% and in Transcutol™ P at ~15% therefore, saturated solutions of luliconazole in benzyl alcohol (at 50%) and in Transcutol™ P (at 20%) were prepared. The samples were stored at RT (21.5° C., ±1.5) and at 4° C. in tightly closed screw-cap glass vials. Sample preparation was conducted in a dark room under yellow light and samples were protected from light during storage. The solutions generally showed a few floating dust like particles that may have come from solvent or solute.

Determination of Solubility

Solubility was determined after 24 hours and again after 3 days at respective storage conditions (RT and 4° C.) using a UV spectrophotometer (Pharma Spec 1700; Shimadzu). Samples for quantitative determination of solubility were drawn from the supernatant area of the suspension (solution) into a 3 ml syringe with a 0.1 μm (pore size) syringe filter (nylon, 13 mm) attached. The desired amount of solution was delivered into a 100 ml volumetric flask that was immediately closed tightly with a stopper and weighed accurately to determine the exact weight of the solution. As ethyl acetate is incompatible with the plastic in the syringe and the housing of the syringe-filter, the ethyl acetate solution was centrifuged at 4200 rpm for 5 minutes and the supernatant solution was drawn for analysis using a glass Pasteur pipette.

The samples taken in volumetric flasks were diluted with methanol to the mark and diluted further before analyzing on the UV spectrophotometer. A five point standard curve of luliconazole (at 20, 10, 6, 4 and 2 µg/ml) in methanol was determined by reading the absorbance at 296 nm. The samples were also read at 296 nm and the concentration of luliconazole was determined from the equation of the standard curve. The solubility of luliconazole in respective solvents and model formulations was then determined as % wt/wt. Triplicate sample preparations (for spectrophotometric analysis) were achieved for each of the eight solvents and for the two model formulations (both stored at RT and 4° C. for 24 hrs and 3 days).

Solubility was calculated as % wt/wt from the UV spectrophotometric data read at 296 nm. Calculated solubility at 4° C. and RT both after 24 hours and 3 days storage are shown in Table 4.

Data in Table 4 shows that at room temperature benzyl alcohol has maximum solubility (43%, wt/wt) for luliconazole followed by acetone and Transcutol™ P (both about 16%). Propylene carbonate, and ethyl acetate both showed about 7% solubility whereas ethanol showed about 3.5% solubility. Isopropyl alcohol and isopropyl myristate showed 1.2% and 0.4% solubility respectively which are quite low compared to the other solvents. Both model formulations showed luliconazole at ~5.1% which was the theoretical concentration as well as the target strength in the formulas. Model formula #2 (802-1219A01) stored at 4° C. for 3 days also showed luliconazole at 5% and visual observations showed no crystallization suggesting that the luliconazole is soluble in the model formula (802-1219A01) at the target strength (of 5%) at 4° C.

Data in Table 4 shows that theoretical concentration of luliconazole matched quite well with the solutions that showed no visual crystallization suggesting that all of the luliconazole was in solution and was stable. However, since all analyses were performed by UV spectrophotometer at 296 nm, any degradation products of luliconazole that also have an absorption at 296 nm, would not be distinguished from

TABLE 4

Solubility (% wt/wt) of luliconazole in various solvents and in two model formulations is shown at 4° C. and RT (21.5° C., ±1.5) after 24 hrs and 3 days of storage. Data shown below is an average of triplicate sample preparations (for quantitative analysis) and the values in brackets are the standard deviations shown as ± variation in the data. The theoretical concentration of luliconazole in each solvent and in model formulations is shown in brackets in the first column.

| Solvents and theoretical strengths (% wt/wt) of luliconazole and formula # are shown in brackets | Solubility wt/wt % 4° C. | | | Solubility wt/wt % RT | | |
|---|---|---|---|---|---|---|
| | 24 hr | 3 days | visual observations at 3 days/4° C. | 24 hr | 3 days | visual observations at 3 days/RT |
| Acetone (18%; #853-38-14) | 13.1 (±0.12) | 12.49 (±0.16) | crystals at bottom | 17.67* (±0.22) | 15.95 (±0.58) | crystals at bottom |
| Ethanol (3.5%; #853-38-15) | 2.67 (±0.06) | 2.3 (±0.02) | crystals at bottom | 3.51 (±0.02) | 3.57 (±0.02) | clear solution |
| Propylene carbonate (10%; #853-38-11) | NA | 5.30 (±0.66) | crystals at bottom | 8.98 (±0.4) | 7.21* (±0.61) | crystals at bottom |
| Ethyl acetate (6.5%; #853-38-12) | 6.14 (±0.59) | 6.49 (±0.07) | clear solution | 6.58* (±0.03) | 6.94 ¶ (±0.27) | clear solution |
| Benzyl alcohol (40%; #853-38-13) | 39.87 (±0.37) | 39.18 (±0.26) | clear solution | 40.19 (±0.25) | 39.91* (±1.37) | clear solution |
| Benzyl alcohol (50%; saturated solution; #802-24-01) | NA | NA | NA | NA | 43.44 (±1.00) | crystals at bottom |
| Transcutol ™ P (15%; #853-38-17) | NA | 14.78 (±0.06) | clear solution | 15.12 (±0.12) | 14.89 (±0.33) | clear solution |
| Transcutol ™ P (20%; saturated solution; 802-24-02) | NA | NA | NA | NA | 16.29 (±0.11) | crystals at bottom |
| Isopropyl myristate (5%; #853-38-10) | NA | NA | NA | 0.41 (±0.002) | NA | crystals at bottom |
| Isopropyl alcohol (5%; #853-38-09) | NA | NA | NA | 1.2 (±0.02) | NA | crystals at bottom |
| Model formula-1 (5.1%; #802-1215A04)ꜰ | NA | NA | NA | NA | 5.13* (±0.05) | clear solution |
| Model formula-2 (5.1%; #802-1219A01) | NA | 5.02 (±0.01) | clear solution | NA | 5.21* (±0.07) | clear solution |

NA: Not available;
*Average duplicate sample preparations;

¶: 4 days at RT;

ꜰ: 1 week at RT luliconazole. Therefore, compatibility of luliconazole with solvents may have to be tested via HPLC on solutions held at room temperature and at 40 or 60° C. However, a careful visual examination of solutions of luliconazole in benzyl alcohol, Transcutol™ P, acetone (all three solvents have high solubility for luliconazole; >15%) were slightly yellow in color however, after 3 days storage at room temperature the color did not change from its initial shade.

The solvents used in both model formulations (802-1215A04 and 802-1219A01) are approved for use in topical formulations by FDA and the amounts of the solvents are less than the maximum potency limits indicated in the FDA-IIG database.

Based on these experiments, luliconazole showed 40% (wt/wt) solubility at both 4° C. and RT in benzyl alcohol. The saturated solution of luliconazole in benzyl alcohol showed luliconazole dissolved at 43% at room temperature.

At room temperature acetone, Transcutol™ P, ethyl acetate, propylene carbonate and ethanol showed about 16%, 15%, 7%, 7% and 3.5% solubility (after 3 days at RT) respectively. However, at 4° C./3 days acetone showed 12% solubility, ethanol showed 2.3%, propylene carbonate showed about 5.3%, and ethyl acetate showed about 6.5% solubility.

Isopropyl alcohol and isopropyl myristate showed about 1.2% and 0.4% solubility respectively at room temperature which is quite low compared to other solvents.

Both model formulations had a theoretical strength of 5% luliconazole. Both showed no crystallization and luliconazole at 5% at RT, identical with the theoretical concentration. The model formulation-2 (802-1219A01) stored at 4° C. for three days also showed no crystallization and luliconazole at 5%, matching the theoretical strength.

From the solubility data and considering the concerns of volatility and compatibility of organic solvents, it was suggested that luliconazole be dissolved in a non-volatile solvent such as benzyl alcohol or Transcutol™ P prior to adding the other organic solvents to complete the formulation.

Ethyl acetate has limited compatibility with certain plastics and elastomers whereas acetone is a very volatile solvent, with a boiling point of 56° C., therefore, use of these solvents in formulations imposes limitations and caution. Use of ethyl acetate may have compatibility issues (container/closure compatibility) and also certain limitations for handling on a large scale. Because acetone is very volatile, handling a stock solution of luliconazole in acetone on a large scale would be challenging. Out of the two model formulations, model formula-2 (802-1219A01) in which luliconazole is dissolved in benzyl alcohol, a non-volatile solvent with a boiling point of 205° C., before the other solvents are added and mixed, would be much easier to prepare batches on a large scale compared to model formula-1 (802-1215A04) which requires making stock solutions of luliconazole in organic solvents including ethyl acetate and acetone.

In one example, it is recommended that luliconazole be first dissolved in a suitable non-volatile solvent such as benzyl alcohol or Transcutol™ P (boiling point 202° C.) prior to adding the other organic solvents so that the formula will be suitable for making large-scale batches.

Example 2

Preparation of Luliconazole Formulations, Including Formulations Containing Greater than 5% wt/wt of Luliconazole Various formulations were prepared and assessed as detailed below.

TABLE 5

Formulations Showing No Crystallization When Stored in a Refrigerator Over 4 Weeks

| Part # | Ingredients | % wt/wt | % wt/wt |
|---|---|---|---|
| 160475 | Alcohol (200 Proof) USP | 46.00 | 41.50 |
| 710400 | Benzyl alcohol, USP | 2.00 | 4.00 |
| 160539 | Propylene Carbonate NF | 5.00 | 5.00 |
| 150000 | Acetone NF | 12.00 | 12.00 |
| 160216 | Transcutol ™ P | 25.00 | 25.00 |
|  | luliconazole | 10.00 | 12.5 |
|  | Total | 100 | 100 |

TABLE 6

Luliconazole Nail Solution Formulations

| | | Lot 768-0107 | | | | | |
|---|---|---|---|---|---|---|---|
| Part # | Ingredient | B01 % w/w | B02 % w/w | B03 % w/w | B04 % w/w | B05 % w/w | B06 % w/w |
| 160475 | Alcohol (200 Proof) USP | 50.00 | 48.60 | 50.00 | 38.00 | 50.00 | 50.00 |
| 710400 | Benzyl Alcohol USP | 14.00 | 2.00 | 14.00 | 2.00 | 14.00 | 14.00 |
| 160539 | Propylene Carbonate NF | 5.00 | | 5.00 | | 5.00 | |
|  | Ethyl Acetate NF | | 28.20 | | 27.00 | | |
| 153230 | Isopropyl Alcohol USP | | | | 10.00 | 6.00 | |
| 153250 | Isopropyl Myristate NF | | | | | | 5.00 |
| 150000 | Acetone NF | 6.00 | 10.20 | 6.00 | 12.00 | | 6.00 |
| 160216 | Transcutol ™ P | 20.00 | 6.00 | 20.00 | 6.00 | 20.00 | 20.00 |
|  | luliconazole | 5.00 | 5.00 | 5.00 | 5.00 | 5.00 | 5.00 |
|  | Total | 100.00 | 100.00 | 100.00 | 100.00 | 100.00 | 100.00 |
|  | Observations | Clear Solution | Clear Solution | Clear Solution | Clear Solution | Clear Solution | Clear Solution |
|  | Refrigerator (days) | NC (7) | NC (7) | NC (7) | NC (7) | NC (7) | NC (7) |
|  | Dry down (25 C. oven) | NC | NC | NC | NC | NC | NC |
|  | Room Temp | no ppt | no ppt | no ppt | no ppt | no ppt | no ppt |

NC = no crystal;
NP = Not performed;
ppt = precipitation;
no ppt = no precipitation As used in the tables herein, "dry down" refers to the procedure whereby using an aluminum weighboat, 1 gram of luliconazole solution was added and placed into a into a 25 C chamber for 1 hour, after which the samples were observed for crystal formation and growth.

TABLE 7(1)

Luliconazole Nail Solution Formulations

| Part # | Ingredient | Lot 768-0115 B01 % w/w | Lot 768-0115 B02 % w/w | Lot 768-0115 B03 % w/w | Lot 768-0116 B01 % w/w | Lot 768-0116 B02 % w/w | Lot 768-0116 B03 % w/w |
|---|---|---|---|---|---|---|---|
| 160475 | Alcohol (200 Proof) USP | 49.00 | 46.00 | 41.50 | 46.00 | 41.50 | 39.00 |
| 710400 | Benzyl Alcohol USP | 2.00 | 2.00 | 4.00 | 2.00 | 4.00 | 4.00 |
| 160539 | Propylene Carbonate NF | 5.00 | 5.00 | 5.00 | 5.00 | 5.00 | 5.00 |
| 150000 | Acetone NF | 12.00 | 12.00 | 12.00 | 12.00 | 12.00 | 12.00 |
| 160216 | Transcutol ™ P | 25.00 | 25.00 | 25.00 | 25.00 | 25.00 | 25.00 |
|  | luliconazole | 7.00 | 10.00 | 12.50 | 10.00 | 12.50 | 15.00 |
|  | Total | 100.00 | 100.00 | 100.00 | 100.00 | 100.00 | 100.00 |
|  | Observations | Clear Solution | Clear Solution | Clear Solution | Clear Solution | Clear Solution | API did not complete Dissolve |
|  | Refrigerator (days) | NC (29) | NC (29) | crystal (29) | NC (28) | NC (28) | NP |
|  | Dry down (25 C. oven) | NC | NC | NC | NC | NC | NP |
|  | Room Temp | ppt | ppt | ppt | no ppt | no ppt | NP |

NC = no crystal;
NP = Not performed;
ppt = precipitation;
no ppt = no precipitation

TABLE 7(2)

Luliconazole Nail Solution Formulations

| Part # | Ingredient | Lot 768-0115 B01 % w/w | Lot 768-0115 B02 % w/w | Lot 768-0115 B03 % w/w | Lot 768-0116 B01 % w/w | Lot 768-0116 B02 % w/w | Lot 768-0116 B03 % w/w |
|---|---|---|---|---|---|---|---|
| 160475 | Alcohol (200 Proof) USP | 49.00 | 46.00 | 43.5 | 46.00 | 41.50 | 39.00 |
| 710400 | Benzyl Alcohol USP | 2.00 | 2.00 | 2.00 | 2.00 | 4.00 | 4.00 |
| 160539 | Propylene Carbonate NF | 5.00 | 5.00 | 5.00 | 5.00 | 5.00 | 5.00 |
| 150000 | Acetone NF | 12.00 | 12.00 | 12.00 | 12.00 | 12.00 | 12.00 |
| 160216 | Transcutol ™ P | 25.00 | 25.00 | 25.00 | 25.00 | 25.00 | 25.00 |
|  | luliconazole | 7.00 | 10.00 | 12.50 | 10.00 | 12.50 | 15.00 |
|  | Total | 100.00 | 100.00 | 100.00 | 100.00 | 100.00 | 100.00 |
|  | Observations | Clear Solution | Clear Solution | Clear Solution | Clear Solution | Clear Solution | API did not complete Dissolve |
|  | Refrigerator (days) | NC (29) | NC (29) | crystal (29) | NC (28) | NC (28) | NP |
|  | Dry down (25 C. oven) | NC | NC | NC | NC | NC | NP |
|  | Room Temp | no ppt | no ppt | no ppt | no ppt | no ppt | NP |

NC = no crystal;
NP = Not performed;
ppt = precipitation;
no ppt = no precipitation

TABLE 8

Luliconazole Nail Solution Formulations

| Part # | Ingredient | Lot 768-0126 B02 % w/w | Lot 768-0126 B03 % w/w | Lot 768-0126 B05 % w/w | Lot 768-0126 B06 % w/w | Lot 768-0126 B07 % w/w |
|---|---|---|---|---|---|---|
| 160475 | Alcohol (200 Proof) USP | 49.00 | 51.00 | 56.00 | 54.00 | 50.50 |
| 710400 | Benzyl Alcohol USP | 4.00 | 2.00 | 2.00 | 4.00 | 2.00 |

TABLE 8-continued

Luliconazole Nail Solution Formulations

| | | Lot 768-0126 | | | | |
|---|---|---|---|---|---|---|
| Part # | Ingredient | B02 % w/w | B03 % w/w | B05 % w/w | B06 % w/w | B07 % w/w |
| 160539 | Propylene Carbonate NF | 5.00 | 5.00 | 5.00 | 5.00 | 5.00 |
|  | Polyvinylpyrrolidone | | | | | 0.50 |
| 150000 | Acetone NF | 12.00 | 12.00 | 12.00 | 12.00 | 12.00 |
| 160216 | Transcutol ™ P | 25.00 | 25.00 | 25.00 | 25.00 | 25.00 |
|  | luliconazole | 5.00 | 5.00 | | | 5.00 |
|  | Total | 100.00 | 100.00 | 100.00 | 100.00 | 100.00 |
|  | Observations | Clear Solution | Clear Solution | Clear Solution | Clear Solution | Clear Solution |
|  | Refrigerator (days) | NC (18) | NP | NP | NP | NC (18) |
|  | Dry down (25 C. oven) | NC | NC | NC | NC | NC |
|  | Room Temp | no ppt | no ppt | no ppt | no ppt | no ppt |

NC = no crystal;
NP = Not performed;
ppt = precipitation;
no ppt = no precipitation

TABLE 9(1)

Luliconazole Nail Solution Formulations

| | | 865-0130 | 865-0206 | | 865-0210 | |
|---|---|---|---|---|---|---|
| Part # | Ingredient | B01 % w/w | B01 % w/w | B02 % w/w | B01 % w/w | B02 % w/w |
| 160475 | Alcohol (200 Proof) USP | 55.50 | 51.00 | 46.50 | 55.00 | 45.50 |
| 710400 | Benzyl Alcohol USP | 2.00 | 2.00 | 4.00 | 2.00 | 4.00 |
| 160539 | Propylene Carbonate NF | 5.00 | 5.00 | 5.00 | 5.00 | 5.00 |
|  | Polyvinylpyrrolidone | 0.50 | | | | |
|  | Gantrez ® ES-425 (50% Butyl ester of PVM/MA, 45% Ethanol, 5% Butyl Alcohol) | | | | 1.00 | 1.00 |
| 150000 | Acetone NF | 12.00 | 12.00 | 12.00 | 12.00 | 12.00 |
| 160216 | Transcutol ™ P | 25.00 | 20.00 | 20.00 | 20.00 | 20.00 |
|  | Luliconazole | | 10.00 | 12.50 | 5.00 | 12.50 |
|  | Total | 100.00 | 100.00 | 100.00 | 100.00 | 100.00 |
|  | Observations | Clear Solution | Clear Solution | Clear Solution | Clear Solution | Clear Solution |
|  | Refrigerator (days) | NP | NC (7) | Crystal (7) | NC (3) | NC (3) |
|  | Dry down (25 C. oven) | NC | Crystal | Crystal | NC | Crystal |
|  | Room Temp | no ppt | ppt | ppt | no ppt | no ppt |
|  | Nail test | | | | No solids | Slight Crystalline residue |

NC = no crystal;
NP = Not performed;
ppt = precipitation;
no ppt = no precipitation As used in the tables, "nail test" refers to a procedure whereby using a transfer pipette, one drop of luliconazole nail solution was applied to a nail and the spreadablity of the solution was observed. After 15 minutes, crystal formation and growth on the nail was assessed as detailed herein.

TABLE 9(2)

Luliconazole Nail Solution Formulations

| | | 865-0130 | 865-0206 | | 865-0210 | |
|---|---|---|---|---|---|---|
| Part # | Ingredient | B01 % w/w | B01 % w/w | B02 % w/w | B01 % w/w | B02 % w/w |
| 160475 | Alcohol (200 Proof) USP | 55.50 | 51.00 | 46.50 | 55.00 | 45.50 |
| 710400 | Benzyl Alcohol USP | 2.00 | 2.00 | 4.00 | 2.00 | 4.00 |

TABLE 9(2)-continued

Luliconazole Nail Solution Formulations

| | | 865-0130 | 865-0206 | | 865-0210 | |
|---|---|---|---|---|---|---|
| | | B01 | B01 | B02 | B01 | B02 |
| Part # | Ingredient | % w/w | % w/w | % w/w | % w/w | % w/w |
| 160539 | Propylene Carbonate NF | 5.00 | 5.00 | 5.00 | 5.00 | 5.00 |
| | Polyvinylpyrrolidone | 0.50 | | | | |
| | Gantrez ® ES-425 (50% Butyl ester of PVM/MA, 45% Ethanol, 5% Butyl Alcohol) | | | | 1.00 | 1.00 |
| 150000 | Acetone NF | 12.00 | 12.00 | 12.00 | 12.00 | 12.00 |
| 160216 | Transcutol ™ P | 25.00 | 20.00 | 20.00 | 20.00 | 20.00 |
| | Luliconazole | | 10.00 | 12.50 | 5.00 | 12.50 |
| | Total | 100.00 | 100.00 | 100.00 | 100.00 | 100.00 |
| | Observations | Clear Solution | Clear Solution | Clear Solution | Clear Solution | Clear Solution |
| | Refrigerator (days) | NP | NC (7) | Crystal (7) | NC (3) | NC (3) |
| | Dry down (25 C. oven) | NC | Crystal | Crystal | NC | Crystal |
| | Room Temp | no ppt | no ppt | no ppt | no ppt | no ppt |
| | Nail test | | | | No solids | Slight Crystalline residue |

NC = no crystal;
NP = Not performed;
ppt = precipitation;
no ppt = no precipitation

TABLE 10

Luliconazole Nail Solution Formulations

| | | 865-0211 | 865-0212 | | | |
|---|---|---|---|---|---|---|
| | | B01 | B01 | B02 | B03 | B04 |
| Part # | Ingredient | % w/w | % w/w | % w/w | % w/w | % w/w |
| 160475 | Alcohol (200 Proof) USP | 58.00 | 52.00 | 50.00 | 50.00 | 45.00 |
| 710400 | Benzyl Alcohol USP | 4.00 | | 2.00 | 2.00 | 2.00 |
| 160539 | Propylene Carbonate NF | 5.00 | 5.00 | 5.00 | 5.00 | 5.00 |
| | Gantrez ® ES-425 (50% Butyl ester of PVM/MA, 45% Ethanol, 5% Butyl Alcohol) | 1.00 | 1.00 | 1.00 | 1.00 | 1.00 |
| 150000 | Acetone NF | 12.00 | 12.00 | 12.00 | 12.00 | 12.00 |
| 160216 | Transcutol ™ P | 20.00 | 25.00 | 25.00 | 25.00 | 25.00 |
| | Luliconazole | | 5.00 | 5.00 | 5.00 | 10.00 |
| | Total | 100.00 | 100.00 | 100.00 | 100.00 | 100.00 |
| | Observations | Clear Solution | Clear Solution | Clear Solution | Clear Solution | Clear Solution |
| | Refrigerator (days) | NP | NP | NP | NP | NC (1) |
| | Dry down (25 C. oven) | NP | NP | NP | NP | NP |
| | Room Temp | NP | NP | NP | NP | NC |

NC = no crystal;
NP = Not performed;
ppt = precipitation;
no ppt = no precipitation

TABLE 11

Luliconazole Nail Solution Formulations

| Ingredient | 1 % w/w | 2 % w/w |
|---|---|---|
| Alcohol (200 Proof) USP | 45.00 | 40.50 |
| Benzyl Alcohol USP | 2.00 | 4.00 |
| Propylene Carbonate NF | 5.00 | 5.00 |
| Gantrez ® ES-425 (50% Butyl ester of PVM/MA, 45% Ethanol, 5% Butyl Alcohol) | 1.00 | 1.00 |
| Acetone NF | 12.00 | 12.00 |
| Diethylene Glycol Monoethyl Ether | 25.00 | 25.00 |
| Luliconazole | 10.00 | 12.50 |
| Total | 100.00 | 100.00 |
| Observations | Clear Solution | Clear Solution |
| Refrigerator (days) | NC | NC |
| Dry down (25 C. oven) | NP | NP |
| Room Temp | NP | NC |

NC = no crystal; NP = Not performed

TABLE 12

Luliconazole Nail Solution Formulations

| Ingredient | 1 % w/w | 2 % w/w | 3 % w/w | 4 % w/w | 5 % w/w | 6 % w/w | 7 % w/w | 8 % w/w |
|---|---|---|---|---|---|---|---|---|
| Alcohol (200 Proof) USP | 48.50 | 50.00 | 50.00 | 48.60 | 50.00 | 38.00 | 50.00 | 50.00 |
| Benzyl Alcohol USP | 2.00 | 14.00 | 14.00 | 2.00 | 14.00 | 2.00 | 14.00 | 14.00 |
| Propylene Carbonate NF | | | 5.00 | 5.00 | | 5.00 | | 5.00 |
| Ethyl Acetate NF | 28.20 | | | 28.20 | | 27.00 | | |
| Isopropyl Alcohol USP | | | | | | 10.00 | 6.00 | |
| Isopropyl Myristate NF | | | | | | | | 5.00 |
| Acetone NF | 10.20 | 6.00 | 6.00 | 10.20 | 6.00 | 12.00 | | 6.00 |
| Transcutol ™ P | 6.00 | 20.00 | 20.00 | 6.00 | 20.00 | 6.00 | 20.00 | 20.00 |
| Luliconazole | 5.10 | 5.00 | 5.00 | 5.00 | 5.00 | 5.00 | 5.00 | 5.00 |
| Total | 100.00 | 100.00 | 100.00 | 100.00 | 100.00 | 100.00 | 100.00 | 100.00 |
| Observations | | | Clear Solution | Clear Solution | Clear Solution | Clear Solution | Clear Solution | Clear Solution |
| Refrigerator (days) | | | NC (7) | NC (7) | NC (7) | NC (7) | NC (7) | NC (7) |
| Dry down (25 C. oven) | | | NC | NC | NC | NC | NC | NC |
| Room Temp | | | NC | NC | NC | NC | NC | NC |

NC = no crystal;
N/A = Not performed

TABLE 13

Luliconazole Nail Solution Formulations

| Ingredient | 15 % w/w | 16 % w/w | 17 % w/w | 18 % w/w | 19 % w/w | 20 % w/w | 21 % w/w | 22 % w/w |
|---|---|---|---|---|---|---|---|---|
| Alcohol (200 Proof) USP | 49.00 | 51.00 | 56.00 | 54.00 | 50.50 | 55.50 | 51.00 | 46.50 |
| Benzyl Alcohol USP | 4.00 | 2.00 | 2.00 | 4.00 | 2.00 | 2.00 | 2.00 | 4.00 |
| Propylene Carbonate NF | 5.00 | 5.00 | 5.00 | 5.00 | 5.00 | 5.00 | 5.00 | 5.00 |
| Polyvinylpyrrolidone | | | | | 0.50 | 0.50 | | |
| Acetone NF | 12.00 | 12.00 | 12.00 | 12.00 | 12.00 | 12.00 | 12.00 | 12.00 |
| Transcutol ™ P | 25.00 | 25.00 | 25.00 | 25.00 | 25.00 | 25.00 | 20.00 | 20.00 |
| Luliconazole | 5.00 | 5.00 | | | 5.00 | | 10.00 | 12.50 |
| Total | 100.00 | 100.00 | 100.00 | 100.00 | 100.00 | 100.00 | 100.00 | 100.00 |
| Observations | Clear Solution | Clear Solution | Clear Solution | Clear Solution | Clear Solution | Clear Solution | Clear Solution | Clear Solution |
| Refrigerator (days) | NC (18) | N/A | N/A | N/A | NC (18) | N/A | NC (7) | Crystal (7) |
| Dry down (25 C. oven) | NC | NC | NC | NC | NC | NC | Crystal | Crystal |
| Room Temp | NC | NC | NC | NC | NC | NC | NC | NC |

NC = no crystal;
N/A = Not performed

TABLE 14

Luliconazole Nail Solution Formulations.

| Ingredient | 23 % w/w | 24 % w/w | 25 % w/w | 26 % w/w | 27 % w/w |
|---|---|---|---|---|---|
| Alcohol (200 Proof) USP | 55.00 | 45.50 | 58.00 | 45.00 | 40.50 |
| Benzyl Alcohol USP | 2.00 | 4.00 | 4.00 | 2.00 | 4.00 |
| Propylene Carbonate NF | 5.00 | 5.00 | 5.00 | 5.00 | 5.00 |
| Gantrez ® ES-425 (50% Butyl ester of PVM/MA, 45% Ethanol, 5% Butyl Alcohol) | 1.00 | 1.00 | 1.00 | 1.00 | 1.00 |
| Acetone NF | 12.00 | 12.00 | 12.00 | 12.00 | 12.00 |
| Transcutol ™ P | 20.00 | 20.00 | 20.00 | 25.00 | 25.00 |
| Luliconazole | 5.00 | 12.50 | | 10.00 | 12.50 |
| Total | 100.00 | 100.00 | 100.00 | 100.00 | 100.00 |
| Observations | Clear Solution | Clear Solution | Clear Solution | Clear Solution | Clear Solution |

TABLE 14-continued

Luliconazole Nail Solution Formulations.

| Ingredient | 23 % w/w | 24 % w/w | 25 % w/w | 26 % w/w | 27 % w/w |
|---|---|---|---|---|---|
| Refrigerator (days) | NC (3) | NC (3) | N/A | NC | NC |
| Dry down (25 C. oven) | NC | Crystal | N/A | N/A | N/A |
| Room Temp | NC No solids | NC Slight Crystalline residue | N/A | Stability samples - evaluated for 6 months at 5 C., 25 C. and at 40 C. | |

NC = no crystal;
N/A = Not performed

TABLE 15

Luliconazole Nail Solution Formulations.

| Ingredient | 28 % w/w | 29 % w/w | 30 % w/w | 31 % w/w | 32 % w/w |
|---|---|---|---|---|---|
| Alcohol (200 Proof) USP | 50.00 | 48.00 | 48.00 | 43.00 | 41.50 |
| Benzyl Alcohol USP | 2.00 | 2.00 | 4.00 | 4.00 | 3.00 |
| Propylene Carbonate NF | 5.00 | 5.00 | 5.00 | 5.00 | 5.00 |
| Gantrez ® ES-425 (50% Butyl ester of PVM/MA, 45% Ethanol, 5% Butyl Alcohol) | 1.00 | 1.00 | 1.00 | 1.00 | 1.00 |
| Acetone NF | 12.00 | 12.00 | 12.00 | 12.00 | 12.00 |
| Transcutol ™ P | 25.00 | 25.00 | 25.00 | 25.00 | 25.00 |
| Luliconazole | 5.00 | 7.00 | 5.00 | 10.00 | 12.50 |
| Total | 100.00 | 100.00 | 100.00 | 100.00 | 100.00 |
| Observations | Clear Solution | Clear Solution | Clear Solution | Clear Solution | Clear Solution |
| Refrigerator (days) | NC | NC | NC | NC | NC |
| Dry down (25 C. oven) | N/A | N/A | N/A | N/A | N/A |
| Room Temp | NC | NC | NC | NC | NC |
| | Stability samples - evaluated for 6 months at 5 C., 25 C. and at 40 C. | | | | |

NC = no crystal;
N/A = Not performed

TABLE 16

Luliconazole Nail Solution Formulations

| Ingredient | 33 % w/w | 34 % w/w | 35 % w/w | 36 % w/w | 37 % w/w | 38 % w/w | 39 % w/w |
|---|---|---|---|---|---|---|---|
| Alcohol (200 Proof) USP | 52.00 | 50.00 | 50.00 | 45.00 | 45.50 | 45.00 | 40.50 |
| Benzyl Alcohol USP | | 2.00 | 2.00 | 2.00 | 4.00 | 2.00 | 4.00 |
| Propylene Carbonate NF | 5.00 | 5.00 | 5.00 | 5.00 | | 5.00 | 5.00 |
| Gantrez ® ES-425 (50% Butyl ester of PVM/MA, 45% Ethanol, 5% Butyl Alcohol) | 1.00 | 1.00 | 1.00 | 1.00 | 1.00 | 1.00 | 1.00 |
| Acetone NF | 12.00 | 12.00 | 12.00 | 12.00 | 12.00 | 12.00 | 12.00 |
| Transcutol ™ P | 25.00 | 25.00 | 25.00 | 25.00 | 25.00 | 25.00 | 25.00 |
| Luliconazole | 5.00 | 5.00 | 5.00 | 10.00 | 12.50 | 10.00 | 12.50 |
| Total | 100.00 | 100.00 | 100.00 | 100.00 | 100.00 | 100.00 | 100.00 |
| Observations | Clear Solution | Clear Solution | Clear Solution | Clear Solution | API did not dissolve | Clear Solution | Clear Solution |
| Refrigerator (days) | N/A | N/A | N/A | NC (1) | N/A | N/A | N/A |
| Dry down (25 C. oven) | N/A | N/A | N/A | N/A | N/A | N/A | N/A |
| Room Temp | N/A | N/A | N/A | NC | N/A | NC | NC |

Stability in plastic vials for 3 months at 25 C and 40 C.
NC = no crystal;
N/A = Not performed

TABLE 17

Luliconazole Nail Solution Formulations

| Ingredient | 40 % w/w | 42 % w/w | 42 % w/w | 43 % w/w | 44 % w/w | 45 % w/w |
|---|---|---|---|---|---|---|
| Alcohol (200 Proof) USP | 40.50 | 45.00 | 40.50 | 40.50 | 40.50 | 40.50 |
| Benzyl Alcohol USP | 4.00 | 2.00 | 4.00 | 4.00 | 4.00 | 4.00 |
| Propylene Carbonate NF | 5.00 | 5.00 | 5.00 | 5.00 | 5.00 | 5.00 |

TABLE 17-continued

Luliconazole Nail Solution Formulations

| Ingredient | 40 % w/w | 42 % w/w | 42 % w/w | 43 % w/w | 44 % w/w | 45 % w/w |
|---|---|---|---|---|---|---|
| Butyl ester of PVM/MA copolymer, 38-52% isopropyl alcohol, <10% butyl alcohol(Gantrez ® ES 435) | 1.00 | 1.00 | 1.00 | 1.00 | 1.00 | 1.00 |
| Acetone NF | 12.00 | 12.00 | 12.00 | 9.60 | 10.20 | 10.80 |
| Transcutol ™ P | 25.00 | 25.00 | 25.00 | 25.00 | 25.00 | 25.00 |
| Luliconazole | 12.50 | 10.00 | 12.50 | 12.50 | 12.50 | 12.50 |
| Total | 100.00 | 100.00 | 100.00 | 97.60 | 98.20 | 98.80 |
| Observations | Clear Solution | Clear Solution | Clear Solution | 80% Acetone Clear Solution | 85% Acetone Clear Solution | 90% Acetone Clear Solution |
| Refrigerator (days) | N/A | N/A | N/A | N/A | N/A | N/A |
| Dry down (25 C. oven) | N/A | N/A | N/A | N/A | N/A | N/A |
| Room Temp | N/A | N/A | N/A | N/A | N/A | N/A |

NC = no crystal;
N/A = Not performed

TABLE 18

Luliconazole Nail Solution Formulations

| Ingredient | 46 % w/w | 47 % w/w | 48 % w/w |
|---|---|---|---|
| Alcohol (200 Proof) USP | 43.00 | 43.00 | 43.00 |
| Benzyl Alcohol USP | 4.00 | 4.00 | 4.00 |
| Propylene Carbonate NF | 5.00 | 5.00 | 5.00 |
| Butyl ester of PVM/MA copolymer, 38-52% isopropyl alcohol, <10% butyl alcohol (Gantrez ® ES 435) | 1.00 | 1.00 | 1.00 |
| Acetone NF |  | 7.02 | 12.00 |
| Transcutol ™ P | 25.00 | 25.00 | 25.00 |
| Luliconazole | 10.00 | 10.00 | 10.00 |
| Total | 88.00 | 95.02 | 100.00 |
| Observations | API did not dissolve into solution | Amount of Acetone needed to dissolve API | Clear Solution |
| Refrigerator (days) | N/A | N/A | N/A |
| Dry down (25 C. oven) | N/A | N/A | N/A |
| Room Temp | N/A | N/A | N/A |

NC = no crystal;
N/A = Not Performed

Example 3

Preparation of 5 kg cGMP Batch of 10 Weight Percent Luliconazole Formulation

Gantrez® ES-435 (0.050 kg) was added to a 10 L stainless steel, round bottom jacketed kettle. The Gantrez® ES-435 container was rinsed with ethanol (200 Proof) USP (1.95 kg) to ensure complete transfer. The solution was mixed using a 1.5 HP air powered dissolver with a 4-inch standard (dissolver) blade. Benzyl alcohol, USP (0.200 kg), propylene carbonate, NF (0.250 kg) and diethylene glycol monoethyl ether, USP/NF (1.25 kg) were added and the solution was mixed until uniform. Acetone, NF (0.63 kg) was added, which included a 5% overage to cover for manufacturing loss. The following preparation was conducted under yellow lighting. Luliconazole (0.5 kg) was added to the solvent mixture and the container was rinsed with alcohol (200 Proof) USP (0.2 kg) to ensure complete transfer. The total alcohol content was 2.15 kg. The luliconazole solution was mixed until all luliconazole solids were visually dissolved to provide a clear, colorless to pale yellow solution, free of particles with a characteristic ethanolic odor. The batch reconciled at 4.97 kg with a 99.4% yield.

Example 4

Dermal Irritation Study of Luliconazole 12.5 Weight Percent Solution During Repeated Topical Application The test sample of Table 19 was used as a representative formulation to evaluate the potential dermal effects of luliconazole compositions containing higher concentrations of luliconazole. Dermal effects were evaluated after 28 consecutive days of dermal application to intact and abraded skin in rabbits. Reversibility, progression, or delayed appearance of any observed irritation following a 2 week postdose observation period was also evaluated.

TABLE 19

Test and Placebo Sample Composition.

| Sample Component | Test Sample Quantity Percent w/w | Placebo Sample Quantity Percent w/w |
|---|---|---|
| Luliconazole | 12.5 | 0 |
| Alcohol (200 proof) | 40.5 | 53.0 |
| Benzyl Alcohol | 4.0 | 4.0 |
| Propylene Carbonate | 5.0 | 5.0 |
| Acetone | 12.0 | 12.0 |
| Gantrez ® ES-435 (50% butyl ester of PVM/MA, 38-52% Isopropyl alcohol, <10% Butyl Alcohol) | 1.0 | 1.0 |
| Diethylene glycol monoethyl ether, NF (Transcutol P) | 25.0 | 25.0 |
| Total | 100 | 100 |

A treatment group of seven New Zealand White Hra: (NZW) SPF albino rabbits received the placebo and test sample daily for 28 days to intact and abraded test sites on each animal at a volume of 0.1 mL/site. An additional intact and abraded site on each animal served as an untreated control. Following 28 days of treatment, three animals were maintained for a 14 day recovery period.

A total of eight male experimentally naïve New Zealand White Hra:(NZW) SPF albino rabbits, approximately 5 months of age at receipt, were received from Covance Research Products, Inc., Kalamazoo, Mich. During the 7 day acclimation period, the animals were observed daily with respect to general health and any signs of disease. A detailed clinical examination was performed on all animals prior to randomization. The animals considered suitable for study were weighed. Using a simple randomization procedure, seven male animals (weighing 2.56 to 3.39 kg at randomization) were assigned to the treatment group identified in Table 20.

TABLE 20

Treatment Groups

| Group Number | Dose Volume (mL/site) | Dose Level (mg/site/day) | Number of Male Animals |
|---|---|---|---|
| 1 | 0.1 | 0/12.5[a] | 7[b] |

[a] All animals received dose levels of 0 and 12.5 mg/site/day on separate abraded and intact sites. An additional abraded and intact site was otherwise untreated.
[b] Following 28 days of treatment, three animals were maintained for a 14 day recovery period.

The animals were individually housed in suspended, stainless steel, slatted floor cages. Yellow lighting was provided for approximately 12 hours per day. The animals were fasted on the day of arrival, and Lab Diet® Certified Rabbit Diet #5322, PMI Nutrition International, Inc., was offered in 25 g increments over 7 days until feeding was approximately 125 g/animal/day thereafter. Tap water was available ad libitum via an automatic watering system. All animals were observed for morbidity, mortality, injury, and the availability of food and water twice daily throughout the duration of the study. Body weights were measured and recorded on the day of receipt, prior to randomization, and weekly during the treatment and recovery periods. There was no effect on body weights. The animals maintained or gained weight over the course of the study.

The placebo and test samples were administered to all animals daily for 28 days by dermal application at a dose volume of 0.1 mL/site. On Day 1 and as needed throughout the study, the hair was removed from the test sites of each animal by close clipping. Three sites on the left side of each animal were abraded on Day 1 and re-abraded weekly during the treatment and recovery periods. The three sites on the right side of each animal remained intact. The placebo and test samples were each applied to one abraded and one intact site on each animal. The remaining abraded and intact site served as an untreated control and was shaved, abraded (as appropriate), and marked in the same manner as the other test sites. Each of the test sites (at the corners) was identified with an indelible black marker to facilitate collection at necropsy. All animals survived to their scheduled necropsy.

The test and placebo samples were applied to a small area (1-inch square, approximately 6 cm²) of skin. The dose was administered in portions to prevent roll off at the dose sites. On Day 1, the animals remained outside of their cages and observed until the dose evaporated and a dermal wash was performed on each site at approximately 4 hours postdose using tepid tap water and a WypAll®. Beginning on Day 2, cervical collars were applied for approximately 2 hours postdose. A dermal wash was not performed unless residual test article was observed.

Dermal Irritation Scoring

The untreated control, placebo control, and treated sites on each animal were evaluated for erythema and edema at approximately 6 hours postdose (2 hours post wash) on Day 1, daily at approximately 2 hours postdose from Days 2 to 7, weekly at approximately 2 hours postdose from Weeks 2 to 4, and weekly during the recovery period. The scoring scale in Table 21 was used and is based upon the Draize scale for scoring skin irritation. Draize J. H. et al, Methods for the Study of Irritation and Toxicity of Substances Applied Topically to the Skin and Mucous Membranes, *J. Pharmacol. Exp. Ther.* 1944; 82:377-390.

TABLE 21

Scoring Scale for Erythema, Eschar and Edema Formation

| Erythema and Eschar Formation | Edema Formation |
|---|---|
| 0 No erythema | 0 No edema |
| 1 Very slight erythema (barely perceptible) | 1 Very slight edema (barely perceptible) |
| 2 Well-defined erythema | 2 Slight edema (edges of area well-defined by definite raising) |
| 3 Moderate to severe erythema | |
| 4 Severe erythema (beet redness) to slight eschar formation (injuries in depth) | 3 Moderate edema (raised approximately 1 mm) |
| | 4 Severe edema (raised more than 1 mm and extending beyond area of exposure) |

Scoring results for the Erythema and Eschar Formation for Days 1-28 are shown in FIGS. 1A and 1B. Scoring results for Edema Formation for Days 1-28 are shown in FIGS. 2A and 2B. Scoring results for the Erythema and Eschar and Edema Formation for Days 35 and 42 are shown in FIGS. 3A, 3B, 3C and 3D.

At the intact and abraded placebo control dose sites, very slight erythema was noted in all animals throughout the dosing period. Well-defined erythema was noted at the abraded dose site in one animal on Days 5 to 7 and sporadically in two animals during the dosing period and at the intact dose site in one animal on Days 5 to 7. These observations resolved during the first week of the recovery period. Very slight edema was noted in one animal on Days 5 and 6 at the abraded placebo dose site. At the intact and abraded test article dose sites, very slight erythema was noted in all animals throughout the dosing period. Well-defined erythema was noted at the abraded dose site in up to 4 animals between Days 5 and Week 2 (Day 14) and at the intact dose site in one animal on Day 5. Very slight erythema was still noted in one animal at the intact and abraded dose sites during the first week of the recovery period. Very slight edema was noted in one animal on Day 5 at the abraded test article dose site. No erythema or edema was noted at the intact and abraded untreated control dose sites during the study.

Postmortem Study Evaluations

Limited necropsy examinations were performed under procedures approved by a veterinary pathologist on all animals euthanized at the terminal (Day 29) or recovery (Day 43) necropsy. The animals were euthanized by intravenous administration of sodium pentobarbital into the ear vein followed by exsanguination from the femoral vessels. The animals were examined carefully for external abnormalities including masses. The skin (the four dose sites and two untreated sites) was collected and preserved in neutral buffered formalin for possible future histological examination. There were no macroscopic observations at the abraded or intact untreated control, placebo control, or test article dose sites.

Under the conditions of this study, where rabbits were dosed once daily with the placebo and test sample, luliconazole (12.5 weight percent solution), for 28 days via dermal administration, there was no cumulative irritation from either the placebo or the test sample. The test and placebo samples were considered to be mild irritants and the test sample was no more irritating than the placebo.

Example 5

Assay for Luliconazole Chemical Stability

The chemical stability of luliconazole in a composition may be assessed by the presence of luliconazole and/or the absence of the luliconazole Z form and SE form. Exemplary methods for detection include those presented in subsections A-C below.

A. Assay for Luliconazole and Luliconazole Z Form

The analytical procedure for determining luliconazole and luliconazole Z form was an isocratic, reversed-phase high performance liquid chromatography (HPLC) method utilizing a photo-diode array PDA) detector. The HPLC method used an Inertsil ODS-2.5 µm, 4.6×150 mm, Column No. SQ5-2785 with a PDA detector, and a mobile phase of ~25 mM Sodium 1-nonanesulfonate in $H_2O$:Acetonitrile:Acetic acid (54:45:1). Under these conditions, luliconazole had a retention time of 10.737 minutes and the luliconazole Z form had a retention time of 9.257 minutes.

B. Assay for Luliconazole and Luliconazole SE Form

The analytical procedure for determining luliconazole SE was an isocratic, chiral reversed-phase HPLC method utilizing a PDA detector. The HPLC used a Chiral Technologies Chiralcel OD-R, 10 µm, 4.6×250 mm, Column No. ODR0CE-MG007 with a PDA detector and a mobile phase of ~150 mM Sodium perchlorate in $MeOH:H_2O$ (4:1). Under these conditions, luliconazole had a retention time of 30.821 minutes and the luliconazole SE form has a retention time of 36.972 minutes.

C. Assay for Luliconazole by Thin Layer Chromatography

A luliconazole standard and a sample solution were dissolved in dichloromethane at approximately 1 mg/mL and spotted on a plate of silica gel with fluorescent indicator. The TLC plate was developed with a mixture of toluene/ethyl acetate/methanol/aqueous ammonia (400:400:20:1) and the plate was air dried. The plate was then examined under UV light and Rf values calculated. The Rf value for luliconazole was calculated to be 0.37. The Rf value for the sample calculated to be 0.36.

Example 6

In Vitro Antifungal Activity of Luliconazole, Luliconazole Z Form and Luliconazole SE Forms The antifungal activities of luliconazole, the Z form of luliconazole, and the SE form of luliconazole were determined. The compounds were tested against the genus *Trichophyton* and the genus *Candida*. The results are shown in Table 22. The MICs against *Trichophyton* were 15-250 times higher for the Z form and 120-1000 times higher for the S-E form than for luliconazole. The MICs against the genus *Candida* were 4-500 times higher for the Z form and 8-1000 times higher for the S-E form than for luliconazole. These results demonstrated the weak antifungal activities of the Z form and the SE form of luliconazole as compared to luliconazole.

TABLE 22

MICs against the Genus *Trichophyton* and the Genus *Candida* of Luliconazole, Luliconazole Z conformation, Luliconazole S-E conformation.

| Species (number of strains) | Compounds | MIC Range (µg/mL) |
| --- | --- | --- |
| *T. mentagrophytes* (4) | Luliconazole | 0.0010-0.0020 |
| | Z conformation | 0.030-0.060 |
| | S-E conformation | 0.50-1.0 |
| *T. rubrum* (4) | Luliconazole | 0.00024-0.00050 |
| | Z conformation | 0.0080-0.060 |
| | S-E conformation | 0.060-0.13 |
| *C. albicans* (6) | Luliconazole | 0.030-0.25 |
| | Z conformation | 1.0-4.0 |
| | S-E conformation | 2.0-4.0 |
| *C. glabrata* (5) | Luliconazole | ≦0.0080-0.030 |
| | Z conformation | 0.50-4.0 |
| | S-E conformation | 0.50-8.0 |

Example 7

Six Month Stability Analysis of Luliconazole Solutions

A 10 weight percent luliconazole solution (solution B04 of Table 25) was used as a representative formulation in an extended stability study.

The luliconazole solution was manufactured (1000 g batch size) and 1 oz amber glass jars were filled with the solution and placed under different temperature conditions at 5° C., 25° C., 40° C. and 60° C., which represent the various storage conditions that the product may encounter. The 5° C. condition was used to accelerate crystal formation if that was to occur. The 25° C. condition represents the ideal storage condition and was used as a control. The 40° C. condition represents an accelerated condition simulating long term storage. The 60° C. condition, which was only tested at 1 week, was used to represent an abusive condition that would promote degradation of luliconazole.

A sample was tested at the beginning of the study for time 0. At each time point (2 weeks, 4 weeks, 6 weeks, 8 weeks, 10 weeks, 12 weeks and 4, 5, and 6 months), a sample from each storage condition was removed and submitted for analytical testing. The analytical results for the 6 month stability study are listed in Table 23. The % L represents the tested result versus the Label claim of 10%. The % RSD represents the relative variance within the replicate samples tested at that time point.

TABLE 23

Six Month Stability Data for 10% Luliconazole Solution

| Solution B04 of Table 25 | Temp | Rep | T = 0 | | T = 2 weeks | | T = 4 weeks | | T = 6 weeks | | T = 8 weeks | |
| --- | --- | --- | --- | --- | --- | --- | --- | --- | --- | --- | --- | --- |
| | | | % w/w | % L | % w/w | % L | % w/w | % L | % w/w | % L | % w/w | % L |
| | RT | 1 | 9.878 | 98.8 | 10.389 | 103.9 | 10.228 | 102.3 | 10.105 | 101.1 | 9.759 | 97.6 |
| | | 2 | 9.940 | 99.4 | 10.380 | 103.8 | 10.265 | 102.7 | 10.076 | 100.8 | 9.774 | 97.7 |

TABLE 23-continued

Six Month Stability Data for 10% Luliconazole Solution

| Temp | Rep | % w/w | % L | % w/w | % L | % w/w | % L | % w/w | % L | % w/w | % L |
|---|---|---|---|---|---|---|---|---|---|---|---|
| | 3 | 9.887 | 98.8 | 10.370 | 103.7 | 10.229 | 102.3 | 10.054 | 100.5 | 9.730 | 97.3 |
| | Mean | 9.901 | 99.0 | 10.380 | 103.8 | 10.240 | 102.4 | 10.078 | 100.8 | 9.754 | 97.5 |
| | % RSD | 0.3 | 0.3 | 0.1 | 0.1 | 0.2 | 0.2 | 0.3 | 0.3 | 0.2 | 0.2 |
| 5° C. | 1 | | | 10.127 | 101.3 | 10.307 | 103.1 | 10.170 | 101.7 | 9.757 | 97.6 |
| | 2 | | | 10.107 | 101.1 | 10.340 | 103.4 | 10.159 | 101.6 | 9.811 | 98.1 |
| | 3 | | | 10.103 | 101.0 | 10.343 | 103.4 | 10.173 | 101.7 | 9.812 | 98.1 |
| | Mean | — | — | 10.112 | 101.1 | 10.330 | 103.3 | 10.167 | 101.7 | 9.793 | 97.9 |
| | % RSD | — | — | 0.1 | 0.1 | 0.2 | 0.2 | 0.1 | 0.1 | 0.3 | 0.3 |
| 40° C. | 1 | | | 10.310 | 103.1 | 10.274 | 102.7 | 10.246 | 102.5 | 10.038 | 100.4 |
| | 2 | | | 10.302 | 103.0 | 10.268 | 102.7 | 10.215 | 102.1 | 10.039 | 100.4 |
| | 3 | | | 10.260 | 102.6 | 10.289 | 102.9 | 10.232 | 102.3 | 10.025 | 100.2 |
| | Mean | — | — | 10.291 | 102.9 | 10.277 | 102.8 | 10.231 | 102.3 | 10.034 | 100.3 |
| | % RSD | — | — | 0.3 | 0.3 | 0.1 | 0.1 | 0.2 | 0.2 | 0.1 | 0.1 |

| | | T = 1 week | |
|---|---|---|---|
| Temp | Rep | % w/w | % L |
| 60° C. | 1 | 10.170 | 101.7 |
| | 2 | 10.211 | 102.1 |
| | 3 | 10.272 | 102.7 |
| | Mean | 10.21 | 102.1 |
| | % RSD | 0.5 | 0.5 |

| | | T = 10 weeks | | T = 12 weeks | | T = 4 months | | T = 5 months | | T = 6 months | |
|---|---|---|---|---|---|---|---|---|---|---|---|
| Temp | Rep | % w/w | % L | % w/w | % L | % w/w | % L | % w/w | % L | % w/w | % L |
| RT | 1 | 10.100 | 101.0 | 9.911 | 99.1 | 10.111 | 101.1 | 10.109 | 101.1 | 10.132 | 101.3 |
| | 2 | 10.138 | 101.4 | 9.923 | 99.2 | 10.107 | 101.1 | 10.152 | 101.5 | 10.095 | 100.9 |
| | 3 | 10.061 | 100.6 | 9.887 | 98.9 | 10.074 | 100.7 | 10.150 | 101.5 | 10.072 | 100.7 |
| | Mean | 10.110 | 101.0 | 9.907 | 99.1 | 10.097 | 101.0 | 10.137 | 101.4 | 10.100 | 101.0 |
| | % RSD | 0.4 | 0.4 | 0.2 | 0.2 | 0.2 | 0.2 | 0.2 | 0.2 | 0.3 | 0.2 |
| 5° C. | 1 | 10.110 | 101.1 | 9.991 | 99.9 | 10.091 | 100.9 | 10.090 | 100.9 | 10.209 | 102.1 |
| | 2 | 10.119 | 101.2 | 9.998 | 100.0 | 10.129 | 101.3 | 10.111 | 101.1 | 10.116 | 101.2 |
| | 3 | 10.132 | 101.3 | 10.001 | 100.0 | 10.089 | 100.9 | 10.106 | 101.1 | 10.149 | 101.5 |
| | Mean | 10.120 | 101.2 | 10.000 | 100.0 | 10.103 | 101.0 | 10.103 | 101.0 | 10.158 | 101.6 |
| | % RSD | 0.1 | 0.1 | 0.1 | 0.1 | 0.2 | 0.2 | 0.1 | 0.1 | 0.5 | 0.5 |
| 40° C. | 1 | 10.062 | 100.6 | 9.977 | 99.8 | 10.101 | 101.0 | 10.097 | 101.0 | 10.143 | 101.4 |
| | 2 | 10.005 | 100.0 | 9.975 | 99.7 | 10.031 | 100.3 | 10.078 | 100.8 | 9.916 | 99.2 |
| | 3 | 10.092 | 100.9 | 9.970 | 99.7 | 10.041 | 100.4 | 10.120 | 101.2 | 10.033 | 100.3 |
| | Mean | 10.053 | 100.5 | 9.974 | 99.7 | 10.058 | 100.6 | 10.098 | 101.0 | 10.031 | 100.3 |
| | % RSD | 0.4 | 0.4 | 0.0 | 0.0 | 0.4 | 0.4 | 0.2 | 0.2 | 1.1 | 1.1 |

The Z-Form of luliconazole was also assayed as part of the stability analysis and the results are provided in Table 24 as peak area percent. The 25° C. data is graphically depicted along with regression line in FIG. 4.

TABLE 24

Luliconazole Z Peak Area Percent Stability Data

| | | T = 6 weeks | | | T = 8 weeks | | | T = 10 weeks | | | T = 12 weeks | | |
|---|---|---|---|---|---|---|---|---|---|---|---|---|---|
| Lot# | Rep | RT | 5° C. | 40° C. | RT | 5° C. | 40° C. | RT | 5° C. | 40° C. | RT | 5° C. | 40° C. |
| Solution B04 of Table 26 | 1 | 0.04 | 0.05 | 0.08 | 0.02 | 0.05 | 0.09 | 0.06 | 0.04 | 0.10 | 0.06 | 0.05 | 0.09 |
| | 2 | 0.06 | 0.04 | 0.08 | 0.06 | 0.05 | 0.09 | 0.06 | 0.05 | 0.10 | 0.05 | 0.05 | 0.10 |
| | 3 | 0.05 | 0.03 | 0.08 | 0.06 | 0.05 | 0.09 | 0.05 | 0.06 | 0.10 | 0.05 | 0.05 | 0.10 |

| | | T = 4 months | | | T = 5 months | | | T = 6 months | | |
|---|---|---|---|---|---|---|---|---|---|---|
| Lot# | Rep | RT | 5° C. | 40° C. | RT | 5° C. | 40° C. | RT | 5° C. | 40° C. |
| Solution B04 of Table 26 | 1 | 0.07 | 0.04 | 0.15 | 0.07 | 0.06 | 0.18 | 0.07 | 0.06 | 0.20 |
| | 2 | 0.05 | 0.05 | 0.16 | 0.07 | 0.07 | 0.20 | 0.08 | 0.05 | 0.19 |
| | 3 | 0.06 | 0.06 | 0.15 | 0.08 | 0.07 | 0.19 | 0.08 | 0.06 | 0.19 |

The study results showed that the luliconazole solution was stable for at least 6 months when stored at room temperature and protected from light, as measured by the assay results and formation of the degradation product (Z-form). The SE form of luliconazole was not detected. The average luliconazole concentration ranged from 97.5-103.8%. As shown in FIG. 4, a linear projection of the 25° C. data projects that the composition will remain stable for up to 24 months.

Additional formulae at concentrations from 5-12.5 weight percent luliconazole as listed in Table 25 were also studied under the above conditions and were deemed stable.

TABLE 25

Luliconazole Solution Formulation 6 Month Stability Batches

| Ingredient | B01 % w/w | B02 % w/w | B01 % w/w | B02 % w/w | B03 % w/w | B04 % w/w |
|---|---|---|---|---|---|---|
| Alcohol (200 Proof) | 45.00 | 40.50 | 50.00 | 48.00 | 48.00 | 43.00 |
| Benzyl Alcohol | 2.00 | 4.00 | 2.00 | 2.00 | 4.00 | 4.00 |
| Propylene Carbonate | 5.00 | 5.00 | 5.00 | 5.00 | 5.00 | 5.00 |
| Gantrez ® ES-425 (50% Butyl ester of PVM/MA, 45% Ethanol, 5% Butyl Alcohol) | 1.00 | 1.00 | 1.00 | 1.00 | 1.00 | 1.00 |
| Acetone | 12.00 | 12.00 | 12.00 | 12.00 | 12.00 | 12.00 |
| Diethylene glycol mono ethyl ether | 25.00 | 25.00 | 25.00 | 25.00 | 25.00 | 25.00 |
| Luliconazole | 10.00 | 12.50 | 5.00 | 7.00 | 5.00 | 10.00 |
| Total | 100.00 | 100.00 | 100.00 | 100.00 | 100.00 | 100.00 |

Example 8

Evaluation of Stability Criteria

Further evaluation of solubility and stability is based upon the composition meeting the criteria as shown in Table 26. The criteria evaluate solubility of luliconazole in the solution as well as chemical and physical stability of luliconazole.

TABLE 26

Solubility and Stability Assays and Criteria

| Test | Luliconazole Solution Criteria |
|---|---|
| Description | Clear, pale yellow solution, free of particles with a characteristic ethanolic odor |
| Identification | The Rf value of the luliconazole spot from the sample solution is comparable to the Rf value of the standard solution. |
| Identification | Retention time of the luliconazole in the sample matches that of the standard |
| Assay | 90-110% of label |
| Impurities Related Substances: | |
| Z-Form | NMT 0.2% |
| SE-Form | NMT 1.0% |
| Any individual Unknown | NMT 0.1% |
| Total | NMT 2.0% |
| Ethanol | 90-110% of formula |
| Acetone | 80-120% of formula |
| Weight Loss | Report results |
| Microbial Limits | |
| Total Aerobic Microbial Count | Not More Than 100 cfu/g |
| S. aureus | Absent |
| P. aerginosa | Absent |

Ethanol and acetone, two volatile ingredients that may be included in the compositions, may be quantified by GC-FID, utilizing a DB-Wax GC column and Flame Ionization Detection.

Example 9

In Vitro Fungicidal Activity in Infected Nail Model Using Human Toe Nails and *T. rubrum*

The efficacy of a 10 weight percent and a 12.5 weight percent luliconazole formulation as shown in Table 27 in comparison to the commercial product Penlac® for the treatment of onychomycosis was assessed in an in vitro infected nail model using human toe nails and *T. rubrum* isolated from an onychomycotic patient as the test organism.

TABLE 27

Test Samples.

| Ingredient | % w/w | % w/w |
|---|---|---|
| Luliconazole | 10.0 | 12.5 |
| Alcohol (200 Proof) | 45.0 | 40.5 |
| Benzyl Alcohol | 2.0 | 4.0 |
| Propylene Carbonate | 5.0 | 5.0 |
| Gantrez ® ES-425 (50% Butyl ester of PVM/MA, 45% Ethanol, 5% Butyl Alcohol) | 1.0 | 1.0 |
| Acetone | 12.0 | 12.0 |
| Transcutol ™ P (Diethylene Glycol Monoethyl Ether) | 25.0 | 25.0 |

A 90 mm PDA plate was seeded with *T. rubrum* with mycelium and spores using a sterile swab removed from a slope culture and transferred onto the surface of the agar. The agar plate was then incubated at 25° C. for 7 days. The white spores were then washed from the surface of the plate with Ringers solution (20 ml). The spore suspension was filtered through a sterile gauze (Smith+Nephew, Propax, 7.5 cm×7.5 cm 8 ply gauze swab, BP Type 13) to remove mycelium and agar debris. A viable count of the spore suspension was adjusted to approximately $1 \times 10^7$ cfu/ml, by diluting or concentrating the spores accordingly in a final volume of 20 ml. Full thickness toe nails were disinfected by washing in 70% ethanol solution, followed by rinsing, cutting into 3 mm×3 mm segments, which were measured for thickness and infected using the above *T. rubrum* cell suspension (5 µL of $\sim 1 \times 10^7$ cfu/ml). At 14 days after which the nail is infected, the ChubTur® cells (MedPharm, United Kingdom) were removed from incubation at 25° C. and 1 µL of the test samples applied to the surface of the nail opposite to where the nail was inoculated with the organism suspension. The nails were dosed daily for 7, 14 and 21 consecutive days.

After incubation, the ChubTur® cells with the formulation applied were removed from incubation. The excess formulation was removed from the surface of the nails and the nails were dismantled from the ChubTur® cells. All the nails were then analyzed for the presence of ATP from the viable fungi using a fluorescence micro-plate reader. The model uses levels of ATP recovered from viable organisms as a biological marker to demonstrate the effectiveness of different formulations in reducing the viability of fungal cells whereby the lower the amount of ATP recovered, the more efficacious the formulation is against fungal cells.

Figure 5:
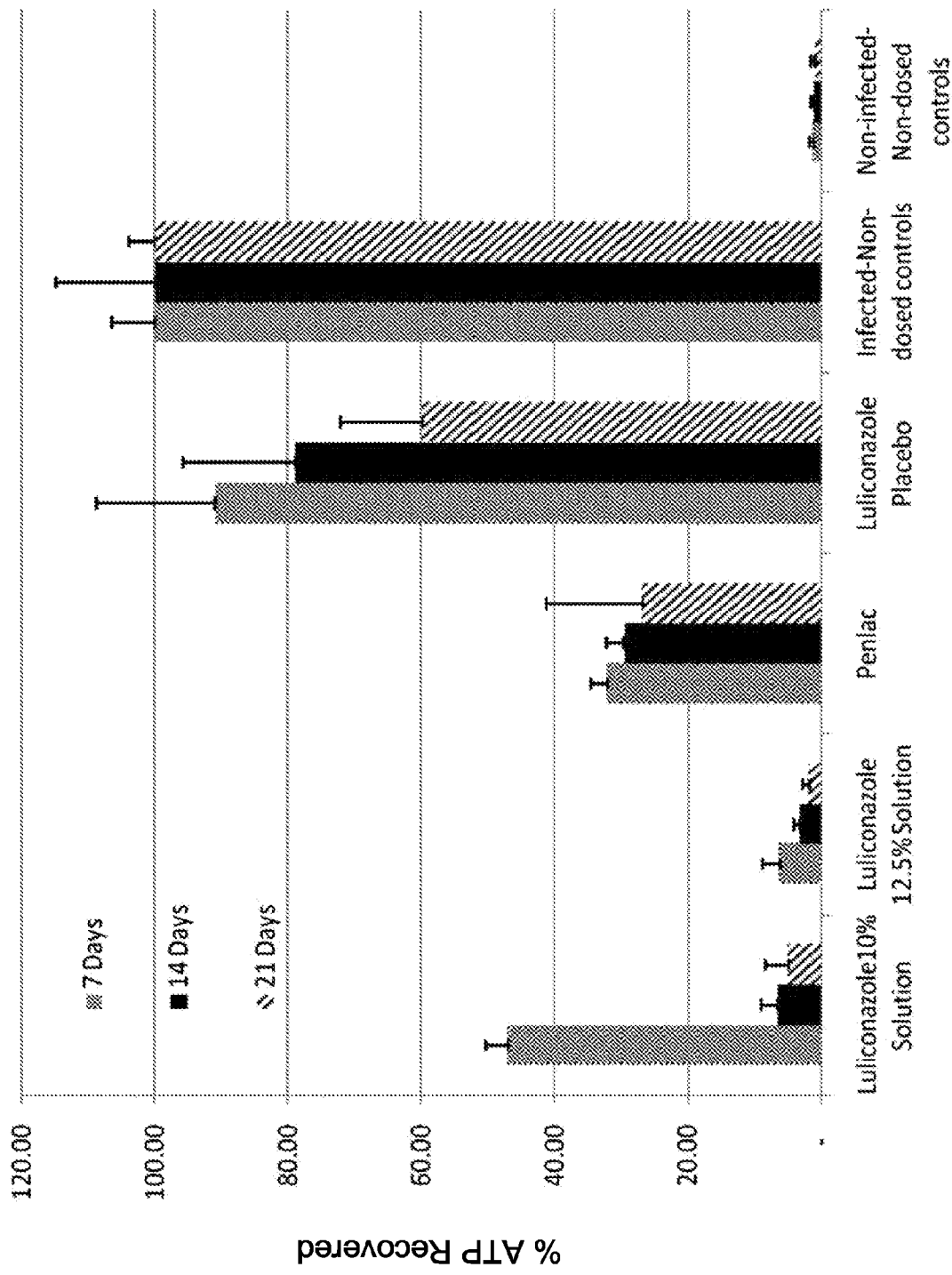
FIG. 5 is a comparison of % ATP recovered after treatment with a 12.5 weight percent luliconazole formulation as compared to infected control following 7, 14 and 21 days application, demonstrating that the 12.5 weight percent luliconazole solution exerted potent fungicidal activity against dermatophytic hyphae after 7 days of once daily application and reduced the ATP content to non-infected baseline levels after 14 days of application, whereas Penlac® showed only partial antifungal activity throughout the experimental period.

The results are summarized in FIG. 5. The results demonstrated that the 12.5 weight percent luliconazole solution exerted potent fungicidal activity against dermatophytic hyphae after 7 days of once daily application and reduced the ATP content to non-infected baseline levels after 14 days of application, whereas Penlac® showed only partial antifungal activity throughout the experimental period. Luliconazole 12.5 weight percent solution was found to be 15 times more effective in killing fungal load than Penlac® ($p<0.00364$) and resulted in a significant reduction in viable dermatophytes recovered from the nail when compared to the untreated control, suggesting that this formulation did cross and the nail has the potential for completely killing the fungal load within a 21 days application under the test conditions of MedPharm's infected nail model against *T. rubrum* in full thickness human toenails.

The luliconazole test formulations (10 and 12.5 weight percent luliconazole) demonstrated significantly stronger fungicidal activity in comparison to Penlac® over a 21 day treatment period against *T. rubrum* in MedPharm's infected toenail model.

Example 10

In Vitro Evaluation of Luliconazole Formulation for Drug Permeation Across Full Thickness Human Nail The permeation of a 10 weight percent luliconazole formulation as a representative of the high concentration luliconazole formulations was determined as compared to a corresponding placebo in a ChubTur® model (MedPharm, United Kingdom) across full thickness human nail. The luliconazole test sample and placebo compositions are detailed in Table 28. The amount of luliconazole in the nail was quantified using the Tursh™ apparatus to perform depth profiling. The amount of drug at different depths of the nail was quantified and compared to the amount of drug permeated across the nail over 7 and 21 days following continuous dosing with the formulation.

TABLE 28

Test and Placebo Sample Composition.

| Sample Component | Test Sample Quantity Percent w/w | Placebo Sample Quantity Percent w/w |
|---|---|---|
| Luliconazole | 10.0 | 0 |
| Alcohol (200 proof) | 43.0 | 53.0 |
| Benzyl Alcohol | 4.0 | 4.0 |
| Propylene Carbonate | 5.0 | 5.0 |
| Acetone | 12.0 | 12.0 |

TABLE 28-continued

Test and Placebo Sample Composition.

| Sample Component | Test Sample Quantity Percent w/w | Placebo Sample Quantity Percent w/w |
|---|---|---|
| Gantrez ® ES-435 (50% butyl ester of PVM/MA, 38-52% Isopropyl alcohol, <10% Butyl Alcohol) | 1.0 | 1.0 |
| Diethylene glycol monoethyl ether, (Transcutol ™ P) | 25.0 | 25.0 |
| Total | 100 | 100 |

The in vitro permeation experiment of a 10 weight percent luliconazole formulation was performed using MedPharm's ChubTur™ model (Khengar, R. H. et al. Pharmaceutical Research (2007) 24:2207-12) and an HPLC method was used for quantification of luliconazole. The HPLC was operated in accordance with the method summarized in Table 29.

TABLE 29

HPLC Method for Luliconazole.

| | |
|---|---|
| HPLC System | Waters 2695 Alliance HPLC system<br>Waters 996 Photo-diode array detector<br>Waters Empower Data Processing Software (version 5.00.00.00) |
| Column | Inertsil ODS 2, 15 cm × 4.6 mm |
| Detection | 295 nm (Diode array detector to be used) |
| Sample Temperature | 25° C. |
| Column Temperature | 40° C. |
| Flow Rate | 1 mL/min (although should be adjusted for column to give API retention time of 12 min) |
| Mobile Phase | 60:39:1 HPLC grade methanol:de-ionise water:glacial acetic acid |
| Injection Volume | 20 µL |
| Run Time | 20 min |
| Approximate retention time | 12 min |
| Needle Wash | 50:50 HPLC grade methanol/deionised water (18.2 MΩ) |
| Pump Wash | 50:50 HPLC grade methanol/deionised water (18.2 MΩ) |

Preparation of mobile phase. 600 mL of HPLC grade methanol, 390 mL de-ionized water (18.2 MΩ) and 10 mL of glacial acetic acid (60:39:1) were measured into a 1 L volumetric flask. The solution was mixed thoroughly using a magnetic stirrer. Separately, 0.576 g±0.005 g of sodium 1-nonanesulfate was weighed out into a 1 L volumetric flask. The methanol, de-ionised water and glacial acetic acid solution was then added and made up to volume. The resulting solution was mixed thoroughly until the sodium 1-nonanesulfate completely dissolved. The solution was stored at room temperature until required.

Preparation of receiver fluid (50:50, Ethanol: Water). 500 mL of HPLC grade ethanol was measured and mixed with 500 mL of de-ionised water (18.2 MΩ) in a 1 L volumetric flask. The resulting solution was mixed thoroughly using a magnetic stirrer. The lid of the volumetric flask was tightly secured by using Parafilm® to occlude or to prevent evaporation of the solvent. The solution was stored at room temperature until required.

Preparation of diluent (60:40, Methanol: Water). 600 mL of HPLC grade methanol was measured and mixed with 400 mL of de-ionised water (18.2 MΩ) in a 1 L volumetric flask. The resulting solution was mixed thoroughly using a magnetic stirrer. The lid of the volumetric was tightly secured by using Parafilm® to prevent evaporation of the solvent. The solution was stored at room temperature until required.

Preparation of luliconazole stock solution and calibration standards. 10 mg±0.1 mg of Luliconazole was weighed into a 10 mL class A volumetric flask. The 60:40 HPLC grade methanol:de-ionised water prepared as above was added to the flask and made up to volume (10 mL) to provide the stock solution with a final concentration of 1000 µg/mL. Subsequent dilutions of the stock were prepared by diluting a known volume of stock in diluent to give concentrations of 100, 75, 50, 25, 10, 5, 1, 0.1, 0.05 and 0.01 µg/ml (see Table 30). An aliquot of each calibration standard solution was transferred to three HPLC vials and labeled. One vial was analyzed, another one placed at 2-8° C. and the last one placed at <−20° C.

TABLE 30

Summary of preparation of calibration standards

| Standard number | Volume of solution (mL) | Volume of volumetric flask (mL) | Final concentration of standard (µg/mL) |
|---|---|---|---|
| 1 | 5 ml of stock | 50 | 100 |
| 2 | 15 ml of standard 1 | 20 | 75 |
| 3 | 5 ml of standard 1 | 10 | 50 |
| 4 | 5 ml of standard 1 | 20 | 25 |
| 5 | 5 ml of standard 1 | 50 | 10 |
| 6 | 5 ml of standard 5 | 10 | 5 |
| 7 | 1 ml of standard 5 | 10 | 1 |
| 8 | 1 ml of standard 5 | 20 | 0.5 |
| 9 | 1 ml of standard 5 | 100 | 0.1 |
| 10 | 5 ml of standard 9 | 10 | 0.05 |
| 11 | 1 ml of standard 9 | 10 | 0.01 |

Preparation of QC standards. 10 mg±0.1 mg of luliconazole was weighed into a 10 mL class A volumetric flask. The 60:40 HPLC grade methanol:de-ionised water prepared as above was added to the flask and made up to volume (10 mL) to provide the stock solution with a final concentration of 1000 µg/mL. Subsequent dilutions of the stock were prepared by diluting a known volume of stock in diluent to give concentrations of 10, 5 and 0.5 µg/ml (Table 31). An aliquot of each calibration standard solution was transferred to three HPLC vials and labeled. One vial was analyzed, another one placed at 2-8° C. and the last one placed at <−20° C.

TABLE 31

Summary of preparation of QC standards

| Standard number | Volume of solution (mL) | Volume of volumetric flask (mL) | Final concentration of standard (µg/mL) |
|---|---|---|---|
| 1 | 1 mL of stock | 100 | 10 |
| 2 | 5 mL of standard 1 | 10 | 5 |
| 3 | 1 mL of standard 1 | 10 | 1 |
| 4 | 1 mL of standard 2 | 20 | 0.5 |

Preparation of nails. The nails (Cadaver) were removed from the freezer and placed under a laminar flow cabinet and allowed to equilibrate to room temperature for 30 minutes. After 30 min, the nails were cut into 3 mm×3 mm segments ensuring that the nails were not damaged in the process. The nails were then immersed into 5 mL of a 70% ethanol in water solution and vortexed for 1 min. The ethanol solution was decanted and replaced with a fresh 5 mL of 70% ethanol solution and vortexed for a further minute. The ethanol solution was decanted and replaced with 5 mL of Ringer's solution and vortexed for 1 min before decanting and replacing with fresh Ringer's. The process of washing with Ringer's was performed 3 times, replacing the wash solution at each phase. The nails were then heated to 60° C. to completely sterilized the nails. Once the washing process was complete, the nails were placed into a sterile Petri dish without a lid and allowed to air dry under a laminar flow cabinet for 30 min at room temperature. The nails were stored at 2-8° C. in a closed sterile container until required.

The thickness of all of the nail sections were measured using a pair of calipers which had been wiped completely with a 70% ethanol in water solution and left to dry under a laminar flow hood for 30 min immediately prior to use (one measurement was taken per sample, due to small sample size). Each nail section was placed carefully into a single well of a sterile 96 well plate using heat sterilized forceps. The thickness and location of the nail in the 96 well plates was recorded.

Experimental set-up. The nail was placed between two washers and mounted aseptically (in the laminar low hood) into the gasket of the ChubTur® cells. The receiver compartment was filled with receiver fluid system. The cells were fixed on a Perspex holder mounted onto a magnetic stirrer in a water bath maintained at 32° C. The receiver compartment was continuously agitated by small PTFE-coated magnetic followers driven by the submersible magnetic stirring board. Once the set of the cells in the water bath was completed, 1 µL of the required formulation was applied onto the surface of the nail daily for 7 days and daily for 21 days (n=6 per formulation). The nails were thoroughly cleaned with a cotton swab pre-soaked in sterile de-ionized water between doses to remove excess formulation. The cells were sampled at regular intervals (See Table 32 for details of sampling intervals) by removing 250 µL of receiver fluid from the receiver compartment and placed into a 2 mL HPLC vial for analysis. For the 7 day daily dosing experiment, sampling time points were T=0, 3 and 7 days, and for the 21 day daily dosing experiment, sampling time points were T=7, 14 and 21 days. The receiver fluid removed for analysis for the presence of luliconazole was replaced with fresh receiver fluid pre-warmed at the same temperature of the water bath (32° C.). Detection of luliconazole in the receiver fluid indicated luliconazole had crossed the nail plate and was delivered to the site of the nail bed.

TABLE 32

Details of the samples investigated:

| Test Item | Formulation | Replicates | Sampling intervals | Dosing | Dosing period (number of days from 1st dosing) |
|---|---|---|---|---|---|
| 3 | 10% Luliconazole Test Sample | n = 6 | T = 0, 3 and 7 days | Daily dosing using 1 µL formulation | 7 Days |
| 2 | Luliconazole placebo nail solution | | | | |
| — | Blank | n = 2 | | No formulation added | |
| 3 | 10% Luliconazole Test Sample | n = 6 | T = 7, 14 and 21 days | Daily dosing using 1 µL formulation | 21 Days |
| 2 | Luliconazole placebo nail solution | | | | |
| — | Blank | n = 2 | | No formulation added | |

Tursh™ depth profiling assay—Quantification of Luliconazole in nail. The nails were dismantled from the gasket of the ChubTur® cells ensuring the nails had been completely cleaned of all residual formulation. The nail was placed on to the accurate fine adjustment platform of the Tursh™ apparatus which held the nail in place. The micrometer on the underside of the device was adjusted to the required depth so that nail samples were taken from the top, middle and bottom that is at depths of 0-0.2 mm, 0.2-0.4 mm and 0.4 mm-base). Using a Dremel® drill fitted at high speed with a 3.2 mm flat headed bore cutter, the nail was drilled into very slowly ensuring the nail was firmly in place. The resulting nail powder at each depth was collected. All vials were labeled with the correct depth. Once the powdered nail samples from each depth has been collected, 1 mL of methanol was added to each vial and sonicated for 30 min. The amount of luliconazole in each solution was then quantified using the HPLC method implemented.

Figure 6:
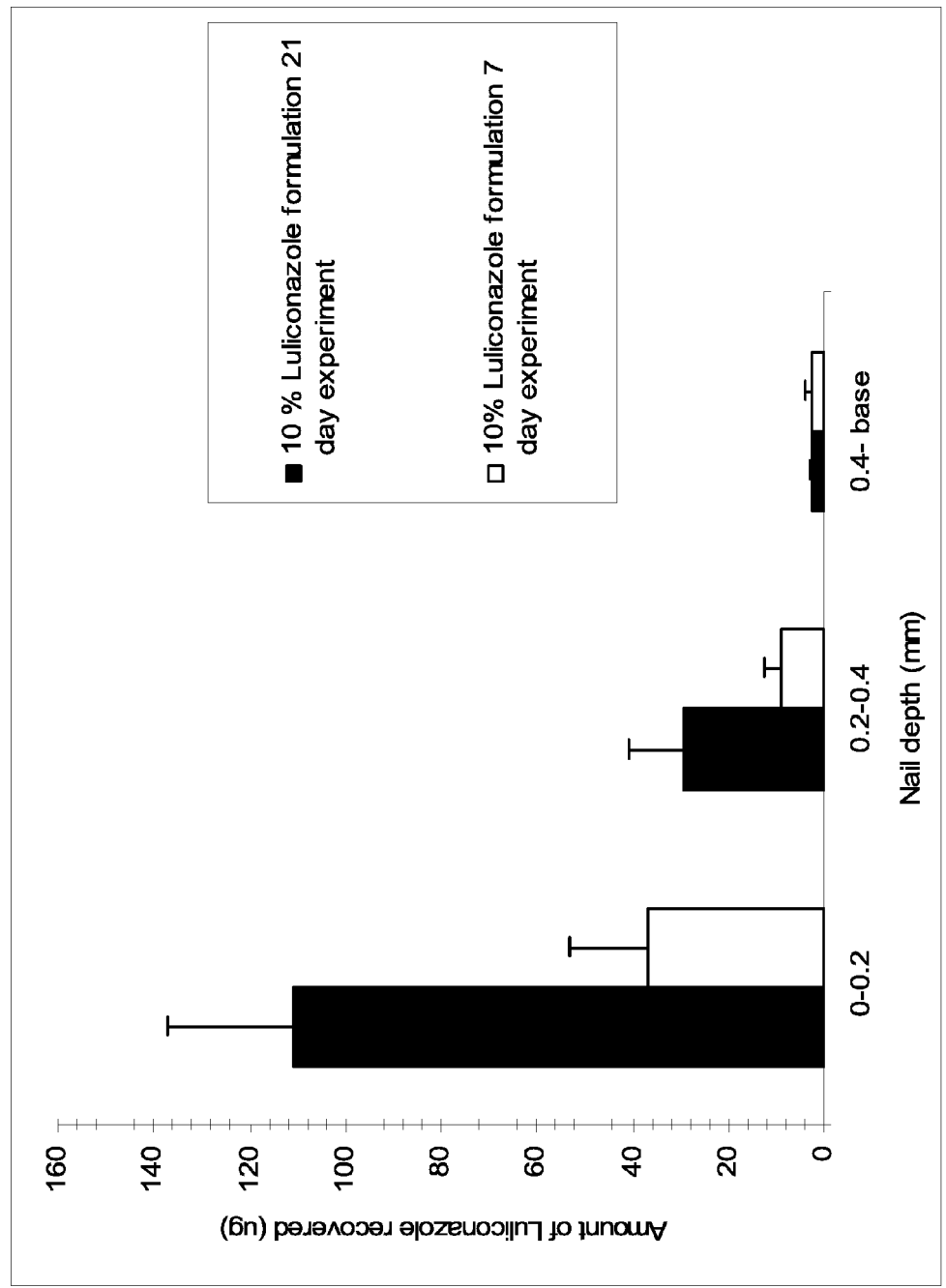
FIG. 6 is a graph depicting the amount of luliconazole recovered from different nail depths after application of a 10 weight percent luliconazole formulation and placebo formulation (Mean±SEM (n=6)), indicating that the amount of luliconazole recovered from the nail samples correlated with the depth of the nail assayed, whereby deeper layers of the nail contained less luliconazole.

Depth profiling. FIG. 6 depicts the recovery of luliconazole from each of the nail samples. It can be observed from the graph that the amount of luliconazole recovered from the nail samples correlated with the depth of the nail assayed, whereby deeper layers of the nail contained less luliconazole. The data also demonstrated that the longer the dose period, the more amount of drug recovered at each depth. Therefore the amount of luliconazole recovered at each depth after 21 continuous days was greater compared to the amount recovered after 7 continuous days of dosing. No luliconazole was recovered from the nails treated with the placebo formulations and the blank controls which had no formulation applied to the nails.

The amount of luliconazole recovered from different nail depths following 7 days continuous dosing with the 10 weight percent luliconazole test sample and placebo was compared to the amount of luliconazole recovered from different nail depths following 7 days continuous dosing with a saturated 10 mg/mL luliconazole solution in 1% Tween 80/phosphate buffer (1 weight percent luliconazole). The results are shown in Table 33, which demonstrate the greater amounts of luliconazole recovered at each nail depth after 7 days continuous dosing with the 10 weight percent luliconazole test sample compared to the saturated 10 mg/mL luliconazole solution in 1% Tween 80/phosphate buffer (1 weight percent luliconazole).

TABLE 33

Amount of luliconazole recovered from different nail depths following 7 days continuous dosing with 10% luliconazole Test Sample, Saturated luliconazole solution (10 mg/mL) in 1% Tween 80/Phosphate buffer and luliconazole placebo formulation (Mean ±SEM).

| Treatment/depth | Amount of Luliconazole (μg) | | |
|---|---|---|---|
| | 0-0.2 mm | 0.2-0.4 mm | 0.4 mm-base |
| 10% Luliconazole formulation | 36.71 ± 16.31 | 9.31 ± 3.05 | 2.52 ± 1.24 |
| Saturated luliconazole solution (10 mg/mL) | 2.29 ± 0.35 | 0.33 ± 0.10 | 0.08 ± 0.02 |
| Luliconazole placebo formulation | 0.00 | 0.00 | 0.00 |

Figure 7:
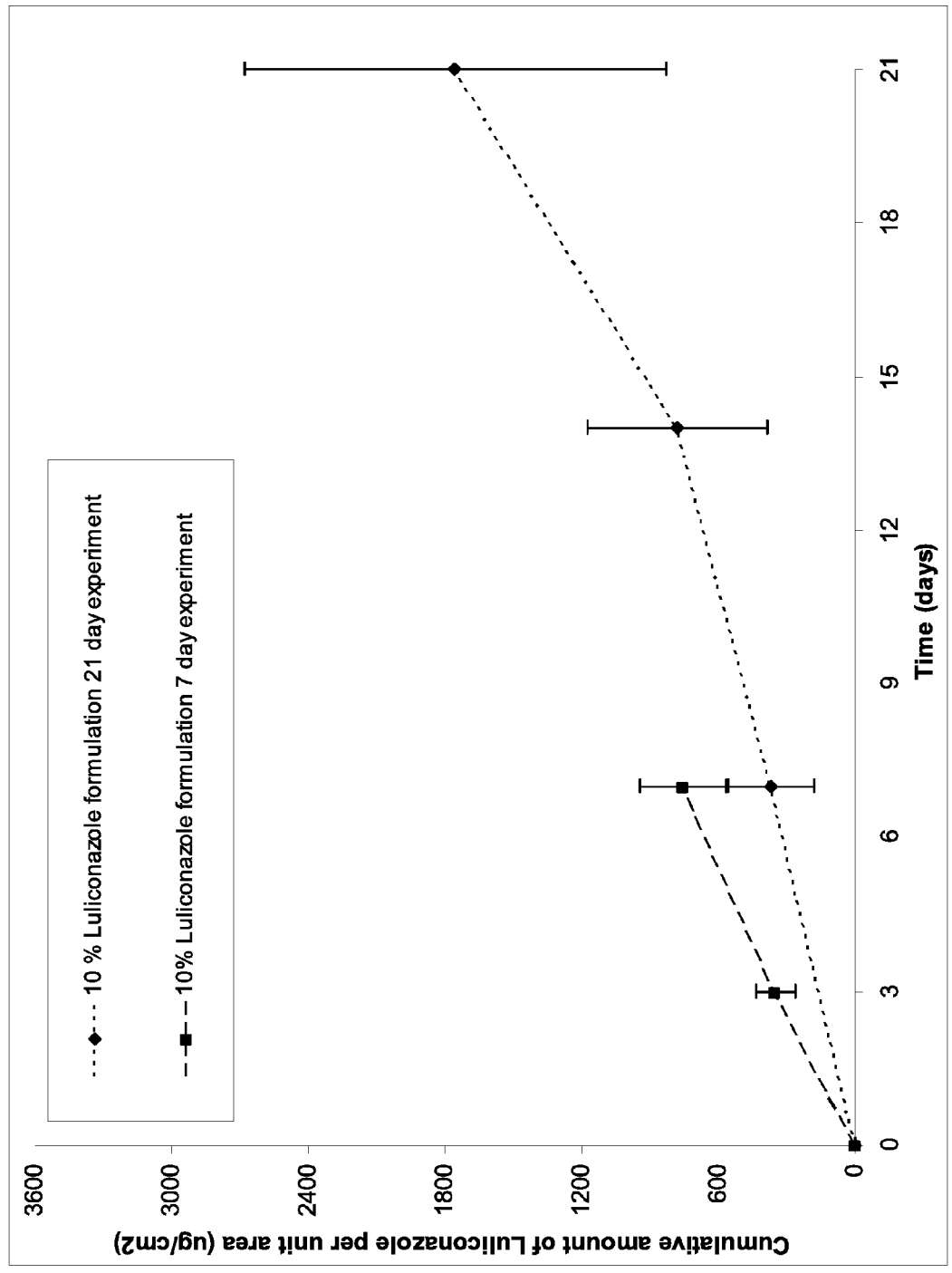
FIG. 7 is a graph depicting luliconazole's permeation through the nail after continuous dosing for 7 and 21 days (Mean±SEM, n=6) with assay time points for the 7 day dosing experiment at T=0, 3 and 7 days and for the 21 day dosing experiment T=7, 14 and 21 days, showing steady state permeation up to 7 days in the 7 day experiment and up to 14 days in the 21 day experiment.

Permeation profile. The data for the permeation of luliconazole using full thickness nail is depicted in Tables 34 (7 days continuous dosing) and 35 (21 days continuous dosing) and graphically summarized in FIG. 7. The data show that the 10 weight percent luliconazole test sample showed steady state permeation up to 7 days in the 7 day experiment and up to 14 days in the 21 day experiment. There was no significant difference (p>0.05) in permeation of luliconazole over 7 days in both the 7 and 21 day experiments.

TABLE 34

Cumulative permeation of Luliconazole for after 7 days continuous dosing with 10 weight percent Luliconazole formulation

| Cell/timepoint (h) | Cumulative permeation of luliconazole (μg) over time (days) | | |
|---|---|---|---|
| | 0 | 3 | 7 |
| 10% Luliconazole n = 1 | 0.00 | 140.96 | 198.59 |
| 10% Luliconazole n = 2 | 0.00 | 231.63 | 300.77 |
| 10% Luliconazole n = 3 | 0.00 | 345.54 | 881.05 |
| 10% Luliconazole n = 4 | 0.00 | 396.80 | 806.01 |
| 10% Luliconazole n = 5 | 0.00 | 242.50 | 856.78 |
| 10% Luliconazole n = 6 | 0.00 | 737.84 | 1492.26 |
| Average | 0.00 | 349.21 | 755.91 |
| SD | 0.00 | 210.66 | 466.54 |
| SE | 0.00 | 86.00 | 190.47 |

TABLE 35

Cumulative permeation of Luliconazole for after 21 days continuous dosing with 10% Luliconazole formulation

| Cell/timepoint (h) | Cumulative permeation of Luliconazole (μg) over time (days) | | | |
|---|---|---|---|---|
| | 0 | 7 | 14 | 21 |
| 10% Luliconazole n = 1 | 0.00 | 0.00 | 0.00 | 0.00 |
| 10% Luliconazole n = 2 | 0.00 | 0.00 | 0.00 | 0.00 |
| 10% Luliconazole n = 3 | 0.00 | 1094.672 | 1583.96 | 3906.12 |
| 10% Luliconazole n = 4 | 0.00 | 708.08 | 826.59 | 1408.95 |
| 10% Luliconazole n = 5 | 0.00 | 399.02 | 2253.72 | 5202.20 |
| 10% Luliconazole n = 6 | 0.00 | 21.42 | 16.39 | 17.78 |
| Average | 0.00 | 370.53 | 780.11 | 1755.84 |
| SD | 0.00 | 455.10 | 961.28 | 2271.93 |
| SE | 0.00 | 185.79 | 392.44 | 927.51 |

Flux. The data in Table 36 shows the flux of luliconazole in the 7 and 21 day experiments. The data demonstrates that the flux of luliconazole in both experiments was comparable and no statistical difference (p>0.05) was observed between either. The flux for the 7 day experiment was calculated from (0-7 days) and the flux for the 21 day experiment was calculated from (0-21 days) and (7-21 days). There was also no significant difference (p>0.05) between the flux from (0-21 days) and (7-21 days) for the 21 day experiment.

TABLE 36

Summary of the amount of Luliconazole permeated per unit area per day after continuous dosing for 7 and 21 days (Mean ± SEM, n = 6).

| Treatment | Flux (μg/cm$^3$/day) |
|---|---|
| 10% Luliconazole formulation 7 day experiment | 107.75 ± 27.21 |
| 10% Luliconazole formulation 21 day experiment (calculated over two ranges): | |
| 1) 0-21 days | 1) 81.10 ± 43.60 |
| 2) 7-21 days | 2) 98.95 ± 58.25 |

The results demonstrate the flux rate was consistent with time and suggest a steady state of drug is reached within 7 days of treatment.

The amount of luliconazole recovered from the nail samples correlated with the depth of the nail assayed, whereby deeper layers of the nail contained less luliconazole. It was also observed that the longer the dose period, the greater the amount of drug recovered at each depth. The data from the permeation experiments demonstrated that the 10 weight percent luliconazole showed steady state permeation up to 7 days in the 7 day experiment and up to 14 days in the 21 day experiment. There was no significant difference (p>0.05) in permeation of luliconazole over 7 days in both the 7 and 21 day experiments.

Example 12

Assessment of Mycological Cure of Onychomycosis in Human Nail

The nail of an individual receiving or having received treatment for onychomycosis is assessed for mycological cure by negative KOH (potassium hydroxide) and fungal culture. The KOH procedure is typically done at the physician's office. Material for KOH is obtained from the infected part of the nail. In distal subungual onychomycosis, the hyperkeratotic, subungual debris at the most proximal area of the infected nail unit provides the ideal specimen. The material is placed on a glass slide and 10% to 15% KOH is added. The addition of dimethyl sulfoxide to KOH solution is often used as well as a fungal stain such as Chlorazol Black E, which is chitin specific or Parker's blue black ink to enhance visualization of fungal hyphae under a microscope. Since dead fungal hyphae may produce a positive result (false positive) in the KOH test, a sample for fungal culture is used to confirm the presence or absence of infection in the nail. The KOH and fungal culture assays for dermatophytes in the nail specimen may be performed according to Drake et al. Journal of the American Academy of Dermatology (1996) 116-121.

Example 13

Assessment of Clinical Cure of Onychomycosis in Human Nail

The nail of an individual receiving or having received treatment for onychomycosis is assessed for zero percent clinical involvement of the nail as determined by the presence of a clear nail and the absence of clinical signs of onychomycosis.

Example 14

Use of Human Clinical Trials to Determine the Ability of a Luliconazole Composition to Treat Onychomycosis Standard methods can be used for these clinical trials. In one exemplary method, subjects with onychomycosis are enrolled in a tolerability, pharmacokinetics and pharmacodynamics phase I study using standard protocols. A phase II, double-blind randomized controlled trial is performed to determine the safety and efficacy of the compositions using standard protocols. These protocols can be carried out to assess various formulations and dosing regimens.

What is claimed is:

1. A method of treating onychomycosis in an individual in need thereof, comprising contacting the individual's nail with a pharmaceutical composition comprising:
   from about 9 weight percent to about 12.5 weight percent luliconazole;
   from about 8 weight percent to about 15 weight percent acetone;
   from about 3 weight percent to about 8 weight percent propylene carbonate;
   from about 20 weight percent to about 30 weight percent of an ethylene glycol derivative of the formula $HOCH_7CH_2OCH_7CH_2OR$ where R is an alkyl group having 1 to 6 carbon atoms;
   from 0.01 weight percent to about 6 weight percent benzyl alcohol;
   from 0.01 weight percent to about 4 weight percent of a film forming agent; and
   from about 20 weight percent to about 60 weight percent of ethanol.

2. The method of claim 1, wherein R is ethyl.

3. The method of claim 1, wherein the composition comprises 2 weight percent to 4 weight percent benzyl alcohol.

4. The method of claim 1, wherein the film-forming agent is a maleic anhydride/methyl vinyl ether copolymer.

5. The method of claim 1, wherein the film forming agent is a butyl ester of polyvinylmethylether maleic anhydride copolymer.

6. The method of claim 1, wherein the composition comprises from about 35 weight percent to about 45 weight percent ethanol.

7. The method of claim 3, wherein R is ethyl.

8. The method of claim 4, wherein the composition comprises about 2 weight percent to about 4 weight percent benzyl alcohol.

9. The method of claim 2, wherein the film-forming agent is a maleic anhydride/methyl vinyl ether copolymer.

10. The method of claim 2, wherein the film forming agent is a butyl ester of polyvinylmethylether maleic anhydride copolymer.

11. The method of claim 8, wherein the composition comprises from about 35 weight percent to about 45 weight percent ethanol.

12. The method of claim 1, wherein the composition comprises about 10 weight percent luliconazole.

13. The method of claim 1, wherein the method is a method of treating distal subungual onychomycosis.

14. The method of claim 1, wherein the onychomycosis is an infection of a toenail.

15. The method of claim 1, wherein the onychomycosis is an infection of a fingernail.

16. The method of claim 1, wherein the method comprises contacting the individual's nail with the composition once daily.

17. The method of claim 1, wherein the individual is diabetic, is of an advanced age or is immunocompromised.

18. The method of claim 1, wherein the composition comprises:
   from 9 weight percent to 12.5 weight percent luliconazole;
   from 8 weight percent to 15 weight percent acetone;
   from 3 weight percent to 8 weight percent propylene carbonate;
   from 20 weight percent to 30 weight percent of an ethylene glycol derivative of the formula $HOCH_2CH_2OCH_2CH_2OR$ where R is an alkyl group having 1 to 6 carbon atoms;

from 0.01 weight percent to 6 weight percent benzyl alcohol;

from 0.01 weight percent to 4 weight percent of a film forming agent; and from 20 weight percent to 60 weight percent of ethanol.

19. The method of claim 18, wherein the composition comprises:

10 weight percent luliconazole;

12 weight percent acetone;

5 weight percent propylene carbonate;

25 weight percent of an ethylene glycol derivative of the formula $HOCH_2CH_2OCH_2CH_2OR$ where R is ethyl; and 4 weight percent benzyl alcohol.

20. The method of claim 19, wherein the composition further comprises a film forming agent in 1 weight percent.

21. The method of claim 20, wherein the film-forming agent is a maleic anhydride/methyl vinyl ether copolymer.

22. The method of claim 20, wherein the film forming agent is a butyl ester of polyvinylmethylether maleic anhydride copolymer.

* * * * *

UNITED STATES PATENT AND TRADEMARK OFFICE
CERTIFICATE OF CORRECTION

PATENT NO. : 8,193,233 B2
APPLICATION NO. : 12/750563
DATED : June 12, 2012
INVENTOR(S) : Charles G. Vontz et al.

It is certified that error appears in the above-identified patent and that said Letters Patent is hereby corrected as shown below:

In the Specifications:

Column 3, line 28, please replace "series" with --serious--.

Column 4, line 58, please replace "loosing" with --losing--.

Column 4, line 64, please replace "laquer" with --lacquer--.

Column 4, line 66, please replace "assoicated" with --associated--.

Column 7, line 5, please replace "comprises" with --comprise--.

Column 7, line 29, please delete "an".

Column 8, line 43, please replace "IN" with --In--.

Column 8, line 64, please replace "on" with --one--.

Column 12, line 19, please replace "one" with --once--.

Column 20, line 34, please replace "use a kit" with --use in a kit--.

Column 20, line 66, please replace "use an article" with --use in an article--.

Column 20, line 67, please replace "a article" with --an article--.

Column 22, line 14, please replace "antifugal" with --antifungal--.

Column 22, line 61, please replace "al," with --al.,--.

Signed and Sealed this
Fourth Day of June, 2013

Teresa Stanek Rea
*Acting Director of the United States Patent and Trademark Office*

CERTIFICATE OF CORRECTION (continued)
U.S. Pat. No. 8,193,233 B2

Column 23, line 61, please replace "bentonite, bentonite," with --bentonite,--.

Column 24, line 2, please replace "carbomer 980, carbomer 980," with --carbomer 980,--.

Column 24, line 17, please delete "crospovidone".

Column 24, line 23, please delete "diethylene glycol monoethyl ether,".

Column 24, line 44, please replace ""glyceryl oleate, glyceryl oleate," with --glyceryl oleate,--.

Column 24, line 53, please delete "hydroxyethyl cellulose,".

Column 24, line 55, please delete "hydroxypropyl cellulose,".

Column 24, line 60, please replace "isopropyl myristate, isopropyl myristate," with --isopropyl myristate,--.

Column 25, line 19, please replace "octyldodecanol, octyldodecanol," with --octyldodecanol,--.

Column 25, line 44, please delete "polyisobutylene 1,200,000,".

Column 25, line 60, please replace "polysorbate 20, polysorbate 20," with --polysorbate 20,--.

Column 25, line 62, please replace "polyvinyl alcohol, polyvinyl alcohol" with --polyvinyl alcohol,--.

Column 26, line 4, please delete "propylene glycol, propylene glycol,".

Column 26, line 19, please replace "sodium citrate, sodium citrate," with --sodium citrate,--.

Column 26, line 34, please delete "sorbitan monooleate,".

Column 26, line 47, please replace "titanium dioxide, titanium dioxide," with --titanium dioxide,--.

Column 26, line 53, please replace "tromethamine, tromethamine," with --tromethamine,--.

Column 26, line 57, please replace "xanthan gum, xanthan gum" with --xanthan gum--.

CERTIFICATE OF CORRECTION (continued)
U.S. Pat. No. 8,193,233 B2

Column 27, line 20, please replace "Niklol" with --Nikkol--.

Column 28, line 58, please replace "Labrafl" with --Labrafil--.

Column 28, line 60, please replace "Labrafl" with --Labrafil--.

Column 28, line 65, please replace "Labrafl" with --Labrafil--.

Column 28, line 66, please replace "Labrafl" with --Labrafil--.

Column 32, line 42, please replace "glyco chenodeoxycholate" with --glycochenodeoxycholale--.

Column 49, line 65, please replace "luliconazol" with --luliconazole--.

In the Claims:

Column 82, line 13, please replace "$HOCH_7CH_2OCH_7CH_2OR$" with --$HOCH_2CH_2OCH_2CH_2OR$--.